United States Patent
Yoo et al.

(10) Patent No.: US 9,066,922 B2
(45) Date of Patent: Jun. 30, 2015

(54) PHARMACEUTICAL COMPOSITION FOR THE TREATMENT OR PREVENTION OF DISEASES INVOLVING OBESITY, DIABETES, METABOLIC SYNDROME, NEURO-DEGENERATIVE DISEASES AND MITOCHONDRIA DYSFUNCTION DISEASES

(71) Applicants: MD BIOALPHA CO., LTD., Daejeon (KR); KT & G CO., LTD., Daejeon (KR)

(72) Inventors: Sang-Ku Yoo, Gwacheon-si (KR); Myunggyu Park, Yongin-si (KR); In Geun Jo, Cheonan-si (KR); Taehwan Kwak, Yongin-si (KR)

(73) Assignees: MD BIOALPHA CO., LTD., Daejeon (KR); KT & G CO., LTD., Daejeon (KR)

( * ) Notice: Subject to any disclaimer, the term of this patent is extended or adjusted under 35 U.S.C. 154(b) by 0 days.

(21) Appl. No.: 13/870,350

(22) Filed: Apr. 25, 2013

(65) Prior Publication Data
US 2013/0245111 A1    Sep. 19, 2013

Related U.S. Application Data

(63) Continuation of application No. 12/470,514, filed on May 22, 2009, now Pat. No. 8,466,141, which is a continuation of application No. 11/816,438, filed as application No. PCT/KR2006/000531 on Feb. 15, 2006, now abandoned.

(30) Foreign Application Priority Data

Feb. 16, 2005    (KR) .................. 10-2005-0012625

(51) Int. Cl.
| | | |
|---|---|---|
| A01N 43/00 | (2006.01) | |
| A61K 31/33 | (2006.01) | |
| A01N 43/16 | (2006.01) | |
| A61K 31/35 | (2006.01) | |
| A61K 31/352 | (2006.01) | |
| A61K 31/343 | (2006.01) | |
| A61K 31/353 | (2006.01) | |
| A61K 31/453 | (2006.01) | |

(52) U.S. Cl.
CPC ............. *A61K 31/352* (2013.01); *A61K 31/343* (2013.01); *A61K 31/353* (2013.01); *A61K 31/453* (2013.01)

(58) Field of Classification Search
CPC .......................... A61K 31/353; A61K 31/343
USPC ................................................. 514/183, 454
See application file for complete search history.

(56) References Cited

U.S. PATENT DOCUMENTS

| | | |
|---|---|---|
| 5,969,163 A | 10/1999 | Frydman et al. |
| 6,183,948 B1 | 2/2001 | Marban et al. |
| 2004/0207589 A1 | 10/2004 | Kim et al. |
| 2005/0002565 A1 | 1/2005 | Han et al. |
| 2005/0147293 A1 | 7/2005 | Lee et al. |
| 2006/0082689 A1 | 4/2006 | Moldvai |

FOREIGN PATENT DOCUMENTS

| | | |
|---|---|---|
| JP | 2003-046779 A | 2/2003 |
| JP | 2005-160015 A | 6/2005 |
| JP | 2005-184787 A | 7/2005 |
| JP | 2005-196108 A | 7/2005 |
| KR | 10-2003-0099556 A | 12/2003 |
| KR | 10-2003-0099557 A | 12/2003 |
| KR | 10-2003-0099657 A | 12/2003 |
| KR | 10-2003-0099658 A | 12/2003 |
| KR | 10-2004-0006065 A | 1/2004 |
| KR | 10-2004-7005109 A | 4/2004 |
| KR | 10-2004-0036195 A | 5/2004 |
| KR | 10-2004-0036197 A | 5/2004 |
| KR | 10-2004-0050200 A | 6/2004 |
| KR | 10-2004-0064950 A | 7/2004 |

(Continued)

OTHER PUBLICATIONS

Lai et. al. (Histology and Histopathology (1998) 13(1) 89-97).*

(Continued)

*Primary Examiner* — Marcos Sznaidman
(74) *Attorney, Agent, or Firm* — Birch, Stewart, Kolasch & Birch, LLP

(57) ABSTRACT

Provided is a pharmaceutical composition for the treatment and prevention of obesity, diabetes, metabolic syndromes, degenerative diseases and mitochondrial dysfunction-related diseases, comprising: a therapeutically effective amount of a compound represented by Formula I below, or a pharmaceutically acceptable salt, prodrug, solvate or isomer thereof, and a pharmaceutically acceptable carrier, a diluent or an excipient, or any combination thereof.

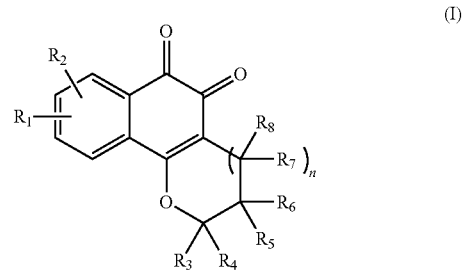

wherein $R_1$ through $R_8$ and n are as defined in this disclosure.

6 Claims, 18 Drawing Sheets

(56) References Cited

FOREIGN PATENT DOCUMENTS

| | | |
|---|---|---|
| KR | 10-2006-0017813 A | 2/2005 |
| KR | 10-2005-0104890 A | 11/2005 |
| KR | 10-2006-0095203 A | 8/2006 |
| KR | 10-2006-0112598 A | 11/2006 |
| WO | WO 2006/024545 A1 | 3/2006 |

OTHER PUBLICATIONS

Tolman (Ann. Intern. Med. (2004) 141:946-956).*
Calamita et. al. (Expert Opinion on Therapeutic Targets (2007) 11:1231-1249).*
Arch. Biochem. Biophys. 380, 347-352, 2000.
Attele et al, "Antidiabetic Effects of Panax Ginseng Berry Extract and the Identification of an Effective Component," Diabetes, vol. 51, Jun. 2002, pp. 1851-1858.
Baillie et al, J. Chem. Soc. (C) 1968, 48-52.
Bebernitz et al, "The Effect of 1,3-Diaryl-[1H]-pyrazole-4-acetamides on Glucose Utilization in ob/ob Mice," J. Med. Chem. 2001, 44, pp. 2601-2611.
Biochimica et Biophysica acta 1658 (2004) 80-88.
Boveris et al, "Superoxide anion production and trypanocidal action of naphthoquinones on Trypanosoma Cruzi," Comparative Biochemistry and Physiology, C: Comparative Pharmacology, 1978, vol. 61C92), pp. 327-329.
Cool et al, "Identification and Characterization of a Small Molecule AMPK Activator That Treats Key Components of Type 2 Diabetes and the Metabolic Syndrome," Cell Metabolism 3, Jun. 2006, pp. 403-416.
Cool et al, Supplemental Data for "Identification and Characterization of a Small Molecule AMPK Activator That Treats Key Components of Type 2 Diabetes and the Metabolic Syndrome," referenced on p. 414 of Cell Metabolism 3, Jun. 2006, 1 Page.
Cruz et al, "Effect of beta-lapachone on hydrogen peroxide production in *Trypanosoma cruzi*," Acta Tropica, 1978, vol. 35, pp. 35-40.
Curr. Biol. 10, 1247-1255, 2000.
Curr. Opin. Cell Biol. 15, 706-716, 2003.
Davis et al, "Nature of Action of Sitagliptin, The Dipeptidy Peptidase-V Inhibitor in Diabetic Animals," Indian J. Pharmacol. 42(4) Aug. 2010, pp. 229-233.
Diabetes 49, 896-903, 2000.
Diraison et al, Diabetes 53, S84-91, 2004.
Duffy et al, "Effects of Antidiabetic Drugs on Dipeptidyl Peptidase IV Activity: Nateglinide is an Inhibitor of DPP IV and Arguments the Antidiabetic Activity of Glucagon-Like Peptide-1," European Journal of Pharmacology, 568, 2007, pp. 278-286.
Endocr. Rev. 24, 78-90, 2003.
Feiser et al, J. Am. Chem. Soci. 49 (1927), 857.
Fong (Expert Opinion on Investigational Drugs (2004) 13:1203-1206).
Garcia-Ruiz et al, "Protein tryosine phosphatases are involved in the interferon resistance associated with insulin resistance in HepG2 cells and obese mice," JBC Papers, 2012, pp. 1-20.
Garcia-Ruiz et al, "Supplemental Table to Protein tryosine phosphatases are involved in the interferon resistance associated with insulin resistance in HepG2 cells and obese mice," referenced on p. 4 of JBC Papers, 2012, 1 page.
Genevieve et al, J. Biol. Chem. 279, 20767-74, 2004.
Goncalves et al, "Evaluation of the toxicity of 3-allyl-beta-lapachone against *Trypanosma cruzi* bloodstream forms," Molecular and Biochemical parasitoloty, 1980, vol. 1(3), pp. 167-176.
Green et al, "Inhibition of Dipeptidyl Peptidase-IV Activity by Metformin Enhances the Antidiabetic Effects of Glucagon-like Peptide-1," European Journal of Pharmacology, 547 (2006), pp. 192-199.
Green et al, "Novel Glucagon-Like Peptide-1 (GLP-1) Analog Val(8)GLP-1 Results in Significant Improvements of Glucose Tolerance and Pacreatice β-Cell Function after 3-Week Daily Administration in Obese Diabetic (ob/ob) Mice," J. Pharm. Exp. Thep. vol. 318, No. 2, 2006, pp. 914-921.
J. Appl. Physiol. 91, 1073-1083, 2001.
J. Appl. Physiol. 92, 2475-2482, 2002.
J. Biol. Chem. 277, 32571-32577, 2002.
J. Biol. Chem. 277, 3829-3835, 2002.
J. Biol. Chem. 278, 41970-41976, 2003.
Javier et al, Genes & Development. 2004.
Journal of clinical investigation 111, 303-312, 2003.
Kim et al, "Metformin Inhibits Hepatic Gluconeogenesis Though AMP-Activated Protein Kinase-Dependent Regulation of the Orphan Nuclear Receptor SHP," Diabetes, vol. 57, 2008, pp. 306-314.
Kosacka et al, "COMP-Angiopoietin-1 Recovers Molecular Biomarkers of Neuropathy and Improves Vascularisation in Sciatic Nerve of ob/ob Mice," PLoS One 7(3): 2012, e32881.
Kurundkar et al, "Effect of a Novel Biphenyl Compound, VMNS2e on ob/ob Mice," European Journal of Pharmacology, 650, 2011, pp. 472-478.
Lee et al, Diabetes Res. Clin. Pract. 42, 161-167, 1998.
Lee et al, Nature Medicine, Jun. 13, 2004.
Lin et al, "Metformin reverses fatty liver disease in obese, leptin-deficient mice," Nature Medicine, vol. 6, No. 8, Sep. 2000, pp. 998-1003.
Lindstrom, "The Physiology of Obese-Hyperglycemic Mice [ob/ob Mice]," TheScientificWorld Journal, 7, 2007, pp. 666-685.
Lopez et al, "Effect of the lipophilic o-naphthoquinone CG 10-248 on rat liver mitochondria structure and function," Biocell, 2002, vol. 26(2), pp. 237-245.
Meng et al, "Discovery of 6-(Aminomethyl)-5-(2,4-dichlorophenyl)-7-methylimidazo[1,2-a]pyrimidine-2-carboxamides as Potent, Selective Dipeptidyl Peptidase-4 (DPP4) Inhibitors," J. Med. Chem. 53, 2010, pp. 5620-5628.
Min et al, Am. J. Physiol. Gastrointest Liver Physiol 287, G1-6, 2004.
Mitochondria 74, 1188-1199, 2003.
Moritoh et al, "The Dipepitidyl Peptidase-4 Inhibitor Alogaliptin in Combination With Pioglitazone Improves glycemic Control, Lipid Profiles, and Increases Pancreatic Insulin Content in ob/ob Mice," European Journal of Pharmacology 602, 2009, pp. 448-454.
Moritoh, et al, "Chronic Administration of Voglibose, an a-Glucosidase Inhibitor, Increases Active Glucagon-Like Peptide-1 Levels by Increasing Its Secretion and Decreasing Dipeptidyl Peptidase-4 Activity in ob/ob Mice," The Journal of Pharmacology & Experimental Therapeutics, 329: 669-676, 2009.
Nair et al, Tetrahedron Lett. 42 (2001), 4549-4551.
Nandakumar et al, Progress in lipid research 42, 238-256, 2003.
Neil et al, Nature drug discovery. 3(April), 340, 2004.
Obesity Research vol. 12(8), 2004, 1197-1211.
O'Harte et al, "Antagonistic Effects of Two Novel GIP Analogs, (Hyp3)GIP and (Hyp3)GIPLys16PAL, on the Biological Actions of GIP and Longer-Term Effects in Diabetic ob/ob Mice," American Journal of Physiol Endocrinol Metab, 2007, pp. 2:E1674-E1674-E1682.
Pelleymounter et al, "Effects of the obese Gene Product on Body Weight Regulation in ob/ob Mice," Science, vol. 269, Jul. 28, 1995, pp. 540-543.
Peterson, et al, Science 300, 1140-1142, 2003.
Putman et al, J. Physiol. 551, 169-178, 2003.
Raynald et al, Am. J. Physiol. Endocrinol. Metab. 281, 1340, 2001.
Roger et al, Cell, 117, 145-151, 2004.
Schurmann et al, "The Dipeptidyl Peptidase-4 Inhibitor Linagliptin Attenuates Inflammation and Accelerates Epithelialization in Wounds of Diabetic ob/ob Mice," JPET Fast Forward, Published on Apr. 4, 2012 as DOI1124/jpet.111.191098, 36 Pages.
Snyder et al, Tetrahedron Letters 28 (1987), 3427-3430.
Takahashi et al, "A Novel Aminosterol Reverses Diabetes and Fatty Liver Disease in Obese Mice," Journal of Hepatology, 41 (2004), pp. 391-398.
Wei et al, "C1q/TNF-related Protein-12 (CTRP12), a Novel Adipokine That Improves Insulin Sensitivity and Glycemic Control in Mouse Models of Obesity and Diabetes," Journal of Biological Chemistry, vol. 287, No. 13, Mar. 23, 2012, pp. 10301-10315.
Wei et al, Supplemental Data for "C1q/TNF-related Protein-12 (CTRP12), a Novel Adipokine That Improves Insulin Sensitivity and

(56) References Cited

OTHER PUBLICATIONS

Glycemic Control in Mouse Models of Obesity and Diabetes," referenced on p. 10301, Journal of Biological Chemestry, vol. 287, No. 13, Mar. 23, 2012, 10 Pages.

Witte et al, "2-Phenyl-beta-lapachone can affect mitochondrial function by redox cycling mediated oxidation," Archives of Biochemistry and Biophysics, 2004, vol. 432, pp. 129-135.

Xu et al, "Preventing b-Cell Loss and Diabetes With Calcium Channel Blockers," Diabetes, vol. 61, Apr. 2012, pp. 848-856.

Xu et al, Supplemental Data for "Preventing b-Cell Loss and Diabetes With Calcium Channel Blockers," referenced on p. 848 of Diabetes, vol. 61, Apr. 2012, 4 Pages.

Zhang et al, "Synthesis and evaluation of piperidine urea derivatives as efficacious 11b-hydroxysteroid dehydrogenase type 1 inhibitors in diabetic ob/ob mice," Bioorganic & Medicinal Chemistry Letters, 22, 2012, pp. 2748-2752.

Zhang et al, Supplemental Data for "Synthesis and evaluation of piperidine urea derivatives as efficacious 11b-hydroxysteroid dehydrogenase type 1 inhibitors in diabetic ob/ob mice," referenced on p. 2752 of Bioorganic & Medicinal Chemistry Letters, 22, 2012, 9 Pages.

Zing-Ping et al, FEES Letters 443, 285-289, 1999.

Zong et al, Proc Nat'l. Acad. Sci. USA 99: 15983-15987, 2002.

\* cited by examiner

A

Untreated    Vehicle    β-lapachone

Vehicle	β-lapachone

Vehicle	β-lapachone

PHARMACEUTICAL COMPOSITION FOR THE TREATMENT OR PREVENTION OF DISEASES INVOLVING OBESITY, DIABETES, METABOLIC SYNDROME, NEURO-DEGENERATIVE DISEASES AND MITOCHONDRIA DYSFUNCTION DISEASES

This application is a Continuation application of co-pending U.S. application Ser. No. 12/470,514, filed May 22, 2009, which is a Continuation application of U.S. application Ser. No. 11/816,438, filed Aug. 16, 2007. U.S. application Ser. No. 11/816,438 is the national stage application of PCT/KR2006/000531, filed Feb. 15, 2006, which claims priority to Korean Patent Application No. 10-2005-0012625, filed Feb. 16, 2005, the contents all of which in their entirety are herein incorporated by reference.

FIELD OF THE INVENTION

The present invention relates to a pharmaceutical composition for the treatment and/or prevention of various diseases involving obesity, diabetes, metabolic syndromes, degenerative diseases and mitochondrial dysfunction-related diseases.

BACKGROUND OF THE INVENTION

Obesity, a condition in which an amount of body fat is abnormally higher than standard body weight, refers to a disease resulting from accumulation of surplus calories in adipose tissues of the body when calorie intake is greater than calorie expenditure. Complications caused from obesity include, for example hypertension, myocardiac infarction, varicosis, pulmonary embolism, coronary artery diseases, cerebral hemorrhage, senile dementia, Parkinson's disease, type 2 diabetes, hyperlipidemia, cerebral apoplexy, various cancers (such as uterine cancer, breast cancer, prostate cancer, colon cancer and the like), heart diseases, gall bladder diseases, sleep apnea syndrome, arthritis, infertility, venous ulcer, sudden death, fatty liver, hypertrophic cardiomyopathy (HCM), thromboembolism, esophagitis, abdominal wall hernia (Ventral Hernia), urinary incontinence, cardiovascular diseases, endocrine diseases and the like (Obesity Research Vol. 12(8), 2004, 1197-1211).

Diabetes is a systemic metabolic disorder resulting from multiple environmental and genetic factors, and refers to a condition characterized by abnormally elevated blood glucose levels due to absolute or relative deficiency of insulin in the body. Complications of diabetes includes, for example hypoglycemia, ketoacidosis, hyperosmolar coma, macrovascular complications, diabetic retinopathy, diabetic neuropathy, diabetic nephropathy and the like.

Metabolic syndromes refer to syndromes accompanied by health risk factors such as hypertriglyceridemia, hypertension, glycometabolism disorders, blood coagulation disorders and obesity. According to the ATP III criteria of the National Cholesterol Education Program (NCEP) published in 2001, individuals are diagnosed with the metabolic syndrome by the presence of three or more of the following components: 1) A waistline of 40 inches (102 cm) or more for men and 35 inches (88 cm) or more for women (central obesity as measured by waist circumference), 2) A triglyceride level above 150 mg/dl, 3) A high density lipoprotein level (HDL) less than 40 mg/dl (men) or under 50 mg/dl (women), 4) A blood pressure of 130/85 mm Hg or higher and 5) A fasting blood glucose level greater than 110 mg/dl.

Insulin resistance refers to a phenomenon wherein, even though insulin is normally secreted in the body, "supply of glucose into cells" performed by insulin does not work properly. Therefore, glucose in the blood cannot enter cells, thus causing hyperglycemia, and further, cells themselves cannot perform normal functions thereof due to a shortage of glucose, leading to the manifestation of metabolic syndrome.

The degenerative disease is the term derived from pathological findings, thus meaning the condition which is accompanied by "decreases in consumption of oxygen", and refers to a degenerative disease wherein dysfunction of mitochondria, which is an organelle that generates energy using oxygen within the cell, is related to senescence. As examples of the degenerative disease, mention may be made of neurodegenerative disease such as Alzheimer's disease, Parkinson's disease and Huntington's disease (Korean Society of Medical Biochemistry and Molecular Biology News, 2004, 11(2), 16-22).

Diseases arising from mitochondrial dysfunction may include for example, mitochondrial swelling due to mitochondrial membrane potential malfunction, functional disorders due to oxidative stress such as by the action of active oxygen species or free radicals, functional disorders due to genetic factors, and diseases due to functional deficiency of oxidative phosphorylation mechanisms for energy production of mitochondria. Specific examples of diseases, developed by the above-mentioned pathological causes, may include multiple sclerosis, encephalomyelitis, cerebral radiculitis, peripheral neuropathy, Reye's syndrome, Friedrich's ataxia, Alpers syndrome, MELAS, migraine, psychosis, depression, seizure and dementia, paralytic episode, optic atrophy, optic neuropathy, retinitis pigmentosa, cataract, hyperaldosteronemia, hypoparathyroidism, myopathy, amyotrophy, myoglobinuria, hypotonia, myalgia, the decrease of exercise tolerance, renal tubulopathy, renal failure, hepatic failure, liver function failure, hepatomegaly, red blood cell anemia (iron-deficiency anemia), neutropenia, thrombocytopenia, diarrhea, villous atrophy, multiple vomiting, dysphagia, constipation, sensorineural hearing loss (SNHL), epilepsy, mental retardation, Alzheimer's disease, Parkinson's disease and Huntington's disease (see, for example U.S. Pat. No. 6,183,948, Korean Patent Laid-open Publication No. 2004-7005109, Journal of clinical investigation 111, 303-312, 2003, Mitochondria 74, 1188-1199, 2003, Biochimica et Biophysica acta 1658 (2004) 80-88).

The above-mentioned obesity, diabetes, metabolic syndromes, degenerative diseases and mitochondrial dysfunction-related diseases will be collectively referred to as "disease syndromes" hereinafter.

At present, the most effective way to ameliorate or fight against the conditions associated with such disease syndromes is known to be getting more exercise and losing weight, and dietary control. All of the currently effective ways of fighting against the disease syndromes have in common the fact that they facilitate energy metabolism, thus resulting in maximized expenditure of surplus energy in the body leading to prevention of energy accumulation. Effective expenditure of such surplus energy is considered a method for treating the disease syndromes. Promoting energy metabolism is most important for effective elimination of surplus energy. For this purpose, it is essential to achieve inhibition of lipogenesis, inhibition of gluconeogenesis, facilitation of glucose consumption, facilitation of fat oxidation, facilitation of biogenesis of mitochondria which is a central apparatus of energy metabolism and collective activation of factors involved in metabolic activation.

There is yet little known about targets to treat the disease-syndromes, whereas numerous target proteins or genes are known only for treating individual diseases and therefore there have been proposed some methods for the prevention or treatment of such diseases via use of the above-mentioned corresponding target proteins or genes. However, there is still a room for further significant improvement even in treatment of individual diseases such as metabolic syndromes including obesity, diabetes and the like. In spite of the fact that a great deal of studies have been conducted on treatment of diseases, there are yet no drugs available for the treatment of various diseases resulting from excess energy intake and aging.

Most of diseases including obesity, diabetes, metabolic syndromes, degenerative diseases and mitochondrial dysfunction-related diseases, i.e., large numbers of diseases including disease syndromes, stem from imbalance of energy metabolism and oxidation-reduction state. For this reason, the present invention has also employed a method of confirming the presence/absence of activation effects on AMP-activated protein kinase (AMPK), as the most fundamental primary test to confirm biological efficacy of compounds of interest on disease syndromes.

Meanwhile, once AMPK is activated, a variety of physiological events are consequently affected in the downstream of the mechanism thereof. In this regard, factors to be regulated and expression phenomena are provided as follows.

1. Glycometabolism

In muscle tissues and myocardial tissues, AMPK promotes muscle contraction and thereby facilitates intake of glucose. That is, AMPK activates GLUT 1, or induces migration of GLUT 4 to a plasma membrane, regardless of insulin action, resulting in increased glucose uptake into cells (Arch. Biochem. Biophys. 380, 347-352, 2000, J. Appl. Physiol. 91, 1073-1083, 2001). After increasing glucose uptake into cells, AMPK activates hexokinase, thereby increasing flux of glycometabolism processes and simultaneously inhibiting glycogen synthesis. It is known that in myocardial tissues under ischemic conditions, AMPK activates a phosphorylation process of 6-phosphofructo-2-kinase (PFK-2), with consequent activation of a metabolic cascade leading to increased flux of glycometabolism (Curr. Biol. 10, 1247-1255, 2000). In addition, it was confirmed that activation of AMPK in the liver inhibits release of glucose from hepatocytes, and activity of phosphoenolpyruvate carboxykinase (PEPCK) and glucose-6-phosphatase, which are gluconeogenesis enzymes, is inhibited by AMPK (Diabetes 49, 896-903, 2000). This is because AMPK independently takes part in regulation of a blood glucose level via inhibition of release of glucose from the liver, irrespective of insulin.

2. Mitochondrial Biogenesis

One important function of mitochondria is to carry out an oxidative phosphorylation process, which converts energy produced from fuel metabolites such as glucose and fatty acids into ATP. It is known that the incidence of disorders in mitochondrial functions is involved in a pathogenic mechanism of various degenerative diseases associated with senescence, such as diabetes, cardiovascular diseases, Parkinson's disease and senile dementia (Curr. Opin. Cell Biol. 15, 706-716, 2003). Peterson, et al (Science 300, 1140-1142, 2003) have suggested the possibility that deteriorated mitochondrial function is a probable pathogenic cause of insulin resistance syndrome, with reporting that oxidative phosphorylation functions of mitochondria were weakened by about 40% in the elderly. Lee, et al (Diabetes Res. Clin. Pract. 42, 161-167, 1998) have confirmed that a decrease in the content of mitochondrial DNA in the peripheral blood is initiated from before the incidence of diabetes. Biogenesis of mitochondria in muscles is known to be promoted by an adaptive reaction in which metabolic activity of oxidative phosphorylation of muscle cells is increased by chronic energy depletion and exercise. Zong, et al (Proc Natl. Acad. Sci. USA 99: 15983-15987, 2002) have revealed that, using a transgenic mouse in which AMPK was genetically inactivated, AMPK is required for mitochondrial biogenesis in skeletal muscle under conditions in which chronic energy deprivation was induced. Further, Putman, et al (J. Physiol. 551, 169-178, 2003) have demonstrated the hypothesis that AMPK in association with continuous exercise is involved in an increase of mitochondrial volume.

Meanwhile, it was confirmed that AMPK increases gene expression of a peroxisome proliferator-activated receptor gamma coactivator 1α(PGC-1α) which is known to play an important role in mitochondrial biogenesis (Endocr. Rev. 24, 78-90, 2003). Raynald, et al (Am. J. Physiol. Endocrinol. Metab. 281, 1340, 2001) have suggested that a nuclear respiratory factor-1 (NRF-1), which is a gene essential for transcription of proteins associated with a mitochondrial respiratory system as well as mitochondrial transcription and replication, plays an important role to increase oxidation capability in muscle cells in response to chronic energy stress. Therefore, NRF-1 consequently participates in an increase of mitochondrial biogenesis. In addition, it is known that enzymatic activity of citrate synthase and 3-hydroxyacyl-CoA dehydrogenase, known as being increased in conjunction with increased amounts of UCP-3 protein and mRNA thereof and increased mitochondrial volume, is increased by activation of AMPK (J. Physiol. 551, 169-178, 2003).

3. Fat Metabolism Regulation and AMPK

Upon reviewing a mechanism of AMPK participating in fat metabolism, AMPK induces phosphorylation of acetyl-CoA carboxylase, thereby resulting in inhibition of fatty acid synthesis. Therefore, AMPK is known to facilitate fatty acid oxidation, by the action of decreasing an intracellular concentration of malonyl-CoA that is an intermediate of fatty acid synthesis and is an inhibitor of carnitine palmitoyl-CoA transferase I (CPT I). CPT I is an enzyme essential for a fatty acid oxidation process wherein fatty acids enter mitochondria and are oxidized, and is known under the control of malonyl-CoA. In addition, AMPK is known to inhibit activity of HMG-CoA reductase and glycerol phosphate acyl transferase (GPAT), involved in synthesis of cholesterol and triacylglycerol, through phosphorylation (J. Biol. Chem. 277, 32571-32577, 2002, J. Appl. Physiol. 92, 2475-2482, 2002).

Meanwhile, it was found that activation of AMPK in the liver inhibits the activity of pyruvate kinase, fatty acid synthase and ACC through phosphorylation of carbohydrate-response-element-binding protein (ChREBP) (J. Biol. Chem. 277, 3829-3835, 2002). In addition, activity of sterol-regulatory-element binding protein-1 (SREBP-1), which plays an important role in differentiation of adipocytes, is also inhibited by the action of AMPK, which results then in inhibition of adipocyte differentiation.

4. Protein Synthesis Regulation and AMPK

In the protein synthesis process, AMPK inhibits synthesis of proteins via inhibition of mTOR and p70S6K by activating TSC, or AMPK inhibits translation elongation via activation of elongation factor-2 (eEF2) kinase and inactivation of eEF2 through phosphorylation thereof. It was found that eEF2 kinase is a direct substrate for AMPK (J. Biol. Chem. 278, 41970-41976, 2003).

As discussed above, AMPK is known to play a central role in energy metabolism of glucose, protein and fat in vitro and in vivo. Neil, et al (Nature drug discovery, 3(April), 340, 2004) has asserted that AMPK and Malonyl-CoA are possible targets for the treatment of metabolic syndromes, and they have also stated that patients suffering from metabolic syndromes can be characterized by insulin resistance, obesity, hypertension, dyslipidemia, and dysfunction of pancreatic beta cells, type II diabetes and manifestation of arteriosclerosis. It was hypothesized that a common feature linking these multiple abnormalities is dysregulation of AMPK/Malonyl-CoA energy level-sensing and signaling network. It was proposed that such dysregulation leads to alterations in cellular fatty-acid metabolism that in turn cause abnormal fat accumulation, cellular dysfunction and ultimately disease. Evidence is also presented that factors activating AMPK and/or reducing malonyl-CoA levels might reverse these abnormalities and syndromes or prevent incidence of these diseases.

Roger, et al (Cell, 117, 145-151, 2004) have suggested that AMPK may be a possible target to control obesity by lowering activity of hypothalamic AMPK, thereby increasing a content of malonyl-CoA and then regulating appetite for food intake.

Lee, et al (Nature medicine, 13 Jun. 2004) have suggested that alpha-lipoic acid can exert anti-obesity effects by suppressing hypothalamic AMPK activity, thus controlling appetite. They have also reported that alpha-lipoic acid promotes fat metabolism via activation of AMPK in muscle tissues, not hypothalamus, and alpha-lipoic acid is therapeutically effective for the treatment of obesity because it facilitates energy expenditure by activating UCP-1, particularly in adipocytes.

Diraison, et al (Diabetes 53, S84-91, 2004) have reported that activation of AMPK in pancreatic cells leads to four-fold increases in expression of the gut hormone peptide YY responsible for appetite control and thus appetite can be regulated by the action of AMPK in other tissues other than hypothalamus.

Nandakumar, et al (Progress in lipid research 42, 238-256, 2003) have proposed that, in ischemic heart diseases, AMPK would be a target to treat ischemia reperfusion injuries via regulation of fat and glucose metabolism.

Min, et al (Am. J. Physiol. Gastrointest Liver Physiol 287, G1-6, 2004) have reported that AMPK is effective for regulation of alcoholic fatty liver.

Genevieve, et al (J. Biol. Chem. 279, 20767-74, 2004) have reported that activation of AMPK inhibits activity of an iNOS enzyme that is an inflammation mediator in chronic inflammatory conditions or endotoxin shock, including obesity-related diabetes and thus AMPK will be effective for developing new medicines having a mechanism capable of enhancing insulin sensitivity. In addition, they have reported that inhibition of iNOS activity is effected by activation of AMPK, and thus this finding is clinically applicable to diseases such as septicemia, multiple sclerosis, myocardial infarction, inflammatory bowel diseases and pancreatic beta-cell dysfunction.

Zing-ping et al (FEBS Letters 443, 285-289, 1999) have reported that AMPK activates endothelial NO synthase through phosphorylation, in the presence of Ca-calmodulin in murine muscle cells and myocardial cells. This represents that AMPK is implicated in heart diseases including angina pectoris.

Javier, et al (Genes & Develop. 2004) have reported that a lifespan can be extended by limiting utilization of energy and such a prolonged lifespan is achieved in a manner that an in vivo AMP/ATP ratio is increased and therefore the α2 subunit of AMPK is activated by AMP. Therefore, they have suggested that AMPK may function as a sensor to detect the relationship between lifespan extension and energy level and insulin-like signal information.

Meanwhile, Danshen (*Salvia miltiorrhiza*) has been widely used as an important herbal medicine in Northeast Asia regions since ancient times, and is well-known to have excellent effects on prevention and treatment of various cardiovascular diseases. Upon focusing our attention to such therapeutic efficacy of Danshen, the inventors of the present invention have suggested that main ingredients of Danshen are superb medicinal substances capable of treating various diseases such as obesity, diabetes and metabolic syndromes. For example, see Korean Patent Nos. 2003-0099556, 2003-0099557, 2003-0099657, 2003-0099658, 2004-0036195, 2004-0036197 and 2004-0050200, assigned to the present applicant. In particular, the present inventors have revealed that main principles of Danshen including Cryptotanshinone, 15,16-Dihydrotanshinone, Tanshinone II-A, and Tanshinone I can treat metabolic syndrome diseases.

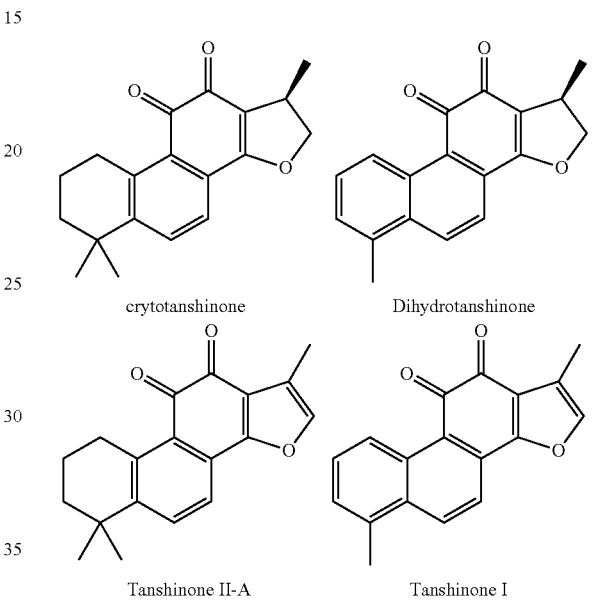

crytotanshinone    Dihydrotanshinone

Tanshinone II-A    Tanshinone I

SUMMARY OF THE INVENTION

As a result of a variety of extensive and intensive studies and experiments based on the facts as described above, the inventors of the present invention have newly confirmed that naphthoquinone-based compounds such as β-lapachone {7,8-dihydro-2,2-dimethyl-2H-naphtho(2,3-b)dihydropyran-7,8-dione}, dunnione {2,3,3-tirmethyl-2,3,4,5-tetrahydro-naphtho(2,3-b)dihydrofuran-6,7-dione}, α-dunnione {2,3,3-tirmethyl-2,3,4,5-tetrahydro-naphtho(2,3-b)dihydrofuran-6,7-dione}, nocardinone A, nocardinone B, lantalucratin A, lantalucratin B and lantalucratin C can also be used in the prevention or treatment of various diseases such as obesity, diabetes, metabolic syndromes, degenerative diseases and diseases associated with mitochondrial dysfunction.

β-lapachone is a naturally occurring plant product derived from lapachol (a naphthoquinone) obtained from the lapacho tree (*Tabebuia avellanedae*) which is native to South America. Dunnione and α-dunnione are also obtained from the leaves of *Streptocarpus dunnii* native to South America. Since ancient times in South America, these natural tricyclic naphthoquinone derivatives have been widely used as an anti-cancer drug and in the treatment of Chagas disease which is typically endemic in South America, and are also known to exert excellent therapeutic effects. In particular, as their pharmacological actions as the anti-cancer drug are generally known to western countries, these tricyclic naphthoquinone derivatives have lately attracted considerable attention from people. In fact, as disclosed in U.S. Pat. No. 5,969,163, such tricyclic naphthoquinone derivative compounds are currently developed as a variety of anti-cancer drugs by many research groups and institutions.

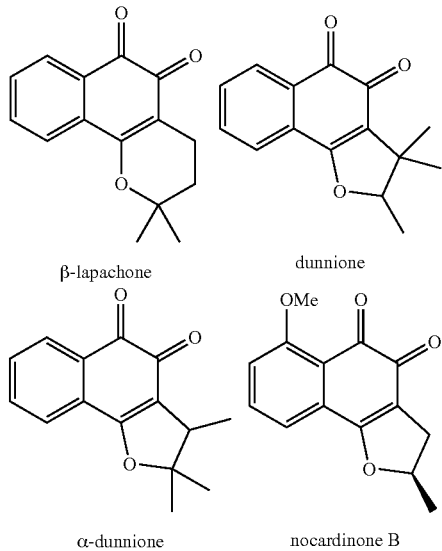

β-lapachone dunnione

α-dunnione nocardinone B

However, despite a variety of researches and studies, it still remains unknown the fact that such naphthoquinone compounds have therapeutic efficacy for treating or preventing obesity, diabetes, metabolic syndromes, degenerative diseases and diseases associated with mitochondrial dysfunction.

Based on the fact that the above-mentioned naphthoquinone compounds such as β-lapachone, dunnione, α-dunnione, nocardinone A, nocardinone B, lantalucratin A, lantalucratin B and lantalucratin C have chemical basic structures similar to those of Tanshinone derivatives extracted from Danshen, the inventors of the present invention have investigated their pharmacological actions as therapeutic and prophylactic agents for metabolic syndromes. That is, the present inventor have attempted to examine whether naphthoquinone compounds as disclosed in the present invention activate AMPK in cells and tissues. Then, in order to examine profoundly therapeutic effects of the compounds for "disease syndromes" including obesity, diabetes, metabolic syndromes, degenerative diseases and mitochondrial dysfunction-related diseases based on results thus obtained, the present inventor have examined therapeutic effects for the treatment and/or prevention of disease syndromes including obesity, diabetes and metabolic syndromes, through various experiments using ob/ob mice, a animal model of obesity caused by decreased secretion of leptin. Consequently, the present inventors have confirmed that the naphthoquinone compounds in accordance with the present invention have excellent effects on the treatment and/or prevention of disease syndromes. The present invention has been completed based on these findings.

Therefore, an object of the present invention is to provide a pharmaceutical composition comprising, as an active ingredient, a naphthoquinone compound which is therapeutically effective for the treatment and prevention of disease syndromes such as obesity, diabetes, metabolic syndromes, degenerative diseases and mitochondrial dysfunction-related diseases.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF PREFERRED EMBODIMENTS

Figure 1:
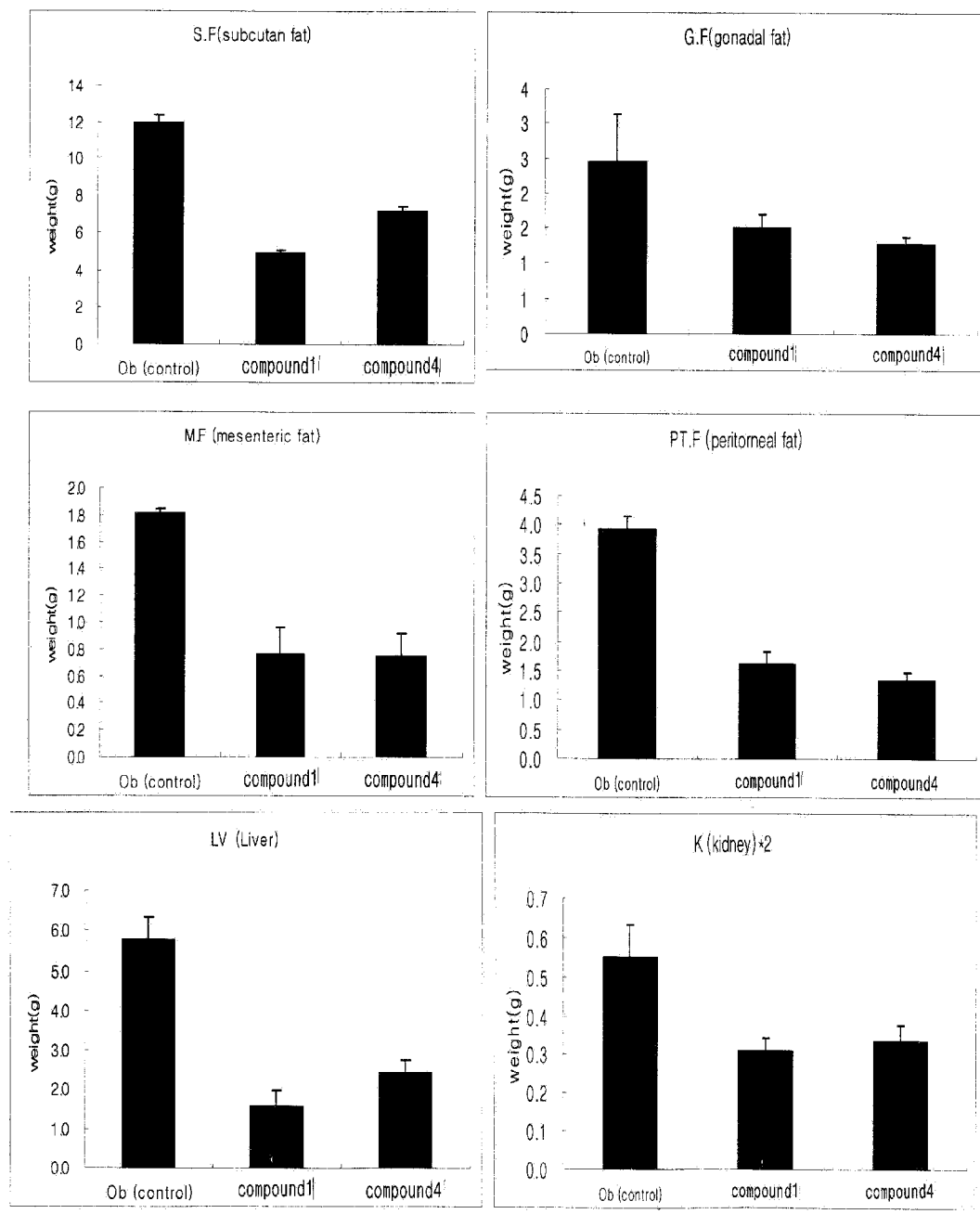
FIGS. 1 through 3 are graphs showing fat distribution in terms of numerical values according to each organ of C57BL/6JL Lep ob/Lep ob mice which were administered with a pharmaceutical composition in accordance with the present invention.

In accordance with an aspect of the present invention, the above and other objects can be accomplished by the provision of a pharmaceutical composition for the treatment and/or prevention of disease syndromes such as obesity, diabetes, metabolic syndromes, degenerative diseases and mitochondrial dysfunction-related diseases, comprising: (a) a therapeutically effective amount of a compound represented by Formula I below:

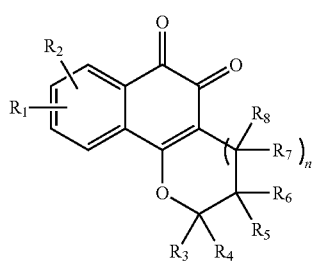

(I)

wherein $R_1$ and $R_2$ are each independently hydrogen, halogen, alkoxy, hydroxy or lower alkyl having 1 to 6 carbon atoms;

$R_3$, $R_4$, $R_5$, $R_6$, $R_7$ and $R_8$ are each independently hydrogen, hydroxy, $C_1$-$C_{20}$ alkyl, alkene or alkoxy, cycloalkyl, heterocycloalkyl, aryl or heteroaryl, or two substituents of $R_3$ to $R_8$ may be taken together to form a cyclic structure which may be saturated or partially or completely unsaturated; and n is 0 or 1, with proviso that when n is 0, carbon atoms adjacent to n form a cyclic structure via a direct bond; or a pharmaceutically acceptable salt, prodrug, solvate or isomer thereof, and (b) a pharmaceutically acceptable carrier, a diluent or an excipient, or any combination thereof.

In order to confirm therapeutic and prophylactic effects of the compound of Formula I on disease syndromes, the present inventors, as will be illustrated in Experimental Examples hereinafter, have measured activity of the compound of Formula I on AMPK activity in myoblast cells (C2C12) and suppression of cellular differentiation in preadipocytes (3T3-L1 and F442A cells) and as a result, have confirmed that such a compound exhibits superior AMPK activation effects and inhibitory effects of adipocyte differentiation.

In addition, the present inventors have further confirmed that therapeutic and prophylactic effects of disease syndromes by the compound of Formula I were examined through in vivo experiments using ob/ob mice, a model of obesity, db/db mice, a model of obesity/diabetes, DIO (diet-induced obesity) mice, caused by high fat dietary conditions, and Zucker fa/fa rats, a model of obesity/diabetes, and as a result, the compound of Formula I was highly therapeutically effective.

Therefore, it is expected that the pharmaceutical composition in accordance with the present invention, comprising the compound of Formula I as an active ingredient, can treat and prevent a variety of disease syndromes as defined in the present invention via activation of AMPK.

As used herein, the term "pharmaceutically acceptable salt" means a formulation of a compound that does not cause significant irritation to an organism to which it is administered and does not abrogate the biological activity and properties of the compound. Examples of the pharmaceutical salt may include acid addition salts of the compound (I) with acids capable of forming a non-toxic acid addition salt containing pharmaceutically acceptable anions, for example, inorganic acids such as hydrochloric acid, sulfuric acid, nitric acid, phosphoric acid, hydrobromic acid and hydroiodic acid; organic carbonic acids such as tartaric acid, formic acid, citric acid, acetic acid, trichloroacetic acid, trifluoroacetic acid, gluconic acid, benzoic acid, lactic acid, fumaric acid, maleic acid and salicylic acid; or sulfonic acids such as methanesulfonic acid, ethanesulfonic acid, benzenesulfonic acid and p-toluenesulfonic acid. Specifically, examples of pharmaceutically acceptable carboxylic acid salts include salts with alkali metals or alkaline earth metals such as lithium, sodium, potassium, calcium and magnesium, salts with amino acids such as arginine, lysine and guanidine, salts with organic bases such as dicyclohexylamine, N-methyl-D-glutamine, tris(hydroxymethyl)methylamine, diethanoamine, choline and triethylamine. The compound of Formula I in accordance with the present invention may be converted into salts thereof, by conventional methods well-known in the art.

As used herein, the term "prodrug" means an agent that is converted into the parent drug in vivo. Prodrugs are often useful because, in some situations, they may be easier to administer than the parent drug. They may, for instance, be bioavailable by oral administration, whereas the parent may be not. The prodrugs may also have improved solubility in pharmaceutical compositions over the parent drug. An example of a prodrug, without limitation, would be a compound of the present invention which is administered as an ester (the "prodrug") to facilitate transport across a cell membrane where water-solubility is detrimental to mobility, but which then is metabolically hydrolyzed to the carboxylic acid, the active entity, once inside the cell where water-solubility is beneficial. A further example of the prodrug might be a short peptide (polyamino acid) bonded to an acidic group, where the peptide is metabolized to reveal the active moiety.

As used herein, the term "solvate" means a compound of the present invention or a salt thereof, which further includes a stoichiometric or non-stoichiometric amount of a solvent bound thereto by non-covalent intermolecular forces. Preferred solvents are volatile, non-toxic, and/or acceptable for administration to humans. Where the solvent is water, the solvate refers to a hydrate.

As used herein, the term "isomer" means a compound of the present invention or a salt thereof, that has the same chemical formula or molecular formula but is optically or sterically different therefrom.

Unless otherwise specified, the term "compound of Formula I" is intended to encompass a compound per se, and a pharmaceutically acceptable salt, prodrug, solvate and isomer thereof.

As used herein, the term "alkyl" refers to an aliphatic hydrocarbon group. The alkyl moiety may be a "saturated alkyl" group, which means that it does not contain any alkene or alkyne moieties. Alternatively, the alkyl moiety may also be an "unsaturated alkyl" moiety, which means that it contains at least one alkene or alkyne moiety. The term "alkene"

moiety refers to a group in which at least two carbon atoms form at least one carbon-carbon double bond, and an "alkyne" moiety refers to a group in which at least two carbon atoms form at least one carbon-carbon triple bond. The alkyl moiety, regardless of whether it is substituted or unsubstituted, may be branched, linear or cyclic.

As used herein, the term "heterocycloalkyl" means a carbocyclic group in which one or more ring carbon atoms are substituted with oxygen, nitrogen or sulfur and which includes, for example, but is not limited to furan, thiophene, pyrrole, pyrroline, pyrrolidine, oxazole, thiazole, imidazole, imidazoline, imidazolidine, pyrazole, pyrazoline, pyrazolidine, isothiazole, triazole, thiadiazole, pyran, pyridine, piperidine, morpholine, thiomorpholine, pyridazine, pyrimidine, pyrazine, piperazine and triazine.

As used herein, the term "aryl" refers to an aromatic substituent group which has at least one ring having a conjugated pi ($\pi$) electron system and includes both carbocyclic aryl (for example, phenyl) and heterocyclic aryl (for example, pyridine) groups. This term includes monocyclic or fused-ring polycyclic (i.e., rings which share adjacent pairs of carbon atoms) groups.

As used herein, the term "heteroaryl" refers to an aromatic group that contains at least one heterocyclic ring.

Examples of aryl or heteroaryl include, but are not limited to, phenyl, furan, pyran, pyridyl, pyrimidyl and triazyl.

$R_1$, $R_2$, $R_3$, $R_4$, $R_5$, $R_6$, $R_7$ and $R_8$ in Formula I in accordance with the present invention may be optionally substituted. When substituted, the substituent group(s) is(are) one or more group(s) individually and independently selected from cycloalkyl, aryl, heteroaryl, heteroalicyclic, hydroxy, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino including mono- and di-substituted amino, and protected derivatives thereof.

Among compounds of Formula I, preferred are compounds of Formulae II through IV below.

Compounds of Formula II are compounds wherein n is 0 and adjacent carbon atoms form a cyclic structure (furan ring) via a direct bond therebetween and are often referred to as "furan compounds" or "furano-o-naphthoquinone derivatives" hereinafter.

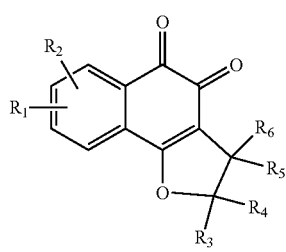

(II)

Compounds of Formula III are compounds wherein n is 1 and are often referred to as "pyran compounds" or "pyrano-o-naphthoquinone" hereinafter.

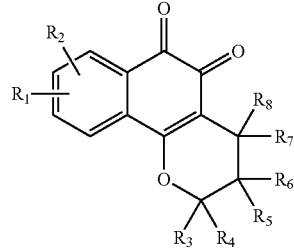

(III)

In Formula I, each $R_1$ and $R_2$ is particularly preferably hydrogen.

Among the furan compounds of Formula II, particularly preferred are compounds of Formula IIa wherein $R_1$, $R_2$ and $R_4$ are independently hydrogen, or compounds of Formula IIb wherein $R_1$, $R_2$ and $R_6$ are independently hydrogen.

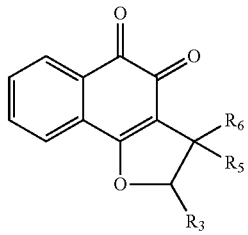

(IIa)

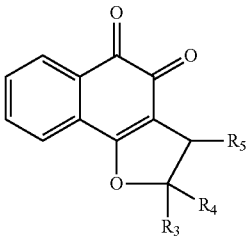

(IIb)

Further, among the pyran compounds of Formula III, particularly preferred are compounds of Formula IIIa wherein $R_1$, $R_2$, $R_5$, $R_6$, $R_7$ and $R_8$ are independently hydrogen.

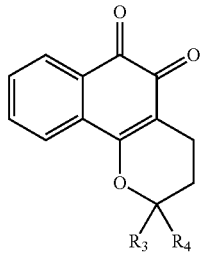

(IIIa)

The term "pharmaceutical composition" as used herein means a mixture of a compound of Formula I with other chemical components, such as diluents or carriers. The pharmaceutical composition facilitates administration of the compound to an organism. Various techniques of administering a compound are known in the art and include, but are not limited to oral, injection, aerosol, parenteral and topical administrations. Pharmaceutical compositions can also be obtained by reacting compounds of interest with acids such as hydrochloric acid, hydrobromic acid, sulfuric acid, nitric acid, phosphoric acid, methanesulfonic acid, p-toluenesulfonic acid, salicylic acid and the like.

The term "therapeutically effective amount" means an amount of an active ingredient that is effective to relieve or reduce to some extent one or more of the symptoms of the disease in need of treatment, or to retard initiation of clinical markers or symptoms of a disease in need of prevention, when the compound is administered. Thus, a therapeutically effective amount refers to an amount of the active ingredient which exhibit effects of (i) reversing the rate of progress of a disease; (ii) inhibiting to some extent further progress of the disease; and/or, (iii) relieving to some extent (or, preferably, eliminating) one or more symptoms associated with the disease. The therapeutically effective amount may be empirically determined by experimenting with the compounds concerned in known in vivo and in vitro model systems for a disease in need of treatment.

The term "carrier" means a chemical compound that facilitates the incorporation of a compound into cells or tissues. For example, dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffer solution is phosphate buffered saline (PBS) because it mimics the ionic strength conditions of human body fluid. Since buffer salts can control the pH of a solution at low concentrations, a buffer diluent rarely modifies the biological activity of a compound.

The compounds described herein may be administered to a human patient per se, or in the form of pharmaceutical compositions in which they are mixed with other active ingredients, as in combination therapy, or suitable carriers or excipient(s). Techniques for formulation and administration of the compounds may be found in "Remington's Pharmaceutical Sciences," Mack Publishing Co., Easton, Pa., 18th edition, 1990.

In the pharmaceutical composition in accordance with the present invention, compounds of Formula I, as will be illustrated hereinafter, can be prepared by conventional methods known in the art and/or various processes which are based upon the general technologies and practices in the organic chemistry synthesis field. The preparation processes described below are only exemplary ones and other processes can also be employed. As such, the scope of the instant invention is not limited to the following processes.

Preparation Method 1: Synthesis of Lapachol Derivative and Acid-Catalyzed Cyclization β-lapachone is obtained in a relatively small amount from the lapacho tree, whereas lapachol, used as a raw material for synthesis of β-lapachone, is obtained in a considerably large amount from the lapacho tree. Therefore, a process for synthesis of β-lapachone utilizing lapachol was already developed long time ago. That is, as taught by L. F. Fieser in J. Am. Chem. Scoc. 49 (1927), 857, β-lapachone is obtained in a relatively high yield by mixing lapachol and sulfuric acid and vigorously stirring the resulting mixture at room temperature. As such, tricyclic naphthoquinone (pyrano-o-naphthoquinone and furano-o-naphthoquinone) derivatives having a relatively simple chemical structure are generally synthesized in a relatively high yield via cyclization using sulfuric acid as a catalyst, as in Reaction scheme below. Based on this process, a variety of compounds of Formula I can be synthesized.

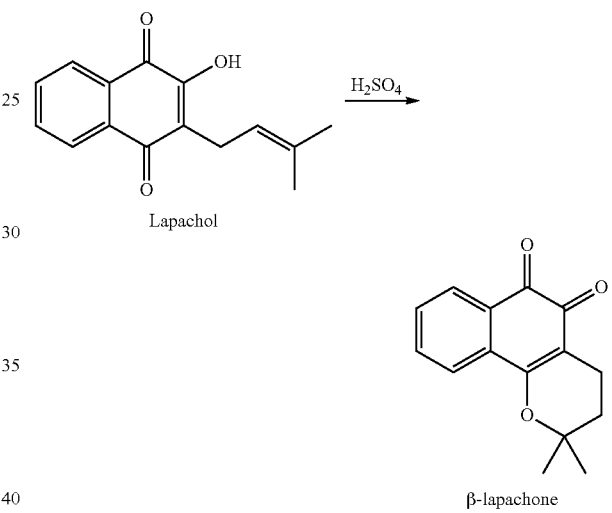

More specifically, the above synthesis process may be summarized as follows.

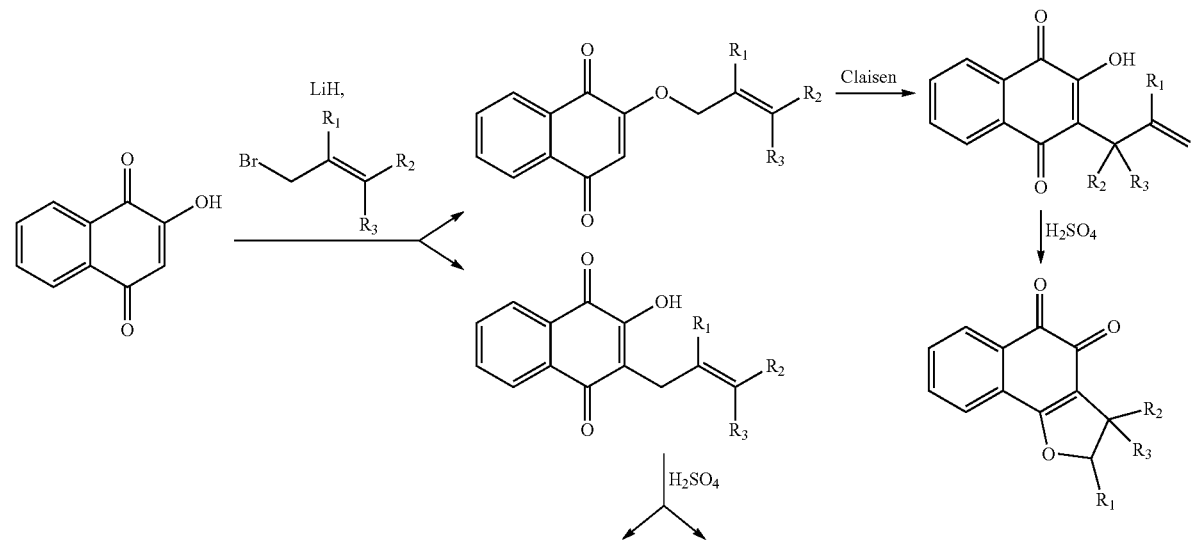

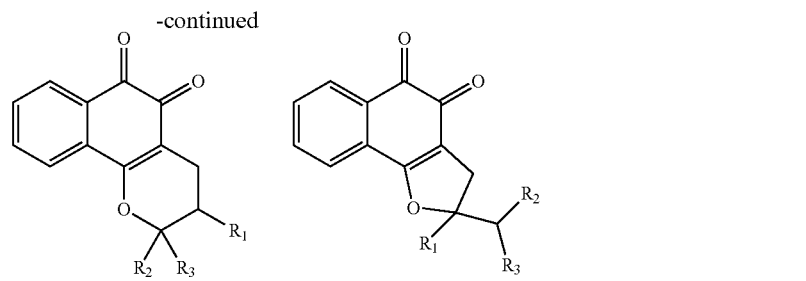

That is, when 2-hydroxy-1,4-naphthoquinone is reacted with various allylic bromides or equivalents thereof in the presence of a base, a C-alkylation product and an O-alkylation product are concurrently obtained. It is also possible to synthesize either of two derivatives only depending upon reaction conditions. Since O-alkylated derivative is converted into another type of C-alkylated derivative through Claisen Rearrangement by refluxing the O-alkylated derivative using a solvent such as toluene or xylene, it is possible to obtain various types of 3-substituted-2-hydroxy-1,4-naphthoquinone derivatives. The various types of C-alkylated derivatives thus obtained may be subjected to cyclization using sulfuric acid as a catalyst, thereby being capable of synthesizing pyrano-o-naphthoquinone or furano-o-naphthoquinone derivatives among compounds of Formula I.

Preparation Method 2: Diels-Alder Reaction Using 3-methylene-1,2,4-[3H]naphthalenetrione As taught by V. Nair et al, Tetrahedron Lett. 42 (2001), 4549-4551, it is reported that a variety of pyrano-o-naphthoquinone derivatives can be relatively easily synthesized by subjecting 3-methylene-1,2,4-[3H]naphthalenetrione, produced upon heating 2-hydroxy-1,4-naphthoquinone and formaldehyde together, to Diels-Alder reaction with various olefin compounds. This method is advantageous in that various forms of pyrano-o-naphtho-quinone derivatives can be synthesized in a relatively simplified manner, as compared to induction of cyclization of lapachol derivatives using sulfuric acid as a catalyst.

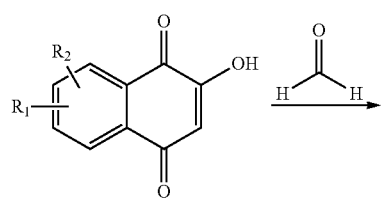

Preparation Method 3: Haloakylation and Cyclization by Radical Reaction

The same method used in synthesis of Cryptotanshinone and 15,16-dihydro-tanshinone can also be conveniently employed for synthesis of furano-o-naphthoquinone derivatives. That is, as taught by A. C. Baillie et al (J. Chem. Soc. (C) 1968, 48-52), 2-haloethyl or 3-haloethyl radical chemical species, derived from 3-halopropanoic acid or 4-halobutanoic acid derivative, can be reacted with 2-hydroxy-1,4-naphthoquinone to thereby synthesize 3-(2-haloethyl or 3-halopropyl)-2-hydroxy-1,4-naphthoquinone which is then subjected to cyclization under suitable acidic catalyst conditions to synthesize various pyrano-o-naphthoquinone or furano-o-naphthoquinone derivatives.

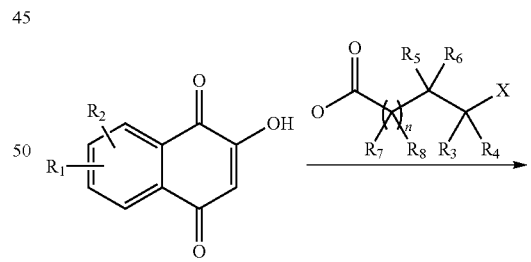

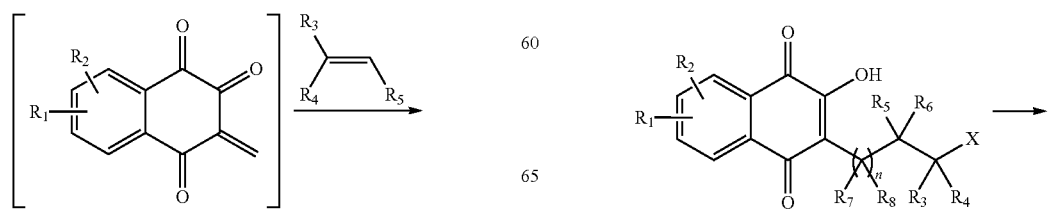

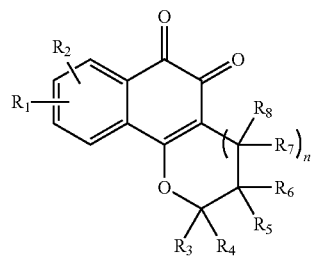

Preparation Method 4: Cyclization of 4,5-benzofurandione by Diels-Alder Reaction Another method used in synthesis of Cryptotanshinone and 15,16-dihydro-tanshinone may be a method taught by J. K. Snyder et al (Tetrahedron Letters 28 (1987), 3427-3430). According to this method, furano-o-naphthoquinone derivatives can be synthesized by cycloaddition via Diels-Alder reaction between 4,5-benzofurandione derivatives and various diene derivatives.

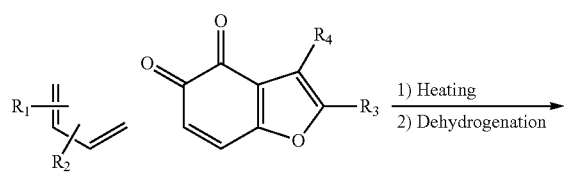

In addition, based on the above-mentioned preparation methods, various derivatives may be synthesized using relevant synthesis methods, depending upon kinds of substituents. Specific examples of derivatives thus synthesized and methods are exemplified in Table 1 below. Specific preparation methods will be described in the following Examples.

TABLE 1

| # | Structure | Formula | MW | Method |
|---|---|---|---|---|
| 1 | 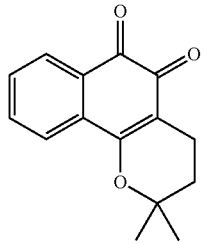 [SMILES: CC1(C)CCC2=C(O1)c1ccccc1C(=O)C2=O] | $C_{15}H_{14}O_3$ | 242.27 | Method 1 |
| 2 | 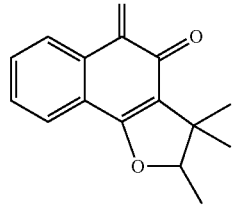 | $C_{15}H_{14}O_3$ | 242.27 | Method 1 |
| 3 | 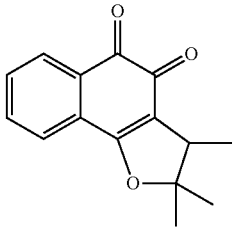 [SMILES: CC1C2=C(OC1(C)C)c1ccccc1C(=O)C2=O] | $C_{15}H_{14}O_3$ | 242.27 | Method 1 |
| 4 | 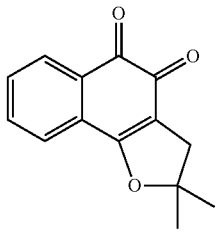 [SMILES: CC1(C)CC2=C(O1)c1ccccc1C(=O)C2=O] | $C_{14}H_{12}O_3$ | 228.24 | Method 1 |
| 5 | 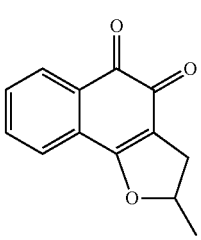 [SMILES: CC1CC2=C(O1)c1ccccc1C(=O)C2=O] | $C_{13}H_{10}O_3$ | 214.22 | Method 1 |
| 6 | 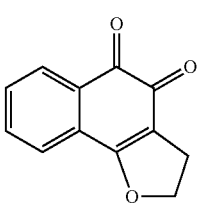 [SMILES: O=C1C(=O)c2ccccc2C2=C1CCO2] | $C_{12}H_8O_3$ | 200.19 | Method 2 |
| 7 | 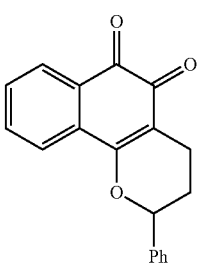 [SMILES: O=C1C(=O)c2ccccc2C2=C1CCC(c1ccccc1)O2] | $C_{19}H_{14}O_3$ | 290.31 | Method 1 |
| 8 | 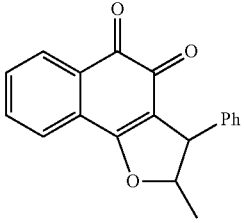 [SMILES: CC1OC2=C(C(=O)C(=O)c3ccccc32)C1c1ccccc1] | $C_{19}H_{14}O_3$ | 290.31 | Method 1 |

TABLE 1-continued

| # | Structure | Formula | MW | Method |
|---|---|---|---|---|
| 9 | 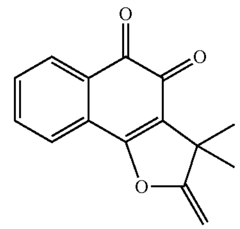 [SMILES: C=C1OC2=C(C(=O)C(=O)c3ccccc32)C1(C)C] | $C_{15}H_{12}O_3$ | 240.25 | Method 1 |
| 10 | 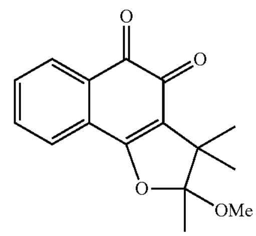 [SMILES: COC1(C)OC2=C(C(=O)C(=O)c3ccccc32)C1(C)C] | $C_{16}H_{16}O_4$ | 272.30 | Method 1 |
| 11 | 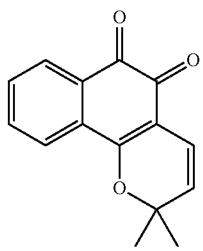 [SMILES: CC1(C)C=CC2=C(O1)c1ccccc1C(=O)C2=O] | $C_{15}H_{12}O_3$ | 240.25 | Method 1 |
| 12 | 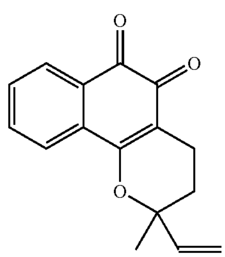 [SMILES: C=CC1(C)CCC2=C(O1)c1ccccc1C(=O)C2=O] | $C_{16}H_{14}O_3$ | 254.28 | Method 2 |
| 13 | 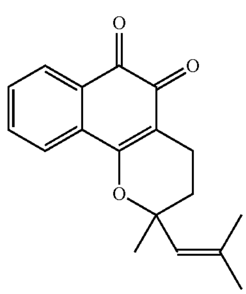 [SMILES: CC(C)=CC1(C)CCC2=C(O1)c1ccccc1C(=O)C2=O] | $C_{18}H_{18}O_3$ | 282.33 | Method 2 |
| 14 | 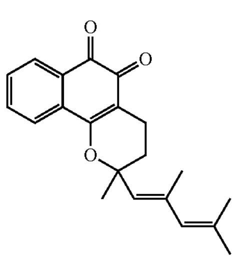 [SMILES: CC(C)=C/C(C)=C/C1(C)CCC2=C(O1)c1ccccc1C(=O)C2=O] | $C_{21}H_{22}O_3$ | 322.40 | Method 2 |
| 15 | 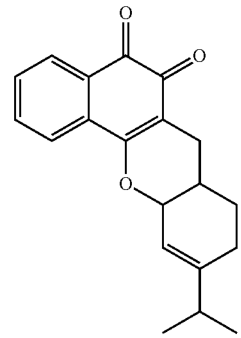 [SMILES: CC(C)C1=CC2OC3=C(CC2CC1)C(=O)C(=O)c1ccccc13] | $C_{21}H_{22}O_3$ | 322.40 | Method 2 |
| 16 | 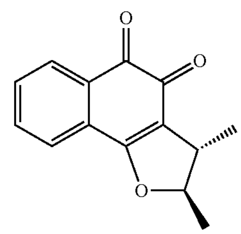 [SMILES: C[C@H]1OC2=C(C(=O)C(=O)c3ccccc32)[C@@H]1C] | $C_{14}H_{12}O_3$ | 228.24 | Method 1 |
| 17 | 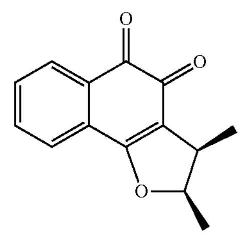 [SMILES: C[C@@H]1C2=C(O[C@@H]1C)c1ccccc1C(=O)C2=O] | $C_{14}H_{12}O_3$ | 228.24 | Method 1 |
| 18 | 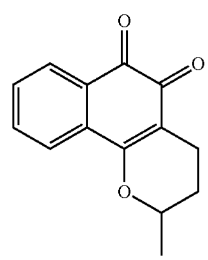 [SMILES: CC1CCC2=C(O1)c1ccccc1C(=O)C2=O] | $C_{14}H_{12}O_3$ | 228.24 | Method 1 |
| 19 | 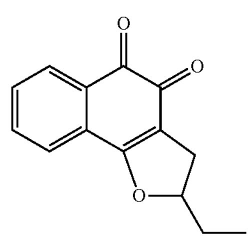 [SMILES: CCC1CC2=C(O1)c1ccccc1C(=O)C2=O] | $C_{14}H_{12}O_3$ | 228.24 | Method 1 |
| 20 | 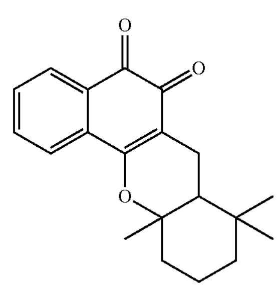 [SMILES: CC1(C)CCCC2(C)OC3=C(CC12)C(=O)C(=O)c1ccccc13] | $C_{20}H_{22}O_3$ | 310.39 | Method 1 |

TABLE 1-continued

| # | Structure | Formula | MW | Method |
|---|---|---|---|---|
| 21 | 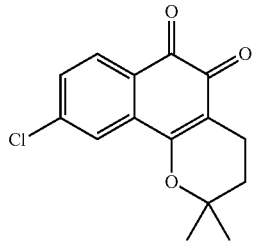 [SMILES: CC1(C)CCC2=C(O1)c1cc(Cl)ccc1C(=O)C2=O] | $C_{15}H_{13}ClO_3$ | 276.71 | Method 1 |
| 22 | 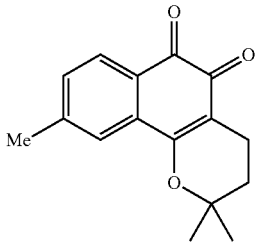 | $C_{16}H_{16}O_3$ | 256.30 | Method 1 |
| 23 | 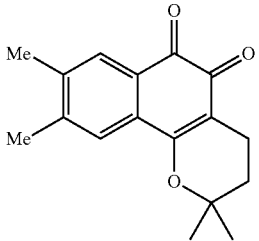 | $C_{17}H_{18}O_5$ | 302.32 | Method 1 |
| 24 | 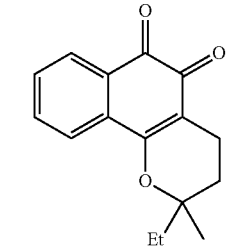 [SMILES: CCC1(C)CCC2=C(O1)c1ccccc1C(=O)C2=O] | $C_{16}H_{16}O_3$ | 256.30 | Method 1 |
| 25 | 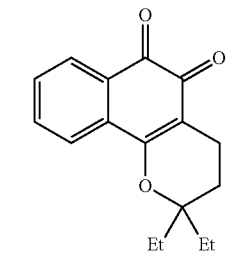 | $C_{17}H_{18}O_3$ | 270.32 | Method 1 |
| 26 | 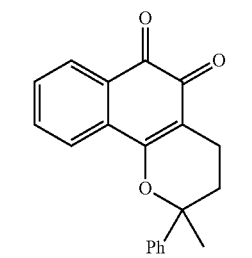 [SMILES: CC1(c2ccccc2)CCC2=C(O1)c1ccccc1C(=O)C2=O] | $C_{20}H_{16}O_3$ | 304.34 | Method 1 |
| 27 | 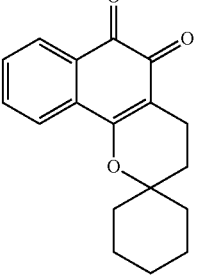 | $C_{18}H_{18}O_3$ | 282.33 | Method 1 |
| 28 | 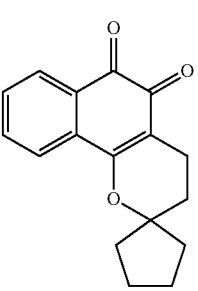 [SMILES: O=C1C(=O)c2ccccc2C2=C1CCC1(CCCC1)O2] | $C_{17}H_{16}O_3$ | 268.31 | Method 1 |
| 29 | 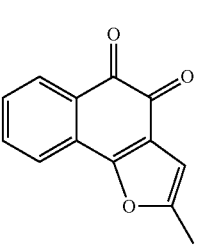 [SMILES: Cc1cc2c(o1)-c1ccccc1C(=O)C2=O] | $C_{13}H_8O_3$ | 212.20 | Method 1 |
| 30 | 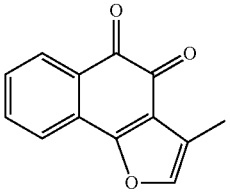 [SMILES: Cc1coc2c1C(=O)C(=O)c1ccccc1-2] | $C_{13}H_8O_3$ | 212.20 | Method 4 |
| 31 | 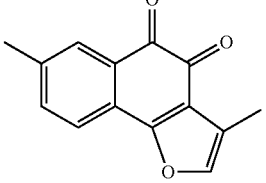 | $C_{14}H_{10}O_3$ | 226.23 | Method 4 |
| 32 | 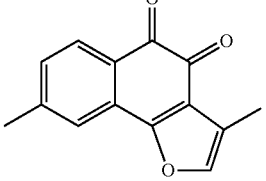 | $C_{14}H_{10}O_3$ | 226.23 | Method 4 |

The pharmaceutical composition of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more pharmaceutically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as is suitable and understood in the art; e.g., in Remington's Pharmaceutical Sciences, above. In the present invention, the compounds of Formula I may be formulated into injectable and parenteral preparation depending upon intended purpose.

For injection, the agents of the present invention may be formulated in aqueous solutions, preferably in physiologically compatible buffers such as Hanks's solution, Ringer's solution, or physiological saline. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compound of the present invention to be formulated as tablet, pill, powder, granule, dragee, capsule, liquid, gel, syrup, slurry, suspension and the like, for oral ingestion by a patient. Preferred are capsule, tablet, pill, powder and granule, and capsule and tablet are particularly useful. Tablet and pill are preferably prepared in enteric coating. Pharmaceutical preparations for oral use can be obtained by mixing one or more excipients with one or more compounds of the present invention, optionally grinding the resulting mixture, and processing the mixture of granules, after adding suitable auxiliaries, if desired, to obtain tablets or dragee cores. Suitable excipients may be fillers such as sugars, including lactose, sucrose, mannitol and sorbitol; and cellulose substances such as, for example, corn starch, wheat starch, rice starch, potato starch, gelatin, gum tragacanth, methyl cellulose, hydroxypropylmethyl-cellulose, sodium carboxymethyl cellulose, and/or polyvinylpyrrolidone (PVP). If desired, there may be added disintegrating agents such as cross-linked polyvinyl pyrrolidone, agar, or alginic acid or a salt thereof such as sodium alginate, lubricants such as magnesium stearate and carries such as binders.

Pharmaceutical preparations which can be used orally may include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate. In soft capsules, the active compounds may be dissolved or dispersed in suitable solvents, such as fatty acid, liquid paraffin, or liquid polyethylene glycols. In addition, stabilizers may also be added. All formulations for oral administration should be in dosage forms suitable for such administration.

The compounds may be formulated for parenteral administration by injection, e.g., by bolus injection or continuous infusion. Formulations for injection may be presented in unit dosage forms, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Alternatively, the active ingredient may be in powder form for constitution with a suitable vehicle, e.g., sterile pyrogen-free water, before use.

Pharmaceutical compositions suitable for use in the present invention include compositions in which the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

When the pharmaceutical composition of the present invention is formulated into a unit dosage form, the compound of Formula I as the active ingredient is preferably contained in a unit dose of about 0.1 to 1,000 mg. The amount of the compound of Formula I administered will be determined by the attending physician, depending upon body weight and age of patients being treated, characteristic nature and the severity of diseases. However, for adult patients, a dose of the active ingredient administered to the patient is typically within a range of about 1 to 1000 mg/kg BW/day, depending upon frequency and intensity of administration. For intramuscular or intravenous administration into adult patients, the total of about 1 to 500 mg per day as a single dose will be sufficient, but the use of a higher daily dose may be preferred for some patients.

In accordance with another aspect of the present invention, there is provided a use of a compound of Formula I in the preparation of a drug for the treatment or prevention of disease syndromes. The disease syndromes refer to obesity, diabetes, metabolic syndromes, degenerative diseases and mitochondrial dysfunction-related diseases. The term "treatment" of the disease syndromes refers to stopping or delaying of the disease progress, when the drug is used in the subject exhibiting symptoms of disease onset. The term "prevention" refers to stopping or delaying of symptoms of disease onset, when the drug is used in the subject exhibiting no symptoms of disease onset but having high risk of disease onset.

EXAMPLES

Now, the present invention will be described in more detail with reference to the following Examples and Experimental Examples. These examples are provided only for illustrating the present invention and should not be construed as limiting the scope and spirit of the present invention.

Example 1

Synthesis of β-Lapachone (Compound 1)

17.4 g (0.10M) of 2-hydroxy-1,4-naphthoquinone was dissolved in 120 ml of DMSO, and 0.88 g (0.11M) of LiH was gradually added thereto. Here, this should be done with care because hydrogen evolves. The reaction solution was stirred, and after confirming no further production of hydrogen, was additionally stirred for another 30 min. Then, 15.9 g (0.10M) of prenyl bromide (1-bromo-3-methyl-2-butene) and 3.35 g (0.025M) of LiI were gradually added thereto. The reaction solution was heated to 45° C. and then stirred vigorously for 12 hours at that temperature. The reaction solution was cooled below 10° C., and 76 g of ice was first added and 250 ml of water was then added. Thereafter, 25 ml of concentrated HCl was gradually added to maintain the resulting solution at an acidic pH>1. 200 ml of EtOAc was added to the reaction mixture which was then stirred vigorously, thereby producing white solids that were not dissolved in EtOAc. These solids were filtered and an EtOAc layer was separated. The aqueous layer was extracted once again with 100 ml of EtOAc and was combined with the previously extracted organic layer. The organic layer was washed with 150 ml of 5% $NaHCO_3$, and was concentrated. The resulting concentrates were dissolved in 200 ml of $CH_2Cl_2$, and were vigorously shaken to separate two layers with addition of 70 ml of an aqueous 2N NaOH solution. A $CH_2Cl_2$ layer was further separated twice with treatment of an aqueous 2N NaOH solution (70 ml×2). The thus-separated aqueous solutions were combined together and adjusted to an acidic pH>2, thereby forming solids. The resulting solids were filtered and separated to give Lapachol. The thus-obtained Lapachol was recrystallized from 75% EtOH. The resulting Lapachol was mixed with 80 ml of sulfuric acid, and the mixture was vigorously stirred at room temperature for 10 min and 200 g of ice was added thereto to complete the reaction. 60 ml of $CH_2Cl_2$ was added to the reaction materials which were then shaken vigorously. Thereafter, a $CH_2Cl_2$ layer was separated and washed with 5% $NaHCO_3$. An aqueous layer was extracted once again using 30 ml of $CH_2Cl_2$, washed with 5% $NaHCO_3$ and combined with the previously extracted organic layer. The organic layer was dried over $MgSO_4$ and concentrated to give impure β-Lapachone. The thus-obtained β-Lapachone was recrystallized from isopropanol, thereby obtaining 8.37 g of pure β-Lapachone.

$^1$H-NMR ($CDCl_3$, δ): 8.05 (1H, dd, J=1, 8 Hz), 7.82 (1H, dd, J=1, 8 Hz), 7.64 (1H, dt, J=1, 8 Hz), 7.50 (1H, dt, J=1, 8 Hz), 2.57 (2H, t, J=6.5 Hz), 1.86 (2H, t, J=6.5 Hz) 1.47 (6H, s)

Example 2

Synthesis of Dunnione (Compound 2)

In the process of obtaining Lapachol in Example 1, solids separated without being dissolved in EtOAc are 2-prenyloxy-1,4-naphthoquinone, an O-alkylation product, unlike Lapachol which is a C-alylation product. The separated 2-prenyloxy-1,4-naphthoquinone was first recrystallized once again from EtOAc. 3.65 g (0.015M) of the thus-purified solids was dissolved in toluene and toluene was refluxed for 5 hours to induce Claisen Rearrangement. Toluene was concentrated by distillation under reduced pressure and was then mixed with 15 ml of sulfuric acid, without further purification. The resulting mixture was stirred vigorously at room temperature for 10 min and 100 g of ice was added thereto to complete the reaction. 50 ml of $CH_2Cl_2$ was added to the reaction materials which were shaken vigorously. Thereafter, a $CH_2Cl_2$ layer was separated and washed with 5% $NaHCO_3$. An aqueous layer was extracted once again using 20 ml of $CH_2Cl_2$, washed with 5% $NaHCO_3$ and combined with the previously extracted organic layer. The organic layer was dried over $MgSO_4$, concentrated and purified by chromatography on silica gel to give 2.32 g of pure Dunnione.

$^1$H-NMR ($CDCl_3$, δ): 8.05 (1H, d, J=8 Hz), 7.64 (2H, d, J=8 Hz), 7.56 (1H, m), 4.67 (1H, q, J=7 Hz), 1.47 (3H, d, J=7 Hz), 1.45 (3H, s) 1.27 (3H, s)

Example 3

Synthesis of α-Dunnione (Compound 3)

4.8 g (0.020M) of 2-prenyloxy-1,4-naphthoquinone purified in Example 2 was dissolved in xylene, and xylene was refluxed for 15 hours, thereby inducing Claisen Rearrangement under significantly higher temperature conditions and prolonged reaction conditions as compared to Example 2. According to this reaction process, α-Dunnione that had progressed to cyclization was obtained together with a Lapachol derivative which had undergone Claisen Rearrangement and in which one of two methyl groups has shifted. Xylene was concentrated by distillation under reduced pressure and purified by chromatography on silica gel to give 1.65 g of pure α-Dunnione.

$^1$H-NMR ($CDCl_3$, δ): 8.06 (1H, d, J=8 Hz), 7.64 (2H, m), 7.57 (1H, m), 3.21 (1H, q, J=7 Hz), 1.53 (3H, s), 1.51 (3H, s) 1.28 (3H, d, J=7 Hz)

Example 4

Synthesis of Compound 4

17.4 g (0.10M) of 2-hydroxy-1,4-naphthoquinone was dissolved in 120 ml of DMSO, and 0.88 g (0.11M) of LiH was gradually added thereto. Here, this should be done with care because hydrogen evolves. The reaction solution was stirred, and after confirming no further production of hydrogen, was additionally stirred for another 30 min. Then, 14.8 g (0.11M) of methallyl bromide (1-bromo-2-methylpropene) and 3.35 g (0.025M) of LiI were gradually added thereto. The reaction solution was heated to 45° C. and then stirred vigorously for 12 hours at that temperature. The reaction solution was cooled below 10° C., and 80 g of ice was first added and 250 ml of water was then added. Thereafter, 25 ml of concentrated HCl was gradually added to maintain the resulting solution at an acidic pH>1. 200 ml of $CH_2Cl_2$ was added to the reaction mixture which was then shaken vigorously to separate two layers. The aqueous layer was extracted once again with addition of 70 ml of $CH_2Cl_2$ and was combined with the previously extracted organic layer. Two materials were confirmed to be formed newly by TLC and were subsequently used without any particular separation process. The organic layer was concentrated by distillation under reduced pressure, dissolved again in xylene and then refluxed for 8 hours. In this process, two materials on TLC were combined into one, thereby obtaining a relatively pure Lapachol derivative. The thus-obtained Lapachol derivative was mixed with 80 ml of sulfuric acid and stirred vigorously at room temperature for 10 min, and 200 g of ice was added thereto to complete the reaction. 80 ml of $CH_2Cl_2$ was added to the reaction materials which were then shaken vigorously. Thereafter, a $CH_2Cl_2$ layer was separated and washed with 5% $NaHCO_3$. An aqueous layer was extracted once again using 50 ml of $CH_2Cl_2$, washed with 5% $NaHCO_3$ and combined with the previously extracted organic layer. The organic layer was dried over $MgSO_4$ and concentrated to give impure β-Lapachone derivative (Compound 4). The thus-obtained β-Lapachone derivative was recrystallized from isopropanol, thereby obtaining 12.21 g of pure Compound 4.

$^1$H-NMR ($CDCl_3$, δ): 8.08 (1H, d, J=8 Hz), 7.64 (2H, m), 7.57 (1H, m), 2.95 (2H, s), 1.61 (6H, s)

Example 5

Synthesis of Compound 5

Compound 5 was obtained in the same manner as in Example 4, except that allyl bromide was used instead of methallyl bromide.

$^1$H-NMR ($CDCl_3$, δ): 8.07 (1H, d, J=7 Hz), 7.65 (2H, m), 7.58 (1H, m), 5.27 (1H, m), 3.29 (1H, dd, J=10, 15 Hz), 2.75 (1H, dd, J=7, 15 Hz), 1.59 (3H, d, J=6 Hz)

Example 6

Synthesis of Compound 6

5.08 g (40 mM) of 3-chloropropionyl chloride was dissolved in 20 ml of ether and cooled to −78° C. 1.95 g (25 mM)

of sodium peroxide (Na$_2$O$_2$) was gradually added to the resulting solution while being vigorously stirred at that temperature, followed by further vigorous stirring for 30 min. The reaction solution was heated to 0° C. and 7 g of ice was added thereto, followed by additional stirring for another 10 min. An organic layer was separated, washed once again with 10 ml of cold water at 0° C., then with an aqueous NaHCO$_3$ solution at 0° C. The organic layer was separated, dried over MgSO$_4$, concentrated by distillation under reduced pressure below 0° C., thereby preparing 3-chloropropionic peracid.

1.74 g (10 mM) of 2-hydroxy-1,4-naphthoquinone was dissolved in 20 ml of acetic acid, and the previously prepared 3-chloropropionic peracid was gradually added thereto at room temperature. The reaction mixture was refluxed with stirring for 2 hours, and then distilled under reduced pressure to remove acetic acid. The resulting concentrates were dissolved in 20 ml of CH$_2$Cl$_2$, and washed with 20 ml of 5% NaHCO$_3$. An aqueous layer was extracted once again using 20 ml of CH$_2$Cl$_2$ and combined with the previously extracted organic layer. The organic layer was dried over MgSO$_4$ and concentrated to give Compound 6 in admixture with 2-(2-chloroethyl)-3-hydroxy-1,4-naphthoquinone. The resulting mixture was purified by chromatography on silica gel to give 0.172 g of a pure Lapachone derivative (Compound 6).

$^1$H-NMR (CDCl$_3$, δ): 8.07 (1H, d, J=7.6 Hz), 7.56-7.68 (3H, m), 4.89 (2H, t, J=9.2 Hz), 3.17 (2H, t, J=9.2 Hz)

Example 7

Synthesis of Compound 7

17.4 g (0.10M) of 2-hydroxy-1,4-naphthoquinone was dissolved in 120 ml of DMSO, and 0.88 g (0.11M) of LiH was gradually added thereto. Here, this should be done with care because hydrogen evolves. The reaction solution was stirred, and after confirming no further production of hydrogen, was additionally stirred for another 30 min. Then, 19.7 g (0.10M) of cinnamyl bromide (3-phenylallyl bromide) and 3.35 g (0.025M) of LiI were gradually added thereto. The reaction solution was heated to 45° C. and then stirred vigorously for 12 hours at that temperature. The reaction solution was cooled below 10° C., and 80 g of ice was first added and 250 ml of water was then added. Thereafter, 25 ml of concentrated HCl was gradually added to maintain the resulting solution at an acidic pH>1. 200 ml of CH$_2$Cl$_2$ was added to dissolve the reaction mixture which was then shaken vigorously to separate two layers. The aqueous layer was discarded, and a CH$_2$Cl$_2$ layer was treated with an aqueous 2N NaOH solution (100 ml×2) to separate the aqueous layer twice. At this time, the remaining CH$_2$Cl$_2$ layer after extraction with an aqueous 2N NaOH solution was used again in Example 8. The thus-separated aqueous solutions were combined and adjusted to an acidic pH>2 using concentrated HCl, thereby forming solids. The resulting solids were filtered and separated to give a Lapachol derivative. The thus-obtained Lapachol derivative was recrystallized from 75% EtOH. The resulting Lapachol derivative was mixed with 50 ml of sulfuric acid, and the mixture was vigorously stirred at room temperature for 10 min and 150 g of ice was added thereto to complete the reaction. 60 ml of CH$_2$Cl$_2$ was added to the reaction materials which were then shaken vigorously. Thereafter, a CH$_2$Cl$_2$ layer was separated and washed with 5% NaHCO$_3$. An aqueous layer was extracted once again using 30 ml of CH$_2$Cl$_2$, washed with 5% NaHCO$_3$ and combined with the previously extracted organic layer. The organic layer was concentrated and purified by chromatography on silica gel to give 2.31 g of pure Compound 7.

$^1$H-NMR (CDCl$_3$, δ): 8.09 (1H, dd, J=1.2, 7.6 Hz), 7.83 (1H, d, J=7.6 Hz), 7.64 (1H, dt, J=1.2, 7.6 Hz), 7.52 (1H, dt, J=1.2, 7.6 Hz), 7.41 (5H, m), 5.27 (1H, dd, J=2.5, 6.0 Hz), 2.77 (1H, m) 2.61 (1H, m), 2.34 (1H, m), 2.08 (1H, m), 0.87 (1H, m)

Example 8

Synthesis of Compound 8

The remaining CH$_2$Cl$_2$ layer, after extraction with an aqueous 2N NaOH solution in Example 7, was concentrated by distillation under reduced pressure. The resulting concentrates were dissolved in 30 ml of xylene, followed by reflux for 10 hours to induce Claisen Rearrangement. Xylene was concentrated by distillation under reduced pressure and was then mixed with 15 ml of sulfuric acid, without further purification. The resulting mixture was stirred vigorously at room temperature for 10 min and 100 g of ice was added thereto to complete the reaction. 50 ml of CH$_2$Cl$_2$ was added to the reaction materials which were shaken vigorously. Thereafter, a CH$_2$Cl$_2$ layer was separated and washed with 5% NaHCO$_3$. An aqueous layer was extracted once again using 20 ml of CH$_2$Cl$_2$, washed with 5% NaHCO$_3$ and combined with the previously extracted organic layer. The organic layer was dried over MgSO$_4$, concentrated and purified by chromatography on silica gel to give 1.26 g of pure Compound 8.

$^1$H-NMR (CDCl$_3$, δ): 8.12 (1H, dd, J=0.8, 8.0 Hz), 7.74 (1H, dd, J=1.2, 7.6 Hz), 7.70 (1H, dt, J=1.2, 7.6 Hz), 7.62 (1H, dt, J=1.6, 7.6 Hz), 7.27 (3H, m), 7.10 (2H, td, J=1.2, 6.4 Hz), 5.38 (1H, qd, J=6.4, 9.2 Hz), 4.61 (1H, d, J=9.2 Hz), 1.17 (3H, d, J=6.4 Hz)

Example 9

Synthesis of Compound 9

3.4 g (22 mM) of 1,8-diazabicyclo[5.4.0]undec-7-ene and 1.26 g (15 mM) of 2-methyl-3-butyn-2-ol were dissolved in 10 ml of acetonitrile and the resulting solution was cooled to 0° C. 3.2 g (15 mM) of trifluoroacetic anhydride was gradually added with stirring to the reaction solution which was then continued to be stirred at 0° C. 1.74 g (10 mM) of 2-hydroxy-1,4-naphthoquinone and 135 mg (1.0 mM) of cupric chloride (CuCl$_2$) were dissolved in 10 ml of acetonitrile in another flask, and were stirred. The previously purified solution was gradually added to the reaction solution which was then refluxed for 20 hours. The reaction solution was concentrated by distillation under reduced pressure and was then purified by chromatography on silica gel to give 0.22 g of pure Compound 9.

$^1$H-NMR (CDCl$_3$, δ): 8.11 (1H, dd, J=1.2, 7.6 Hz), 7.73 (1H, dd, J=1.2, 7.6 Hz), 7.69 (1H, dt, J=1.2, 7.6 Hz), 7.60 (1H, dt, J=1.6, 7.6 Hz), 4.95 (1H, d, J=3.2 Hz), 4.52 (1H, d, J=3.2 Hz), 1.56 (6H, s)

Example 10

Synthesis of Compound 10

0.12 g of Compound 9 was dissolved in 5 ml of MeOH, 10 mg of 5% Pd/C was added thereto, followed by vigorous stirring at room temperature for 3 hours. The reaction solution was filtered through silica gel to remove 5% Pd/C and was concentrated by distillation under reduced pressure to give Compound 10.

$^1$H-NMR (CDCl$_3$, δ): 8.05 (1H, td, J=1.2, 7.6 Hz), 7.64 (2H, m), 7.54 (1H, m), 3.48 (3H, s), 1.64 (3H, s), 1.42 (3H, s), 1.29 (3H, s)

Example 11

Synthesis of Compound 11

1.21 g (50 mM) of β-Lapachone (Compound 1) and 1.14 g (50 mM) of DDQ (2,3-dichloro-5,6-dicyano-1,4-benzoqinone) were dissolved in 50 ml of carbon tetrachloride and refluxed for 72 hours. The reaction solution was concentrated by distillation under reduced pressure and was then purified by chromatography on silica gel to give 1.18 g of pure Compound 11.

$^1$H-NMR (CDCl$_3$, δ): 8.08 (1H, dd, J=1.2, 7.6 Hz), 7.85 (1H, dd, J=0.8, 7.6 Hz), 7.68 (1H, dt, J=1.2, 7.6 Hz), 7.55 (1H, dt, J=1.2, 7.6 Hz), 6.63 (1H, d, J=10.0 Hz), 5.56 (1H, d, J=10.0 Hz), 1.57 (6H, s)

Example 12

Synthesis of Compound 12

1.74 g (10 mM) of 2-hydroxy-1,4-naphthoquinone, 3.4 g (50 mM) of 2-methyl-1,3-butadiene (Isoprene), 3.0 g (100 mM) of paraformaldehyde and 20 ml of 1,4-dioxane were placed into a pressure vessel, and were heated with stirring at 100° C. for 48 hours. The reaction vessel was cooled to room temperature, and contents therein were filtered. The filtrate was concentrated by distillation under reduced pressure and was then purified by chromatography on silica gel to give 238 mg of Compound 12, as a 2-vinyl derivative of β-Lapachone.

$^1$H-NMR (CDCl$_3$, δ): 8.07 (1H, dd, J=1.2, 7.6 Hz), 7.88 (1H, dd, J=0.8, 7.6 Hz), 7.66 (1H, dt, J=1.2, 7.6 Hz), 7.52 (1H, dt, J=0.8, 7.6 Hz), 5.87 (1H, dd, J=10.8, 17.2 Hz), 5.18 (1H, d, J=10.8 Hz), 5.17 (1H, 17.2 Hz), 2.62 (1H, m), 2.38 (1H, m), 2.17 (3H, s), 2.00 (1H, m), 1.84 (1H, m)

Example 13

Synthesis of Compound 13

1.74 g (10 mM) of 2-hydroxy-1,4-naphthoquinone, 4.8 g (50 mM) of 2,4-dimethyl-1,3-pentadiene and 3.0 g (100 mM) of paraformaldehyde were dissolved in 20 ml of 1,4-dioxane, and the resulting mixture was refluxed with vigorous stirring for 10 hours. The reaction vessel was cooled to room temperature, and contents therein were filtered to remove paraformaldehyde from solids. The filtrate was concentrated by distillation under reduced pressure and was then purified by chromatography on silica gel to give 428 mg of Compound 13, as a β-Lapachone derivative.

$^1$H-NMR (CDCl$_3$, δ): 8.06 (1H, dd, J=1.2, 7.6 Hz), 7.83 (1H, dd, J=0.8, 7.6 Hz), 7.65 (1H, dt, J=1.2, 7.6 Hz), 7.50 (1H, dt, J=0.8, 7.6 Hz), 5.22 (1H, bs), 2.61 (1H, m), 2.48 (1H, m), 2.04 (1H, m), 1.80 (3H, d, J=1.0 Hz), 1.75 (1H, m), 1.72 (1H, d, J=1.0 Hz), 1.64 (3H, s)

Example 14

Synthesis of Compound 14

5.3 g (30 mM) of 2-hydroxy-1,4-naphthoquinone, 20.4 g (150 mM) of 2,6-dimethyl-2,4,6-octatriene and 9.0 g (300 mM) of paraformaldehyde were dissolved in 50 ml of 1,4-dioxane, and the resulting mixture was refluxed with vigorous stirring for 10 hours. The reaction vessel was cooled to room temperature, and contents therein were filtered to remove paraformaldehyde from solids. The filtrate was concentrated by distillation under reduced pressure and was then purified by chromatography on silica gel to give 1.18 g of Compound 14, as a β-Lapachone derivative.

$^1$H-NMR (CDCl$_3$, δ): 8.07 (1H, dd, J=1.2, 7.6 Hz), 7.87 (1H, dd, J=0.8, 7.6 Hz), 7.66 (1H, dt, J=1.2, 7.6 Hz), 7.51 (1H, dt, J=0.8, 7.6 Hz), 6.37 (1H, dd, J=11.2, 15.2 Hz), 5.80 (1H, broad d, J=11.2 Hz), 5.59 (1H, d, J=15.2 Hz), 2.67 (1H, dd, J=4.8, 17.2 Hz), 2.10 (1H, dd, J=6.0, 17.2 Hz), 1.97 (1H, m), 1.75 (3H, bs), 1.64 (3H, bs), 1.63 (3H, s), 1.08 (3H, d, J=6.8 Hz)

Example 15

Synthesis of Compound 15

5.3 g (30 mM) of 2-hydroxy-1,4-naphthoquinone, 20.4 g (50 mM) of terpinen and 9.0 g (300 mM) of paraformaldehyde were dissolved in 50 ml of 1,4-dioxane, and the resulting mixture was refluxed with vigorous stirring for 10 hours. The reaction vessel was cooled to room temperature, and contents therein were filtered to remove paraformaldehyde from solids. The filtrate was concentrated by distillation under reduced pressure and was then purified by chromatography on silica gel to give 1.12 g of Compound 15, as a tetracyclic o-quinone derivative.

$^1$H-NMR (CDCl$_3$, δ): 8.06 (1H, d, J=7.6 Hz), 7.85 (1H, d, J=7.6 Hz), 7.65 (1H, t, J=7.6 Hz), 7.51 (1H, t, J=7.6 Hz), 5.48 (1H, broad s), 4.60 (1H, broad s), 2.45 (1H, d, J=16.8 Hz), 2.21 (1H, m), 2.20 (1H, d, J=16.8 Hz), 2.09 (1H, m), 1.77 (1H, m), 1.57 (1H, m), 1.07 (3H, s), 1.03 (3H, d, J=0.8 Hz), 1.01 (3H, d, J=0.8 Hz), 0.96 (1H, m)

Example 16

Synthesis of Compounds 16 and 17

17.4 g (0.10M) of 2-hydroxy-1,4-naphthoquinone was dissolved in 120 ml of DMSO, and 0.88 g (0.11M) of LiH was gradually added thereto. Here, this should be done with care because hydrogen evolves. The reaction solution was stirred, and after confirming no further production of hydrogen, was additionally stirred for another 30 min. Then, 16.3 g (0.12M) of crotyl bromide and 3.35 g (0.025M) of LiI were gradually added thereto. The reaction solution was heated to 45° C. and then vigorously stirred for 12 hours at that temperature. The reaction solution was cooled below 10° C., and 80 g of ice was first added and 250 ml of water was then added. Thereafter, 25 ml of concentrated HCl was gradually added to maintain the resulting solution at an acidic pH>1. 200 ml of CH$_2$Cl$_2$ was added to dissolve the reaction mixture which was then shaken vigorously to separate two layers. The aqueous layer was discarded, and a CH$_2$Cl$_2$ layer was treated with an aqueous 2N NaOH solution (100 ml×2) to separate the aqueous layer twice. At this time, the remaining CH$_2$Cl$_2$ layer after extraction with an aqueous 2N NaOH solution was used in Example 17. The thus-separated aqueous solutions were combined and adjusted to an acidic pH>2 using concentrated HCl, thereby forming solids. The resulting solids were filtered and separated to give a Lapachol derivative. The thus-obtained Lapachol derivative was recrystallized from 75% EtOH. The resulting Lapachol derivative was mixed with 50 ml of sulfuric acid, and the mixture was vigorously stirred at room temperature for 10 min, followed by addition of 150 g of ice to complete the reaction. 60 ml of CH$_2$Cl$_2$ was added to the reaction materials which were then shaken vigorously. Thereafter, a CH$_2$Cl$_2$ layer was separated and washed with 5% NaHCO$_3$. An aqueous layer was extracted once again using 30 ml of CH$_2$Cl$_2$, washed with 5% NaHCO$_3$ and combined with the previously extracted organic layer. The organic layer was concentrated and purified by chromatography on silica gel to give 1.78 and 0.43 g of pure Compounds 16 and 17, respectively.

$^1$H-NMR (CDCl$_3$, δ) of Compound 16: δ8.07 (1H, dd, J=0.8, 6.8 Hz), 7.64 (2H, broad d, J=3.6 Hz), 7.57 (1H, m), 5.17 (1H, qd, J=6.0, 8.8 Hz), 3.53 (1H, qd, J=6.8, 8.8 Hz), 1.54 (3H, d, 6.8 Hz), 1.23 (3H, d, 6.8 Hz)

$^1$H-NMR (CDCl$_3$, δ) of Compound 17: δ8.06 (1H, d, J=0.8, 7.2 Hz), 7.65 (2H, broad d, J=3.6 Hz), 7.57 (1H, m), 4.71 (1H, quintet, J=6.4 Hz), 3.16 (1H, quintet, J=6.4 Hz), 1.54 (3H, d, 6.4 Hz), 1.38 (3H, d, 6.4 Hz)

Example 17

Synthesis of Compounds 18 and 19

The remaining CH$_2$Cl$_2$ layer, after extraction with an aqueous 2N NaOH solution in Example 16, was concentrated by distillation under reduced pressure. The resulting concentrates were dissolved in 30 ml of xylene, followed by reflux for 10 hours to induce Claisen Rearrangement. Xylene was concentrated by distillation under reduced pressure and was then mixed with 15 ml of sulfuric acid, without further purification. The resulting mixture was stirred vigorously at room temperature for 10 min and 100 g of ice was added thereto to complete the reaction. 50 ml of CH$_2$Cl$_2$ was added to the reaction materials which were shaken vigorously. Thereafter, a CH$_2$Cl$_2$ layer was separated and washed with 5% NaHCO$_3$. An aqueous layer was extracted once again using 20 ml of CH$_2$Cl$_2$, washed with 5% NaHCO$_3$ and combined with the previously extracted organic layer. The organic layer was dried over MgSO$_4$, concentrated and purified by chromatography on silica gel to give 0.62 and 0.43 g of pure Compounds 18 and 19, respectively.

$^1$H-NMR (CDCl$_3$, δ) of Compound 18: 8.06 (1H, dd, J=0.8, 7.2 Hz), 7.81 (1H, dd, J=0.8, 7.6 Hz), 7.65 (1H, dt, J=0.8, 7.6 Hz), 7.51 (1H, dt, J=0.8, 7.2 Hz), 4.40 (1H, m), 2.71 (1H, m), 2.46 (1H, m), 2.11 (1H, m), 1.71 (1H, m), 1.54 (3H, d, 6.4 Hz), 1.52 (1H, m)

$^1$H-NMR (CDCl$_3$, δ) of Compound 19: 8.08 (1H, d, J=0.8, 7.2 Hz), 7.66 (2H, broad d, J=4.0 Hz), 7.58 (1H, m), 5.08 (1H, m), 3.23 (1H, dd, J=9.6, 15.2 Hz), 2.80 (1H, dd, J=7.2, 15.2 Hz), 1.92 (1H, m), 1.82 (1H, m), 1.09 (3H, t, 7.6 Hz)

Example 18

Synthesis of Compound 20

17.4 g (0.10M) of 2-hydroxy-1,4-naphthoquinone was dissolved in 120 ml of DMSO, and 0.88 g (0.11M) of LiH was gradually added thereto. Here, this should be done with care because hydrogen evolves. The reaction solution was stirred, and after confirming no further production of hydrogen, was additionally stirred for another 30 min. Then, 21.8 g (0.10M) of geranyl bromide and 3.35 g (0.025M) of LiI were gradually added thereto. The reaction solution was heated to 45° C. and then vigorously stirred for 12 hours at that temperature. The reaction solution was cooled below 10° C., and 80 g of ice was first added and 250 ml of water was then added. Thereafter, 25 ml of concentrated HCl was gradually added to maintain the resulting solution at an acidic pH>1. 200 ml of CH$_2$Cl$_2$ was added to dissolve the reaction mixture which was then shaken vigorously to separate two layers. The aqueous layer was discarded, and a CH$_2$Cl$_2$ layer was treated with an aqueous 2N NaOH solution (100 ml×2) to separate the aqueous layer twice. The thus-separated aqueous solutions were combined and adjusted to an acidic pH>2 using concentrated HCl, thereby forming solids. The resulting solids were filtered and separated to give 2-geranyl-3-hydroxy-1,4-naphthoquinone. The thus-obtained product was mixed with 50 ml of sulfuric acid without further purification, and the mixture was vigorously stirred at room temperature for 10 min, followed by addition of 150 g of ice to complete the reaction. 60 ml of CH$_2$Cl$_2$ was added to the reaction materials which were then shaken vigorously. Thereafter, a CH$_2$Cl$_2$ layer was separated and washed with 5% NaHCO$_3$. An aqueous layer was extracted once again using 30 ml of CH$_2$Cl$_2$, washed with 5% NaHCO$_3$ and combined with the previously extracted organic layer. The organic layer was concentrated and purified by chromatography on silica gel to give 3.62 g of pure Compound 20.

$^1$H-NMR (CDCl$_3$, δ): 8.05 (1H, d, J=7.6 Hz), 7.77 (1H, d, J=7.6 Hz), 7.63 (1H, t, J=7.6 Hz), 7.49 (1H, t, J=7.6 Hz), 2.71 (1H, dd, J=6.0, 17.2 Hz), 2.19 (1H, dd, J=12.8, 17.2 Hz), 2.13 (1H, m), 1.73 (2H, m), 1.63 (1H, dd, J=6.0, 12.8 Hz), 1.59 (1H, m), 1.57 (1H, m), 1.52 (1H, m), 1.33 (3H, s), 1.04 (3H, s), 0.93 (3H, s)

Example 19

Synthesis of Compound 21

Compound 21 was obtained in the same manner as in Example 1, except that 6-chloro-2-hydroxy-1,4-naphthoquinone was used instead of 2-hydroxy-1,4-naphthoquinone.

$^1$H-NMR (CDCl$_3$, δ): 8.02 (1H, d, J=8 Hz), 7.77 (1H, d, J=2 Hz), 7.50 (1H, dd, J=2, 8 Hz), 2.60 (2H, t, J=7 Hz), 1.87 (2H, t, J=7 Hz) 1.53 (6H, s)

Example 20

Synthesis of Compound 22

Compound 22 was obtained in the same manner as in Example 1, except that 2-hydroxy-6-methyl-1,4-naphthoquinone was used instead of 2-hydroxy-1,4-naphthoquinone.

$^1$H-NMR (CDCl$_3$, δ): 7.98 (1H, d, J=8 Hz), 7.61 (1H, d, J=2 Hz), 7.31 (1H, dd, J=2, 8 Hz), 2.58 (2H, t, J=7 Hz), 1.84 (2H, t, J=7 Hz) 1.48 (6H, s)

Example 21

Synthesis of Compound 23

Compound 23 was obtained in the same manner as in Example 1, except that 6,7-dimethoxy-2-hydroxy-1,4-naphthoquinone was used instead of 2-hydroxy-1,4-naphthoquinone.

$^1$H-NMR (CDCl$_3$, δ): 7.56 (1H, s), 7.25 (1H, s), 3.98 (6H, s), 2.53 (2H, t, J=7 Hz), 1.83 (2H, t, J=7 Hz) 1.48 (6H, s)

Example 22

Synthesis of Compound 24

Compound 24 was obtained in the same manner as in Example 1, except that 1-bromo-3-methyl-2-pentene was used instead of 1-bromo-3-methyl-2-butene.

¹H-NMR (CDCl₃, δ): 7.30-8.15 (4H, m), 2.55 (2H, t, J=7 Hz), 1.83 (2H, t, J=7 Hz), 1.80 (2H, q, 7 Hz) 1.40 (3H, s), 1.03 (3H, t, J=7 Hz)

Example 23

Synthesis of Compound 25

Compound 25 was obtained in the same manner as in Example 1, except that 1-bromo-3-ethyl-2-pentene was used instead of 1-bromo-3-methyl-2-butene.

¹H-NMR (CDCl₃, δ): 7.30-8.15 (4H, m), 2.53 (2H, t, J=7 Hz), 1.83 (2H, t, J=7 Hz), 1.80 (4H, q, 7 Hz) 0.97 (6H, t, J=7 Hz)

Example 24

Synthesis of Compound 26

Compound 26 was obtained in the same manner as in Example 1, except that 1-bromo-3-phenyl-2-butene was used instead of 1-bromo-3-methyl-2-butene.

¹H-NMR (CDCl₃, δ): 7.15-8.15 (9H, m), 1.90-2.75 (4H, m), 1.77 (3H, s)

Example 25

Synthesis of Compound 27

Compound 27 was obtained in the same manner as in Example 1, except that 2-bromo-ethylidenecyclohexane was used instead of 1-bromo-3-methyl-2-butene.

¹H-NMR (CDCl₃, δ): 7.30-8.25 (4H, m), 2.59 (2H, t, J=7 Hz), 1.35-2.15 (12H, m)

Example 26

Synthesis of Compound 28

Compound 28 was obtained in the same manner as in Example 1, except that 2-bromo-ethylidenecyclopentane was used instead of 1-bromo-3-methyl-2-butene.

¹H-NMR (CDCl₃, δ): 7.28-8.20 (4H, m), 2.59 (2H, t, J=7 Hz), 1.40-2.20 (10H, m)

Example 27

Synthesis of Compound 29

8.58 g (20 mM) of Compound 5 synthesized in Example 5 was dissolved in 1000 ml of carbon tetrachloride, followed by addition of 11.4 g (50 mM) of 2,3-dichloro-5,6-dicyano-1,4-benzoqinone, and the resulting mixture was refluxed for 96 hours. The reaction solution was concentrated by distillation under reduced pressure and the resulting red solids were then recrystallized from isopropanol, thereby obtaining 7.18 g of pure Compound 29.

¹H-NMR (CDCl₃, δ): 8.05 (1H, dd, J=1.2, 7.6 Hz), 7.66 (1H, dd, J=1.2, 7.6 Hz), 7.62 (1H, dt, J=1.2, 7.6 Hz), 7.42 (1H, dt, J=1.2, 7.6 Hz), 6.45 (1H, q, J=1.2 Hz), 2.43 (3H, d, J=1.2 Hz)

Example 28

Synthesis of Compound 30

Analogous to a synthesis method as taught in J. Org. Chem., 55 (1990) 4995-5008, 4,5-dihydro-3-methylbenzo[1,2-b]furan-4,5-dione {Benzofuran-4,5-dione} was synthesized using p-benzoquinone and 1-(N-morpholine)propene. 1.5 g (9.3 mM) of the thus-prepared benzofuran-4,5-dione and 3.15 g (28.2 mM) of 1-acetoxy-1,3-butadiene were dissolved in 200 ml of benzene, and the resulting mixture was refluxed for 12 hours. The reaction solution was cooled to room temperature and concentrated by distillation under reduced pressure. This was followed by chromatography on silica gel to give 1.13 g of pure Compound 30.

¹H-NMR (CDCl₃, δ): 8.05 (1H, dd, J=1.2, 7.6 Hz), 7.68 (1H, dd, J=1.2, 7.6 Hz), 7.64 (1H, td, J=1.2, 7.6 Hz), 7.43 (1H, td, J=1.2, 7.6 Hz), 7.26 (1H, q, J=1.2 Hz), 2.28 (3H, d, J=1.2 Hz)

Example 29

Synthesis of Compounds 31 and 32

1.5 g (9.3 mM) of 4,5-dihydro-3-methylbenzo[1,2-b]furan-4,5-dione {Benzofuran-4,5-dione} and 45 g (0.6M) of 2-methyl-1,3-butadiene were dissolved in 200 ml of benzene, and the resulting mixture was refluxed for 5 hours. The reaction solution was cooled to room temperature and completely concentrated by distillation under reduced pressure. The thus-obtained concentrates were dissolved again in 150 ml of carbon tetrachloride, followed by addition of 2.3 g (10 mM) of 2,3-dichloro-5,6-dicyano-1,4-benzoqinone, and the resulting mixture was further refluxed for 15 hours. The reaction solution was cooled and concentrated by distillation under reduced pressure. The resulting concentrates were purified by chromatography on silica gel to give 0.13 g and 0.11 g of pure Compounds 31 and 32, respectively.

¹H-NMR (CDCl₃, δ) of Compound 31: 7.86 (1H, s), 7.57 (1H, d, J=8.1 Hz), 7.42 (1H, d, J=8.1 Hz), 7.21 (1H, q, J=1.2 Hz), 2.40 (3H, s), 2.28 (1H, d, J=1.2 Hz)

¹H-NMR (CDCl₃, δ) of Compound 32: δ7.96 (1H, d, J=8.0 Hz), 7.48 (1H, s), 7.23 (2H, m), 2.46 (3H, s), 2.28 (1H, d, J=1.2 Hz)

Experimental Example 1

Determination of AMPK Activation

Myoblast cells, C2C12, were cultured in DMEM containing 10% bovine calf serum. When a cell density reached a range of about 85% to 90%, the culture medium was replaced with a medium containing 1% bovine calf serum to induce differentiation of cells. The thus-differentiated myoblast cells were treated with samples synthesized in Examples 1 through 29 at a concentration of 5 µg/ml, and compared with a control group. Enzymatic activity of AMPK was determined as follows. Firstly, C2C12 cells were lysed to obtain protein extracts and then ammonium sulfate was added to a final concentration of 30%, thereby precipitating proteins. Protein precipitates were dissolved in a buffer (62.5 mM Hepes, pH 7.2, 62.5 mM NaCl, 62.5 mM NaF, 1.25 mM Na pyrophosphate, 1.25 mM EDTA, 1 mM DTT, 0.1 mM PMSF, and 200 µM AMP). Thereafter, 200 µM SAMS peptide (HMRSAM SGLHLVKRR: the underlined serine residue is a phosphorylation site, as an AMPK phosphorylation site of acetyl-CoA carboxylase) and [γ-32P]ATP were added thereto and reactants were reacted for 10 minutes at 30° C. This was followed by spotting of the resulting reaction solution on p81 phosphocellulose paper. The p81 paper was washed with a 3% phosphoric acid solution and radioactivity thereof was measured. For each reaction condition, reactions involving no SAMS peptide were also conducted and basic values were subtracted from the thus-observed values.

The results thus obtained are shown in Table 2.

TABLE 2

| Compound | AMPK fold |
|---|---|
| DMSO (0.5%) | 1 |
| Compound 1 | 2.2 |
| Compound 2 | 1.4 |
| Compound 3 | 3.2 |
| Compound 4 | 2.2 |
| Compound 5 | 1.3 |
| Compound 6 | 2.2 |
| Compound 7 | 2.2 |
| Compound 8 | 1.9 |
| Compound 9 | 2.6 |
| Compound 10 | 1.6 |
| Compound 11 | 1.3 |
| Compound 12 | 2.1 |
| Compound 13 | 2.3 |
| Compound 14 | 1.5 |
| Compound 15 | 1.9 |
| Compound 16 | 2.5 |
| Compound 17 | 2.2 |
| Compound 18 | 2.3 |
| Compound 19 | 2.1 |
| Compound 20 | 2.3 |
| Compound 21 | 2.2 |
| Compound 22 | 1.9 |
| Compound 23 | 1.6 |
| Compound 24 | 2.1 |
| Compound 25 | 1.8 |
| Compound 26 | 2.2 |
| Compound 27 | 1.7 |
| Compound 28 | 1.7 |
| Compound 29 | 1.3 |
| Compound 30 | 1.2 |
| Compound 31 | 1.2 |
| Compound 32 | 1.3 |

As can be seen from Table 2, when compounds according to the present invention were treated on myoblast cells, C2C12, this treatment leads to increased enzymatic activity of AMPK.

Experimental Example 2

Weight Loss Effects in Obese Mice (Ob/Ob)

10-week-old C57BL/6JL Lep ob/Lep ob male mice having obesity characteristics and predisposition were purchased from Daehan Biolink Co., Ltd. (Chungchongbuk-do, Korea). Animals were raised in a breeding room maintained at a temperature of 23 C, 55% humidity, illumination of 300 to 500 lux, a 12-h light/dark (L/D) cycle, and ventilation of 10 to 18 times/hr. Animals were fed ad libitum pellets of Purina Rodent Laboratory Chow 5001 (purchased from Purina Mills Inc., St. Louis, Mo., USA) as a solid feed for experimental animals and tap water as drinking water. Mice were allowed to acclimate to new environment of the breeding room for two weeks and were then administered some pyrano-o-naphthoquinone and furano-o-naphthoquinone derivatives synthesized according to the present invention at doses of 100 mg/kg for 26 days. Observation was made on changes in body weight, blood glucose and dietary intake, with respect to a time course of administration. After administration was complete, Computed Tomography (CT) was performed to confirm changes in adipose tissue distribution of animals, changes in fat distribution of tissues in various organs, changes in sizes of adipocytes, and changes in glucose, lipid and enzyme levels in blood and liver.

Table 3 below shows results of changes over time in body weight of C57BL/6JL Lep ob/Lep ob mice to which some compounds of the present invention were administered.

TABLE 3

| Samples | Initial BW (g) | Final BW (g) | Increase in BW (%) |
|---|---|---|---|
| Control | 51.0 | 53.6 | 4.3 |
| Compound 1 | 55.9 | 46.5 | −16.8 |
| Compound 2 | 53.3 | 28.7 | −46.2 |
| Compound 3 | 55.1 | 39.7 | −27.9 |
| Compound 4 | 55.4 | 40.0 | −27.8 |
| Compound 5 | 59.7 | 36.1 | −39.5 |
| Compound 14 | 62.7 | 61.3 | −4.7 |
| Compound 15 | 56.8 | 53.0 | −6.7 |
| Compound 21 | 57.3 | 41.1 | −28.3 |
| Compound 22 | 58.3 | 48.7 | −16.5 |
| Compound 26 | 56.8 | 42.3 | −25.5 |

As can be seen from Table 3 above, administration of the compounds according to the present invention leads to a significant reduction in body weight, as compared to the control group.

Figure 2:
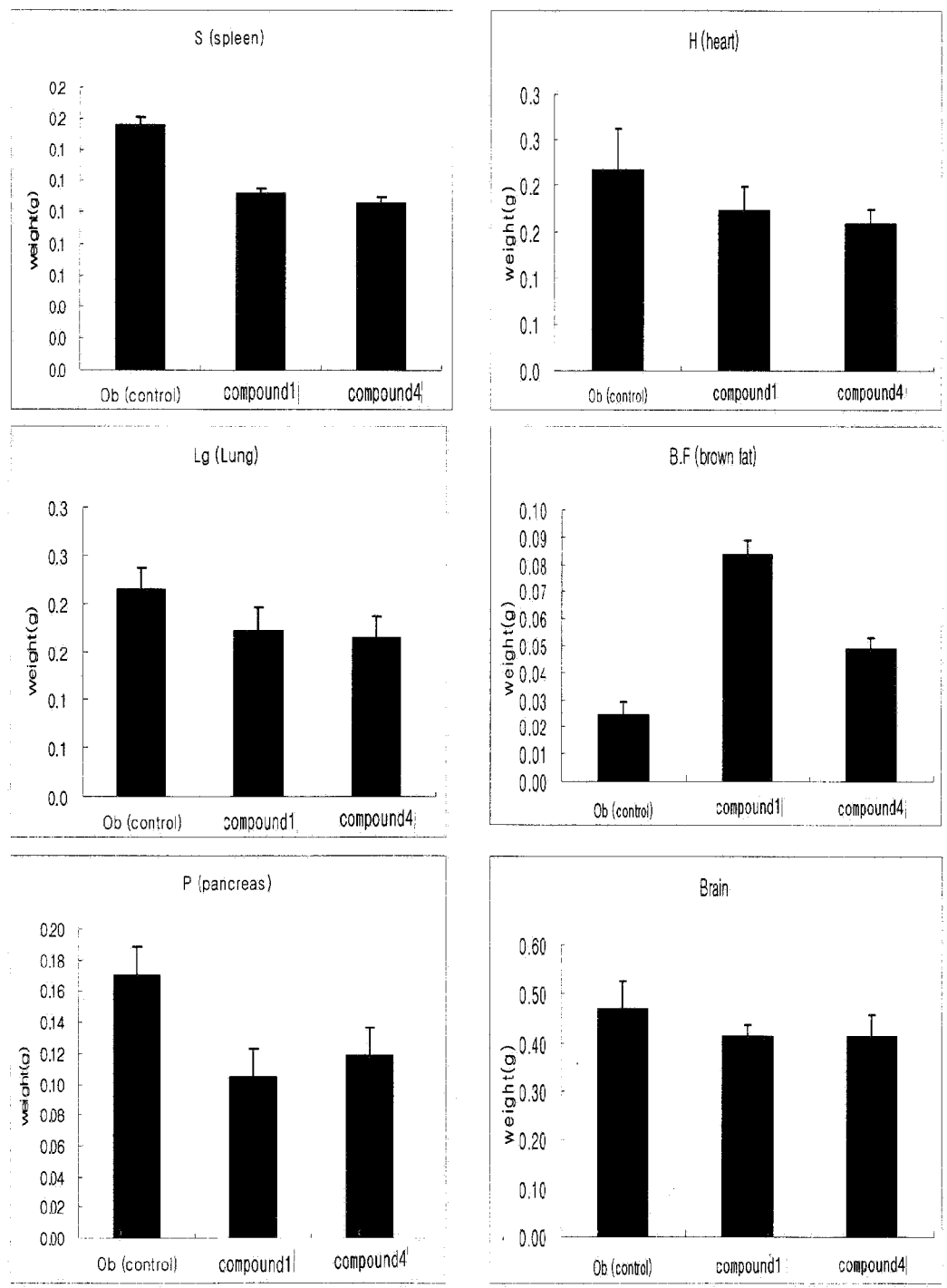
Figure 3:
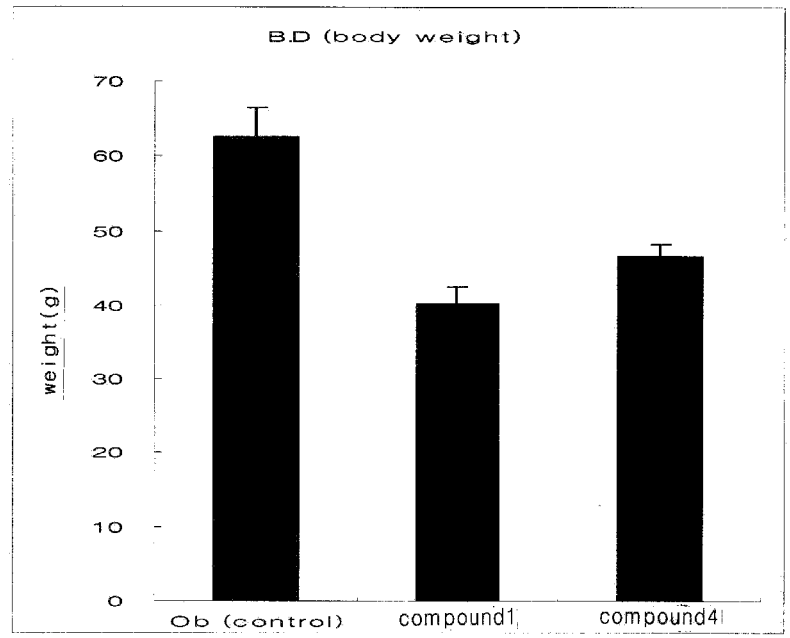

FIGS. 1 through 3 disclose fat distribution in terms of numerical values for the respective organs of C57BL/6JL Lep ob/Lep ob mice to which compounds as set forth in Table 3 were administered. As can be seen from graphs given in FIGS. 1 through 3, the experimental groups to which the compounds according to the present invention were administered exhibited a significant reduction in fat content of tissues for all organs, and further exhibited increases in brown fat contents compared with the control group, indicating that fat metabolism was significantly increased.

Table 4 below shows changes in blood lipid and glucose levels of C57BL/6JL Lep ob/Lep ob mice to which the compounds of the present invention were administered.

TABLE 4

| Sample | GOT | GPT | Cholesterol | Triglyceride | Glucose |
|---|---|---|---|---|---|
| Control | 233 | 206 | 187 | 248 | 228 |
| Compound 1 | 42 | 39 | 121 | 143 | 120 |
| Compound 2 | 50 | 43 | 123 | 154 | 125 |
| Compound 3 | 36 | 32 | 128 | 129 | 122 |
| Compound 4 | 48 | 44 | 130 | 148 | 134 |
| Compound 5 | 38 | 29 | 117 | 137 | 112 |
| Compound 14 | 95 | 87 | 160 | 216 | 193 |
| Compound 15 | 89 | 83 | 149 | 198 | 180 |
| Compound 21 | 46 | 39 | 127 | 138 | 127 |
| Compound 22 | 57 | 49 | 132 | 168 | 142 |
| Compound 26 | 40 | 33 | 128 | 137 | 131 |

As can be seen from Table 4 above, the groups to which the compounds according to the present invention were administered exhibited a significant reduction in triglyceride, cholesterol and glucose levels in the blood, as compared to the control group.

Experimental Example 3

Regulation of Phosphorylation of AMPK and ACC by β-lapachone

Figure 4:
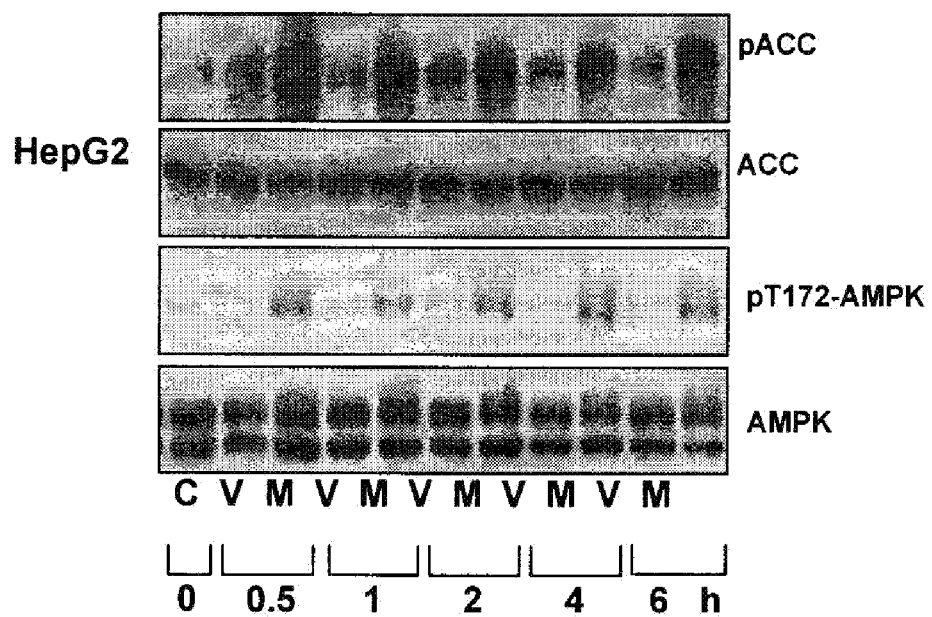
FIG. 4 is a photograph showing effects of β-lapachone on regulation of phosphorylation of AMPK and ACC in cells.

This example was carried out to confirm whether β-lapachone (Compound 1) has effects on phosphorylation of AMPK and ACC, which are intracellular energy-regulating proteins. In order to examine phosphorylation of AMP kinase and ACC (acetyl-CoA carboxylase) by β-lapachone, HepG2 cells (Human hepatocellular liver carcinoma cell line) were seeded onto a 6-well plate at a density of 1×10⁵ cells per well, and cultured in a RPMI+10% FBS medium. After growing the cells for 24 hours, the culture medium was replaced with a serum-free RPMI medium, and cells were treated with β-lapachone (10 μM) for 30 min, 1 hr, 2 hr, 4 hr and 6 hr, respectively, in combination with a control (DMSO). Anti-ACC and Anti-pS79-ACC were used in order to observe phosphorylated ACC, whereas Anti-AMPK and Anti-pT172-AMPK were used in order to observe phosphorylated AMP kinase, respectively. As shown in FIG. 4, phosphorylation of AMP kinase by β-lapachone could be observed from the initial time (30 min), and it can be confirmed that such phosphorylation effects lasted up to 6 hours. In addition, it can be confirmed that ACC, which is known as a target protein of AMP kinase, was also phosphorylated. These results show that activation of AMPK by the action of β-lapachone can suppress the activity of acetyl-CoA carboxylase, which is a crucial regulatory enzyme of lipogenesis.

Experimental Example 4

Effects of β-Lapachone on Phosphorylation of Endothelial Nitric Oxide Synthase (eNOS)

It is well-known that activation of AMPK activates NRF-1 and facilitates mitochondrial biogenesis. In addition, NO/cGMP activates PGC-1a and NRF-1 to facilitate mitochondrial biogenesis. In order to ascertain whether β-lapachone, which activates AMPK, is involved in production of nitric oxide (NO), a degree of phosphorylation, increasing the activity of endothelial nitric oxide synthase (eNOS), was determined. In order to examine phosphorylation of eNOS by the action of β-lapachone, Human Umbilical Vein Endothelial Cells (HUVEC) were seeded onto a 60-mm plate at a density of 1×10⁵ cells, and cultured in EBM2+5% FBS medium for 24 hours. The culture medium was replaced with a serum-free EBM2 medium, and cells were treated with β-lapachone (10 μM) for a predetermined period of time. Phosphorylated eNOS was observed using Anti-pS1177 eNOS.

Figure 5:
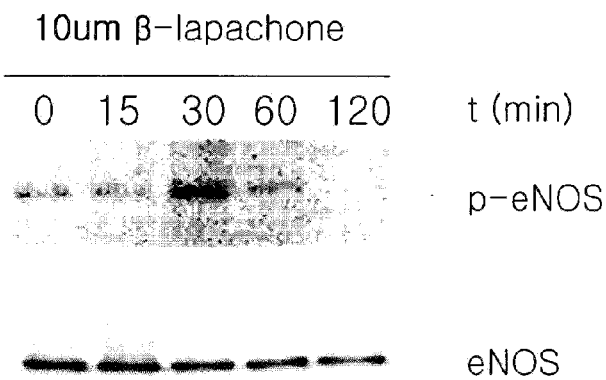
FIG. 5 is a photograph showing effects of β-lapachone on phosphorylation of endothelial nitric oxide synthase (eNOS)

As shown in FIG. 5, phosphorylation of eNOS reached a maximum increase 30 min after treatment of β-lapachone and then gradually diminished, thereby not observed 2 hours later. An increase in phosphorylation of eNOS by β-lapachone presents the possibility that β-lapachone may be therapeutically used for ischemic heart diseases and mitochondrial myopathy, as well as mitochondrial dysfunction-related diseases (for example, degenerative cerebral diseases, diabetes, cardiomyopathy, diseases associated with senescence).

Experimental Example 5

Effects of β-Lapachone on Activation of AMPK in C57BL/6 Mice

Figure 6:
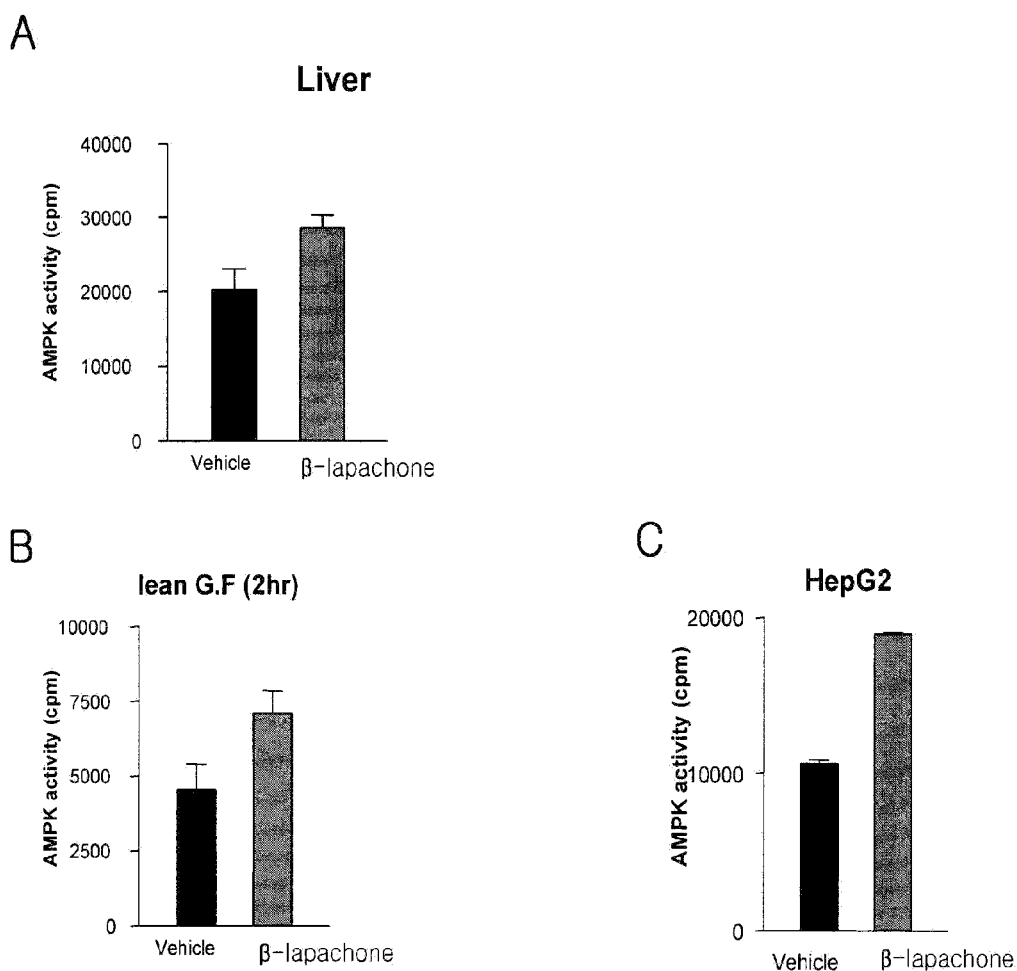
FIGS. 6A to 6C are graphs showing effects of β-lapachone on activation of AMPK in C57BL/6 mice.
Figure 7:
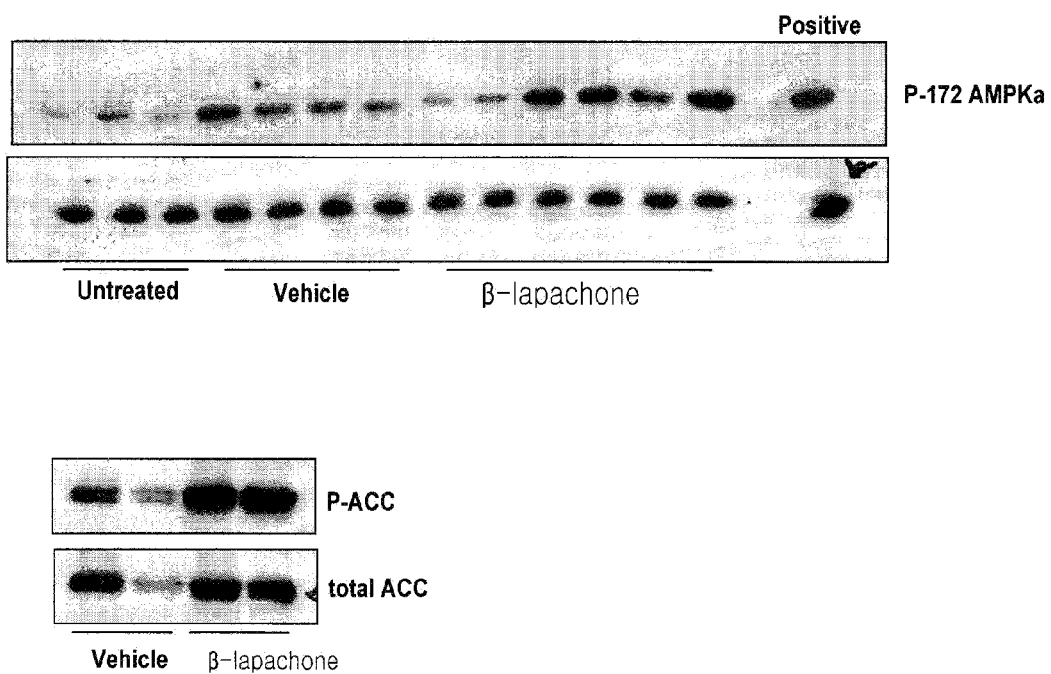
FIG. 7 is a photograph showing effects of β-lapachone on phosphorylation of AMPK & ACC in C57BL/6 mice.
Figure 12:
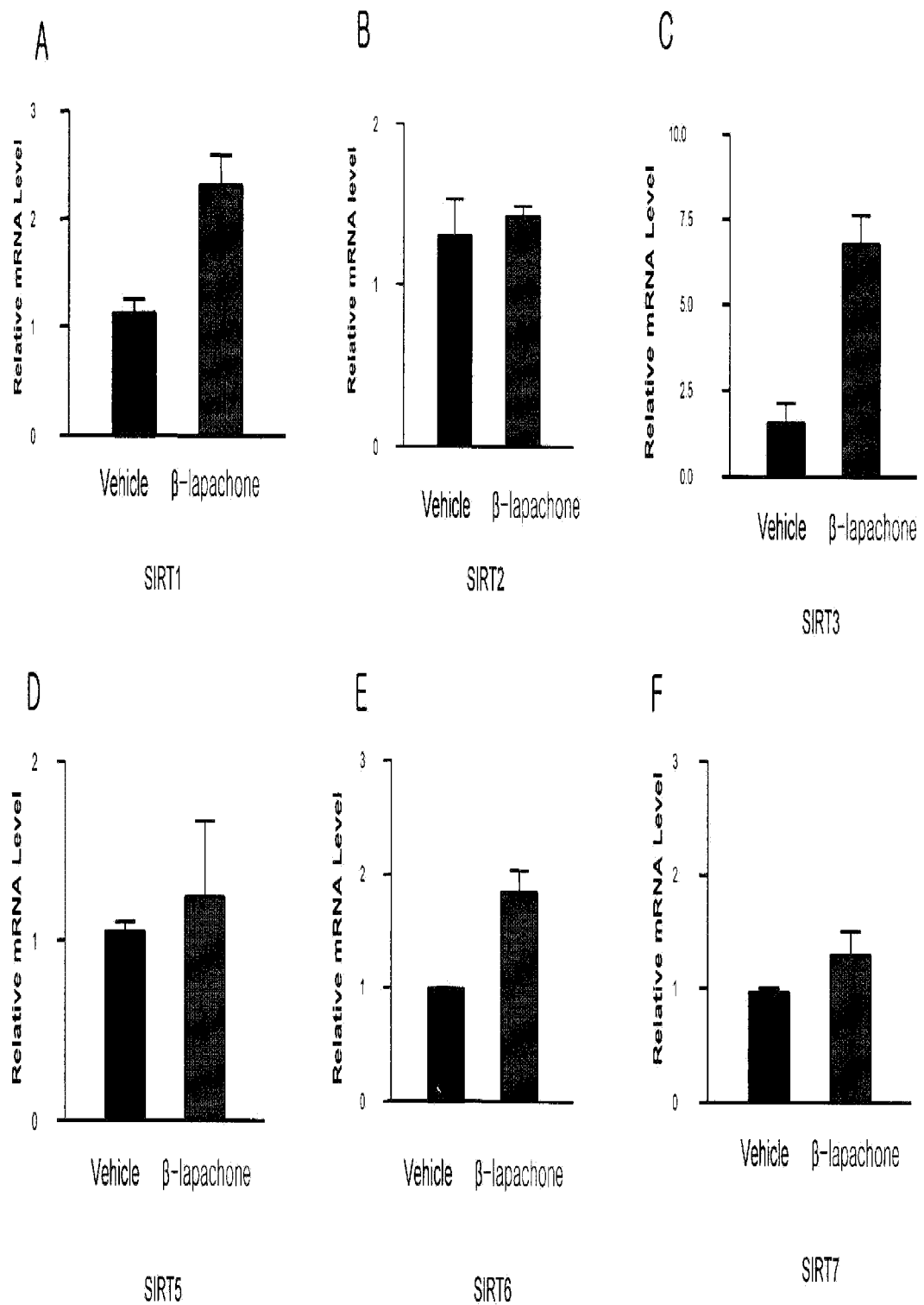
FIG. 12A through 12F are graphs showing effects of β-lapachone on transcript expression of SIRT-related proteins in C57BL/6 mice.

FIG. 6 shows that β-lapachone activates AMPK in C57BL/6 mice. A vehicle and 5 mg/kg of β-lapachone were administered via tail veins to C57BL/6 mice for 2 hours and 4 hours, respectively. Liver and gonadal adipose tissues were removed and activity of AMPK kinase was assayed. A degree of activation was expressed as a CPM value of radioisotopes. Using the same manner, HepG2 cells, a cell line derived from human liver, were treated with 10 μM β-lapachone for 30 min, and then an assay for AMPK kinase activity was carried out. As can be seen from the results in FIG. 12, administration of β-lapachone leads to increased AMPK activity in the liver and gonadal adipose tissues and hepatocytes.

Experimental Example 6

Effects of β-Lapachone on Phosphorylation of AMPK & ACC in C57BL/6 Mice

Figure 13:
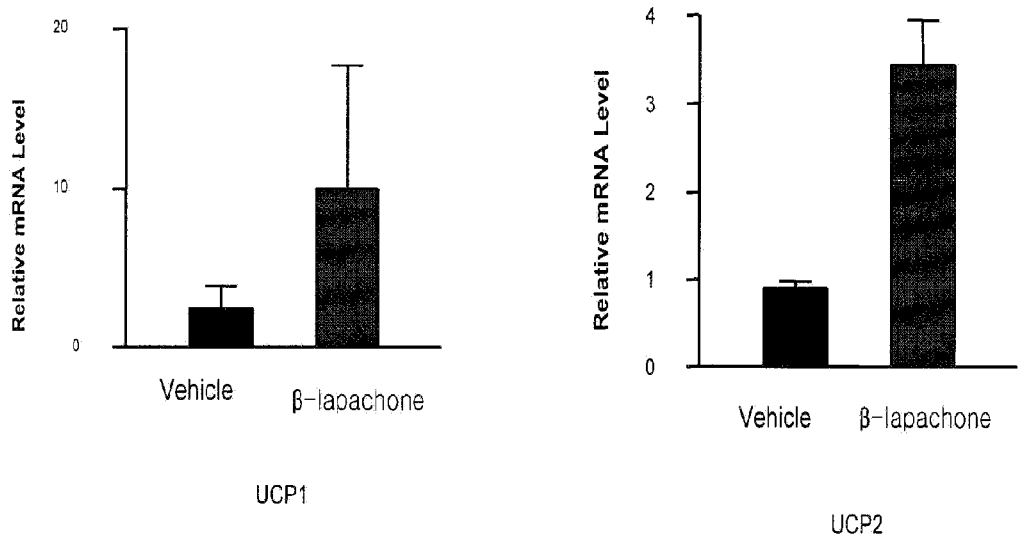
FIG. 13 is a graph showing effects of β-lapachone on transcript expression of UCP1 and UCP2 genes in C57BL/6 mice.

In order to investigate anti-obesity effects of β-lapachone, β-lapachone was administered daily to diet-induced obesity (DIO) mice at a dose of 50 mg/kg via an oral route, and effects of β-lapachone on phosphorylation of AMPK and ACC, which play an important role in energy metabolism and lipogenesis in the liver and gonadal adipose tissues, were examined. As shown in FIG. 13, it was confirmed through Western blot analysis that β-lapachone has an effect on phosphorylation of AMPK and ACC in the gonadal and liver tissues of C57BL/6 mice. Phosphorylated AMPK is believed to activate metabolism associated with energy. Whereas, it is believed that ACC, which is affected by activation of AMPK, is phosphorylated and lipogenic activity thereof is then inhibited, which will then exert some effects on lipid metabolism including inhibition of obesity.

Experimental Example 7

Figure 8:
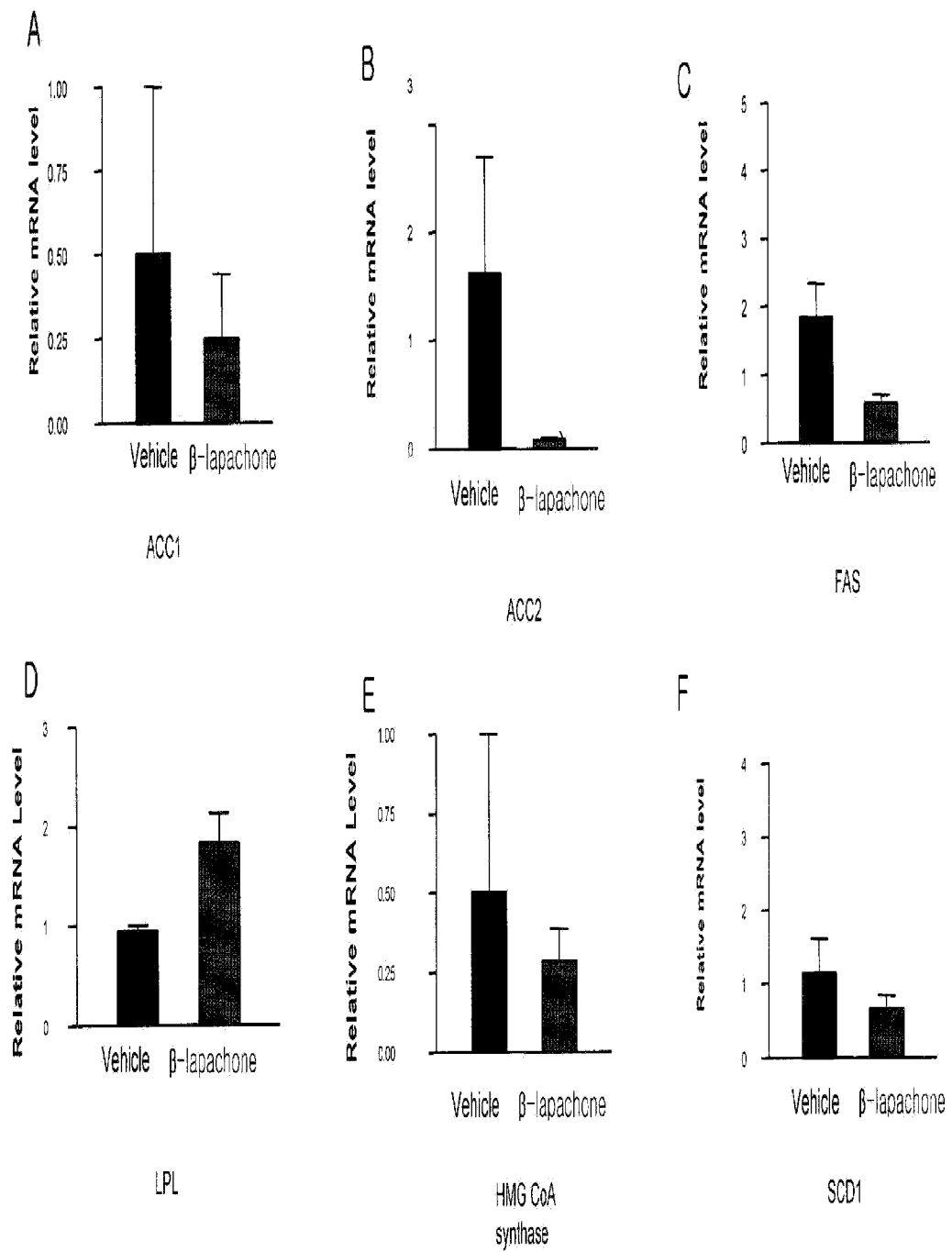
FIGS. 8A through 8F are graphs showing effects of β-lapachone on transcript expression of proteins involved in lipid metabolism of C57BL/6 mice.

Effects of β-Lapachone on Expression of Genes Involved in Lipid Metabolism of C57BL/6 Mice In order to investigate anti-obesity effects of β-lapachone, β-lapachone was administered daily to diet-induced obesity (DIO) mice at a dose of 50 mg/kg via an oral route, and an attempt was made to confirm levels of mRNAs of acetyl CoA carboxylase (ACC) 1 (7,8), ACC2 (9), fatty acid synthase (FAS) (10,11), lipoprotein lipase (LPL) (12-15), and stearoyl-CoA desaturase 1 (SCD1) (16,17), which participate in lipid metabolism in the liver and gonadal adipose tissues, by real-time quantitative PCR. These enzymes are very important for lipid metabolism; it is known that ACC catalyzes formation of malonyl CoA from acetyl CoA, FAS catalyzes formation of palmitate from malonyl CoA, and SCD1 catalyzes formation of monounsaturated fat, thus playing a critical role in formation of triacylglycerol, a major energy store. As such, these enzymes are closely correlated with obesity, diabetes, and lipid metabolism-related diseases. As shown in FIG. 8, expression levels of mRNAs of ACC1 and 2, FAS, LPL, and SCD1 were remarkably decreased in experimental groups to which β-lapachone was administered, as compared to a control group, and LPL mRNA levels in experimental groups were 2-fold increased as compared to the control group. Therefore, from the results of such increased or decreased expression of genes for the above-mentioned enzymes, it can be inferred that β-lapachone will be therapeutically effective substance for the treatment of metabolic syndromes.

Experimental Example 8

Figure 9:
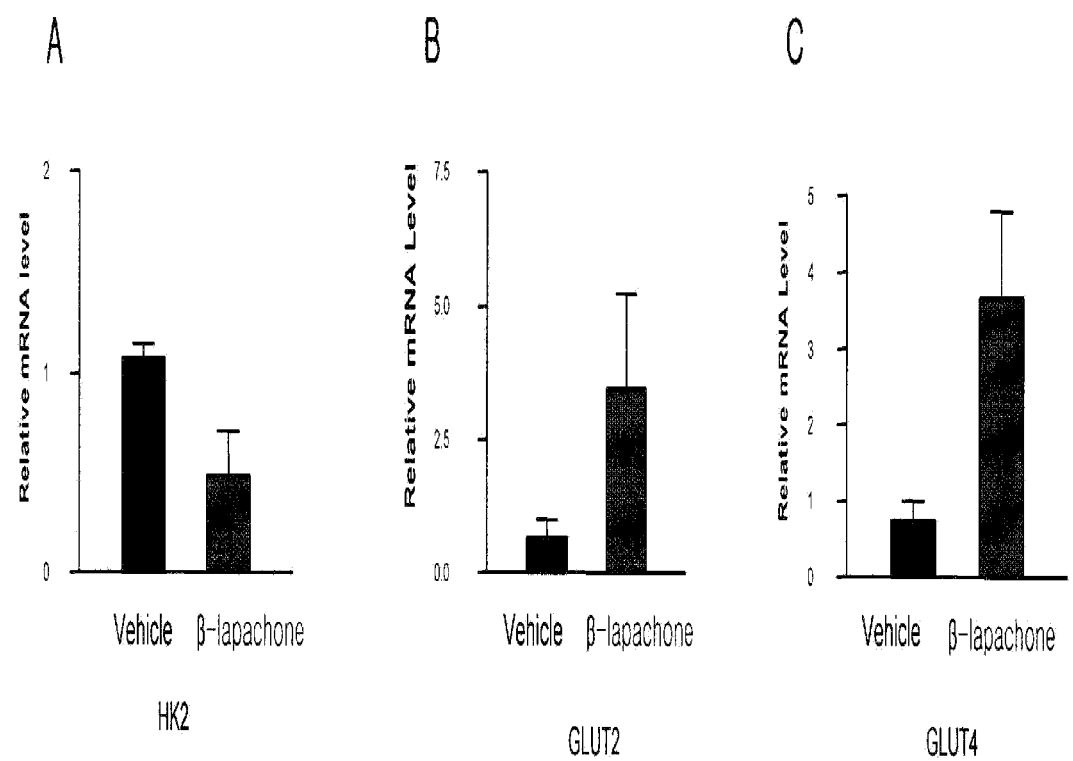
FIGS. 9A through 9C are graphs showing effects of β-lapachone on transcript expression of proteins involved in glucose metabolism of C57BL/6 mice.

Effects of 13-Lapachone on Gene Expression of Proteins Involved in Glucose Metabolism of C57BL/6 Mice β-lapachone was administered daily to diet-induced obesity (DIO) mice at a dose of 50 mg/kg via an oral route, and levels of mRNAs for hexokinase 2 (HK2) (21,22), glucose transporter (GLUT) 2 and GLUT4 (18,19,20) in the liver and gonadal adipose tissues were confirmed by real-time quantitative PCR. GLUT is well-known as a protein that mediates intracellular uptake and expenditure of blood glucose in organs such as liver, adipocytes and myoblast cells, whereas HK2, an enzyme belonging to a glucokinase class, phosphorylates proteins that are thus allowed to enter glycolytic pathways. As can be seen from the results of FIG. 9, a HK2 mRNA level is decreased as compared to a control group, whereas mRNAs of GLUT2 and GLUT4, two enzymes involved in glucose transportation, exhibited significant increases in their expression. Increased levels of GLUT2 and GLUT4 facilitate intracellular uptake of blood glucose, thus presenting the possibility of β-lapachone as an anti-diabetic drug.

Experimental Example 9

Figure 10:
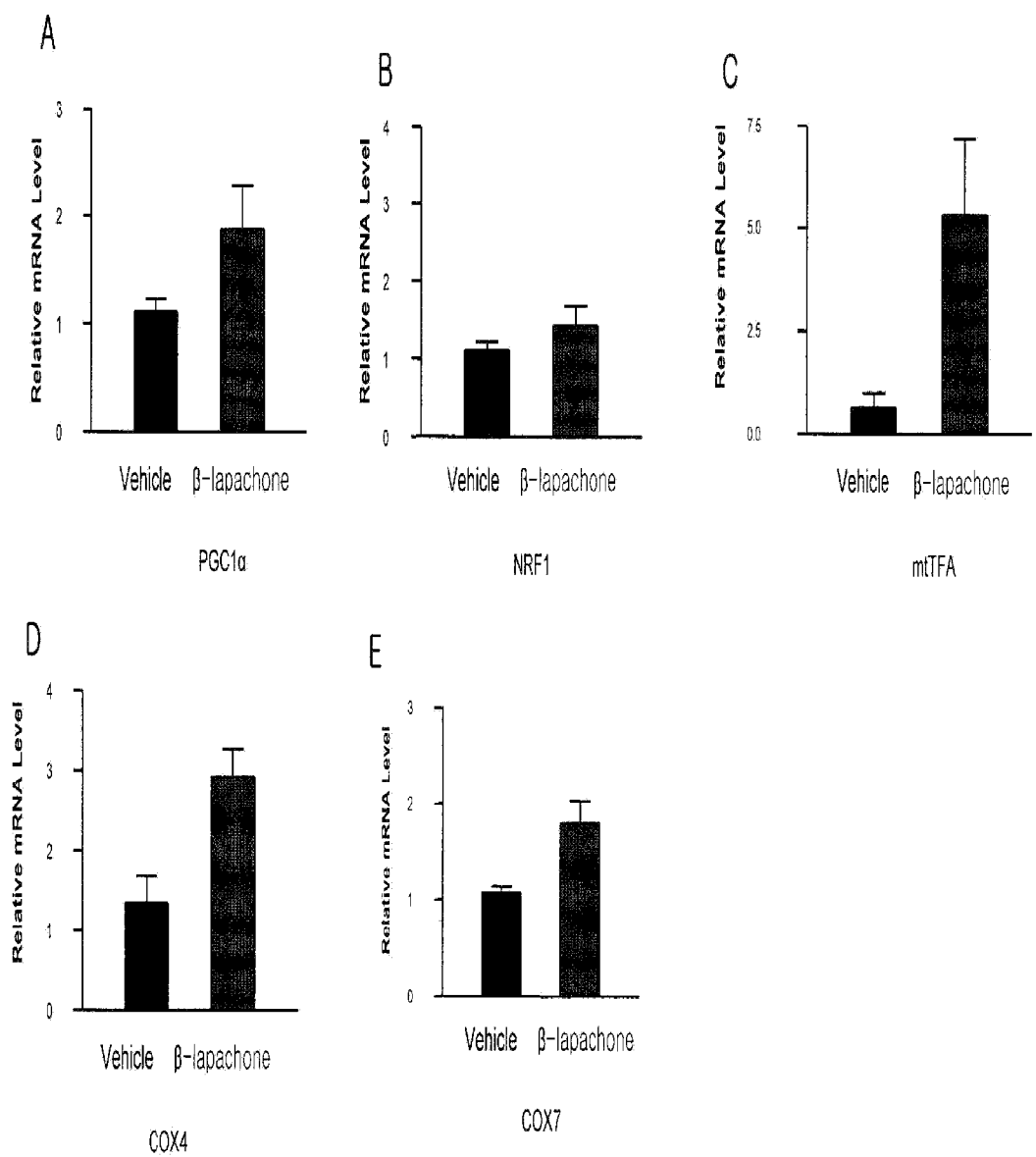
FIGS. 10A through 10E are graphs showing effects of β-lapachone on transcript expression of proteins involved in mitochondrial biogenesis of C57BL/6 mice.

Effects of β-Lapachone on Gene Expression of Proteins Involved in Mitochondrial Biogenesis of C57BL/6 Mice β-lapachone was administered daily to diet-induced obesity (DIO) mice at a dose of 50 mg/kg via an oral route, and levels of mRNAs of peroxisome proliferator-activated receptor coactivator alpha 1 (PGC1α) (23,24), nuclear respiratory factor 1 (NRF1) (25-27), mitochondrial transcription factor (mtTFA) (25-27), and cytochrome c oxidase (COX) 4 and 7 (28,29) in the liver and gonadal adipose tissues were confirmed by real-time quantitative PCR. Proteins shown in FIG. 10 are representative enzymes responsible for regulation of biogenesis of mitochondria which plays a critical role in biosynthesis of energy in cells, and are also known to be involved in regulation of various physiological events. Although there are slight differences in amounts of mRNAs between these enzymes, β-lapachone-administered groups exhibited increased levels of mRNAs for all enzymes, as compared to the control group. Since abnormal activity of mitochondria is reported in a variety of metabolic syndromes, these results show the possibility that β-lapachone can be therapeutic for the treatment of metabolic syndromes, mitochondrial dysfunction-related diseases and energy metabolism-related diseases, via amelioration of such phenomena.

Experimental Example 10

Figure 11:
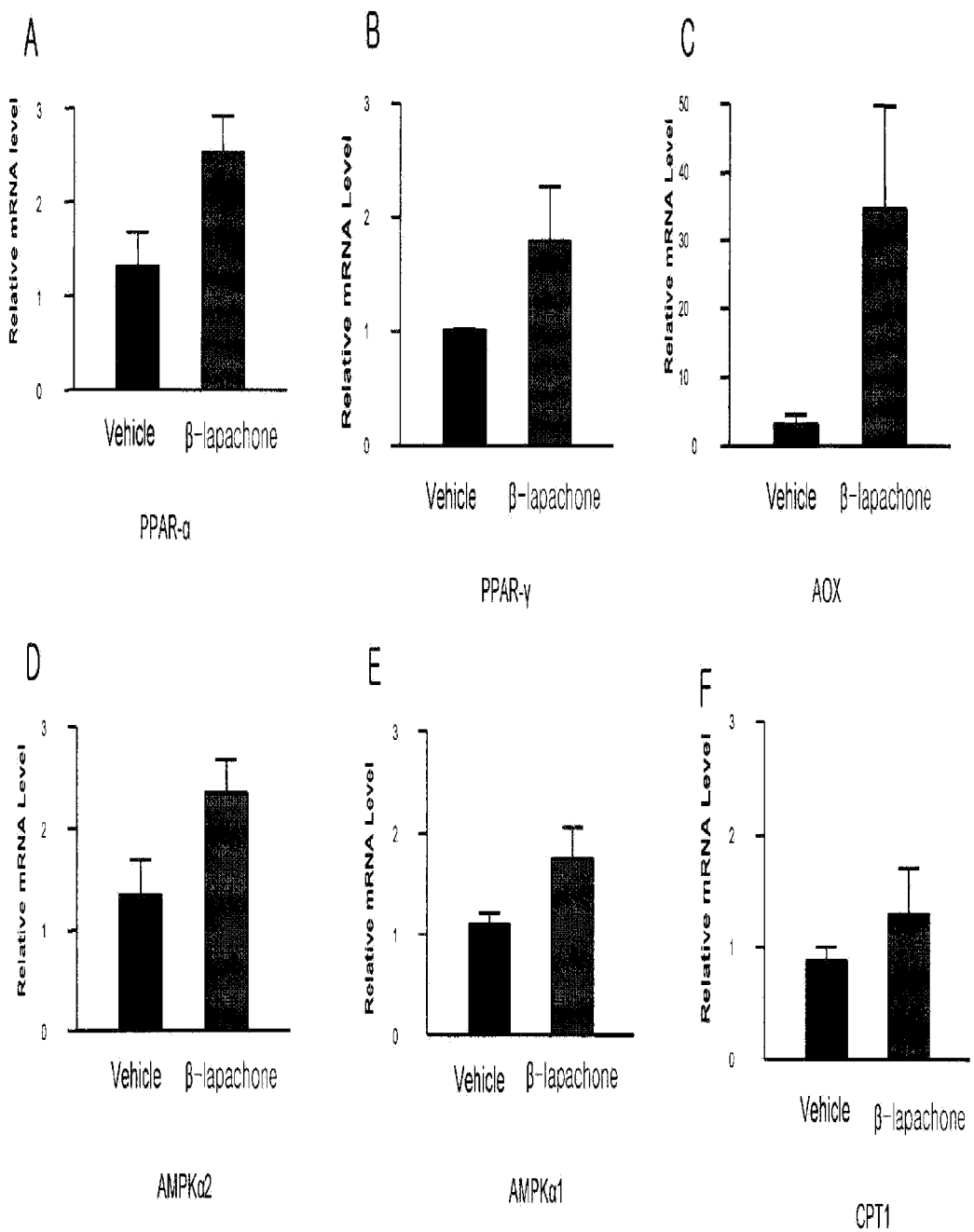
FIGS. 11A through 11F are graphs showing effects of β-lapachone on transcript expression of proteins in involved energy metabolism in C57BL/6 mice.

Effects of β-Lapachone on Expression of Genes Involved in Energy Metabolism of C57BL/6 Mice β-lapachone was administered daily to diet-induced obesity (DIO) mice at a dose of 50 mg/kg via an oral route, and levels of transcripts of genes involved in energy metabolism in the liver and gonadal adipose tissues were measured using real-time quantitative PCR. Referring to enzymes shown in FIG. 11, PPAR alpha and gamma are enzymes responsible for transcriptional regulation of enzymes involved in energy expenditure (30,31), AMPK plays a central role in the maintenance of cell energy homeostasis by sensing the intracellular AMP/ATP ratio, and AOX catalyzes to activate oxidative phosphorylation via oxidation of acyl CoA which resides in a certain step of a lipid metabolism process (32,33). In addition, CPT1 is also an enzyme involved in energy metabolism, and is well-known as an enzyme that enables the passage of long chain acyl CoA into mitochondria, not taking a route toward synthesis of triacylglycerol (34,35). In the group to which β-lapachone was administered, levels of mRNA of peroxisome proliferator activated receptor (PPAR) alpha was not changed, whereas PPAR gamma exhibited about two-fold increases in mRNA levels thereof. In addition, even though there are differences to some extent in mRNA levels between acyl CoA oxidase (AOX), AMP-activated protein kinase (AMPK) alpha 1 and 2, and carnitine palmitoyltransferase 1, the β-lapachone-administered groups exhibited increased levels in mRNAs of such enzymes, as compared to the control group. Increased expression levels of such genes show the possibility that β-lapachone can be as therapeutic for the treatment of energy metabolism-related diseases.

Experimental Example 11

Effects of β-Lapachone on Expression of SIRT-Related Transcripts in C57BL/6 Mice β-lapachone was administered daily to diet-induced obesity (DIO) mice at a dose of 50 mg/kg via an oral route, and levels of transcripts of Sirtuin (SIRT) (36,37) genes in gonadal adipose tissues were measured on days 7, 28 and 56 of administration, respectively, using real-time quantitative PCR. Referring to SIRT-related transcripts shown in FIG. 12, there are known 7 species of transcripts in humans. In particular, SIRT1 is well-known as an enzyme involved in longevity and it is also reported that SIRT1 is greatly increased when calories are ingested with limitation (37). As can be seen from FIG. 18, SITR1, SIRT3 and SIRT6 were significantly increased, while SIRT2, SIRT5 and SIRT7 did not exhibit any noticeable difference between the experimental groups and control group.

Experimental Example 12

Effects of β-Lapachone on Expression of Transcripts of UCP1 and UCP2 Genes in C57BL/6 Mice β-lapachone was administered daily to diet-induced obesity (DIO) mice at a dose of 50 mg/kg via an oral route, and levels of transcripts of uncoupling protein 1 & 2 (UCP 1 & 2) genes in the liver and gonadal adipose tissues was measured using real-time quantitative PCR. UCP 1 & 2 are enzymes that perform energy expenditure via heat generation, and it is reported that these enzymes function to consume energy without involving production of reactive oxygen species (ROS) and are also closely correlated with the incidence of obesity (38,39). As shown in FIG. 13, administration of β-lapachone has led to significant increases in mRNA levels of UCP1 & 2. These results show the possibility of β-lapachone as a safe therapeutic for the treatment of metabolic syndromes, via reduction of stress due to ROS that is additionally produced in an energy generation process.

Experimental Example 13

Figure 14:
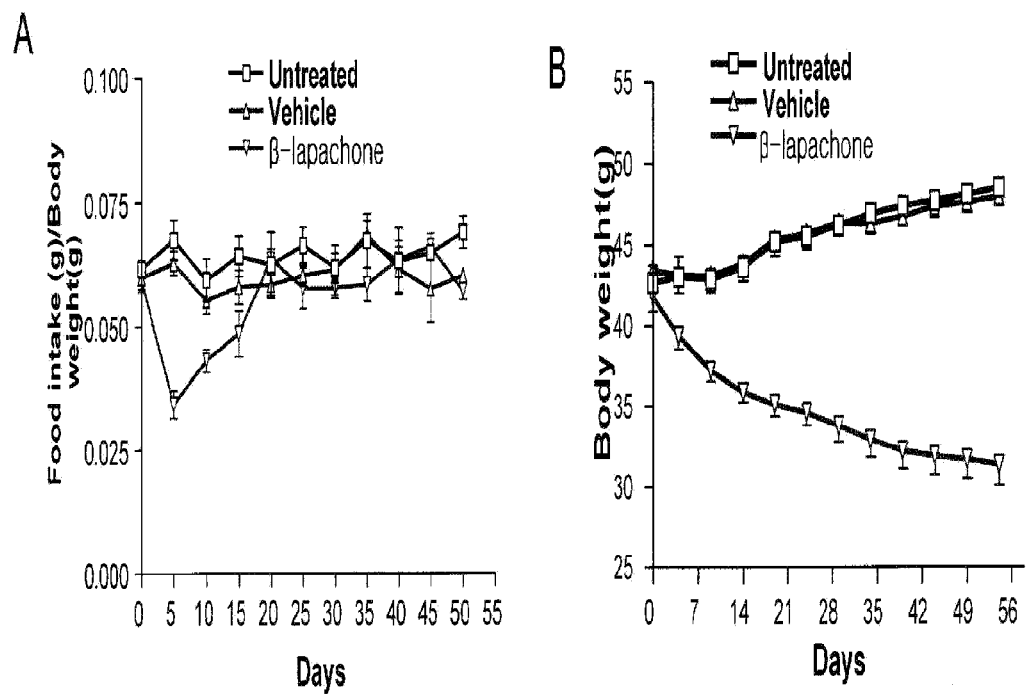
FIGS. 14A and 14B are graphs showing changes in body weight and diet with respect to the passage of time, after administration of β-lapachone in DIO C57BL/6 mice.

Effects of β-Lapachone Administration on Changes Over Time in Body Weight and Dietary Intake in Diet-Induced Obesity (DIO) C57BL/6 Mice FIG. 14 shows changes in dietary intake/body weight and weight changes for 56 days, after daily administration of β-lapachone into diet-induced obesity (DIO) mice at a dose of 50 mg/kg via an oral route. β-lapachone-administered group exhibited decreases in dietary intake for first two weeks, and thereafter the dietary intake level recovered similar to that of a control group. These results are believed to be due to decomposition of fat being facilitated and therefore sufficient amounts of energy are generated. In addition, even though mice were fed high-fat diet, animals exhibited a continuous weight loss for 56 days, as compared to a control group.

Figure 15:
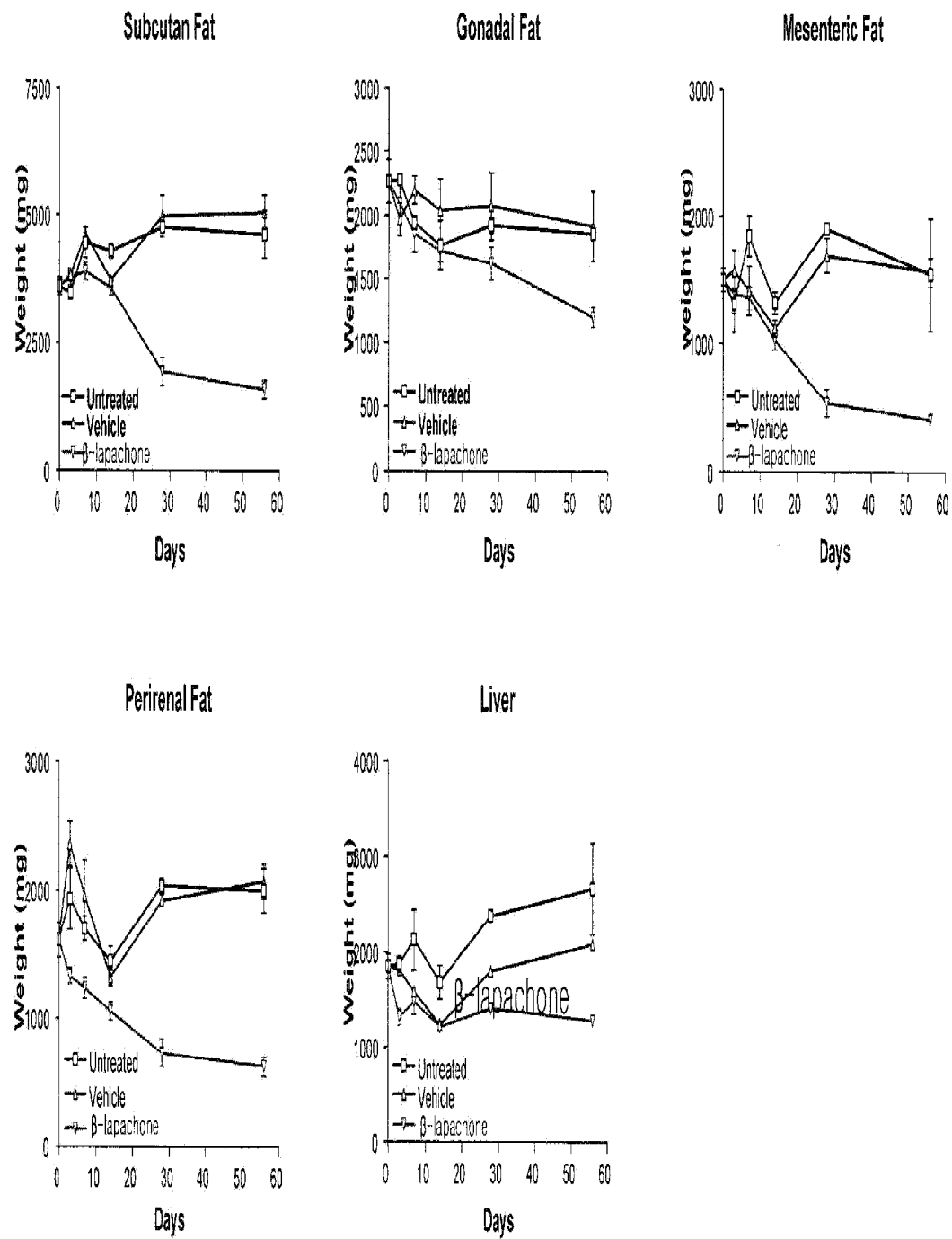
FIG. 15 is a graph comparing weight changes in various organs between the treatment group and control group after administration of β-lapachone to DIO C57BL/6 mice.

FIG. 15 is a graph comparing weight changes in various organs between the treatment group and control group after administration of β-lapachone to DIO C57BL/6 mice for 56 days; as shown in FIG. 15, there were significant changes in weight of tissues, resulting from decreased fat contents in organ tissues after administration of β-lapachone.

Figure 16:
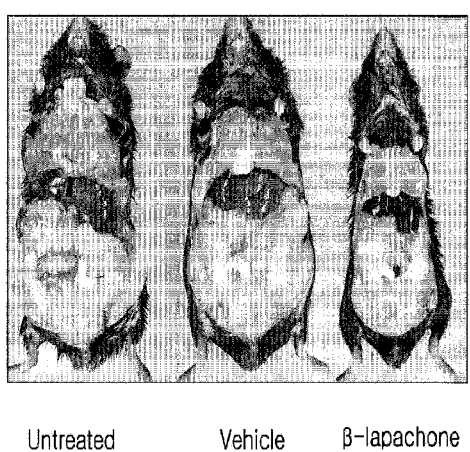
FIGS. 16A through 16C are photographs showing whole laparotomized states of animals after administration of β-lapachone to DIO C57BL/6 mice and results of oil red O staining and EM examination on fat accumulation in liver tissues.
Figure 16:
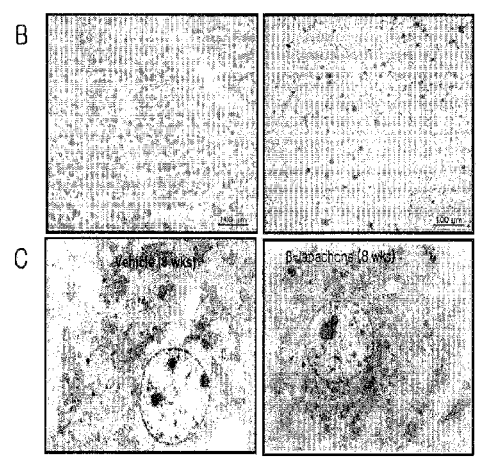

FIGS. 16A through 16C show whole laparotomized states of animals after administration of β-lapachone to DIO C57BL/6 mice for 56 days and results of oil red O staining and EM examination on fat accumulation in liver tissues. As can be seen from FIG. 16, C57BL/6 mice to which β-lapachone was administered for 56 days exhibited conspicuous decreases in visceral fat and body weight, and a reduced size of liver tissues that were turned into red color. In order to confirm improvement in condition of fatty liver in FIG. 16, accumulated fat in the liver was stained using oil red O staining and as a result, it was confirmed that fat has diminished by 90% or more, as compared to a control group. In addition, the results of EM examination on liver tissues exhibited remarkably decreased fat vacuoles and glycogen stores as compared to a control group, recovery of normal mitochondrial shape, significant increases in mitochondrial numbers, and improved shapes of endoplasmic reticulum.

Figure 17:
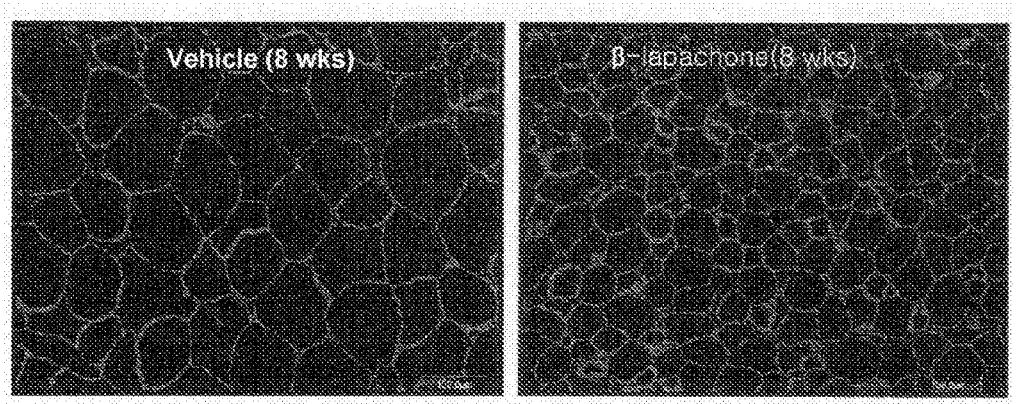
FIG. 17 is a photograph showing comparison results of the size of adipocyte in gonadal adipose tissues after administration of β-lapachone to DIO C57BL/6 mice.

Referring to FIG. 17, after daily administration of β-lapachone to DIO C57BL/6 mice at a dose of 50 mg/kg via an oral route, animals were laparotomized on day 56 of β-lapachone administration and perilipin staining was performed on gonadal adipose tissues. As can be seen from FIG. 17, the size of adipocytes was remarkably decreased.

Figure 18:
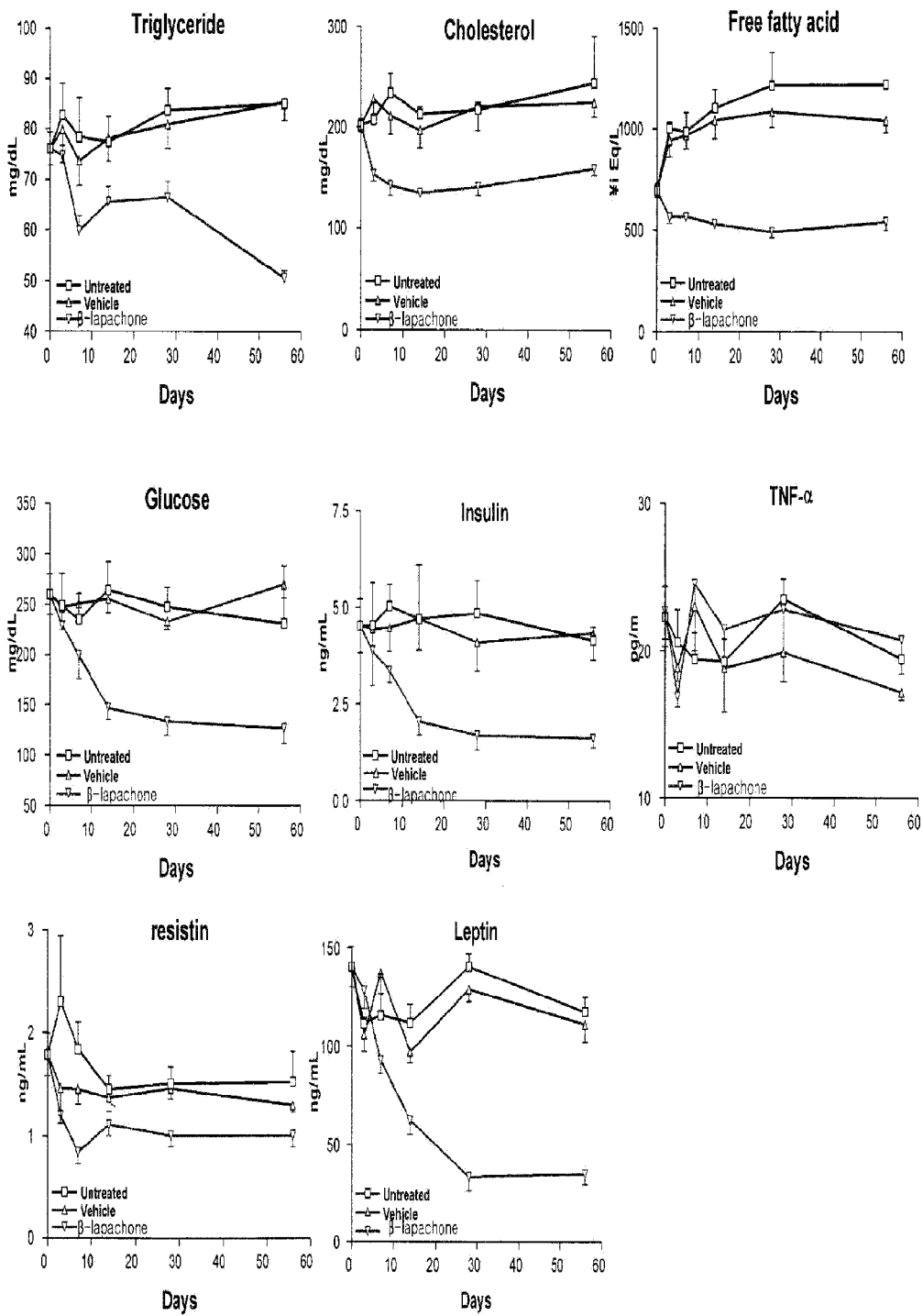
FIG. 18 is a graph showing changes in concentrations of blood lipid, glucose and hormone with respect to the passage of time after administration of β-lapachone to DIO C57BL/6 mice.

FIG. 18 shows changes in triglyceride (TG), cholesterol, free fatty acid, glucose, insulin, TNFα, resistin and leptin levels in the blood collected on days 3, 7, 14, 28 and 56, respectively, after daily administration of β-lapachone to DIO C57BL/6 mice at a dose of 50 mg/kg via an oral route. As can be seen there-from, blood fat and glucose levels were significantly improved and further, insulin resistance and leptin resistance were also improved. Further, a blood level of resistin, which causes insulin resistance, was also significantly improved. From these results, it is expected that β-lapachone will be highly effective for the treatment of fatty liver, hyperlipidemia, type 2 diabetes and insulin resistance.

Figure 19:
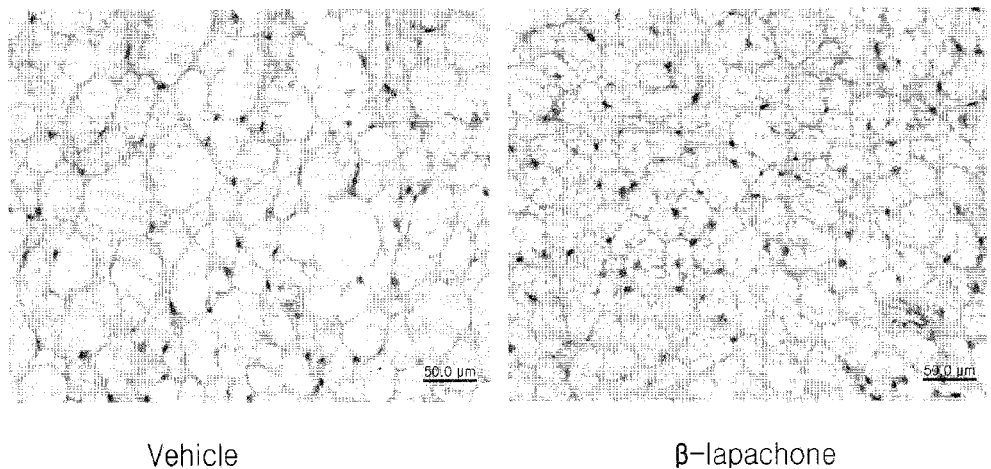
FIG. 19 is a photograph showing comparison results of H&E staining of brown adipose tissues after administration of β-lapachone to DIO C57BL/6 mice.

Referring to FIG. 19, after daily administration of β-lapachone to DIO C57BL/6 mice at a dose of 50 mg/kg via an oral route, H&E staining of brown adipose tissues was performed on day 56 of administration. As can be seen from FIG. 19, the size of adipocytes was remarkably decreased.

Figure 20:
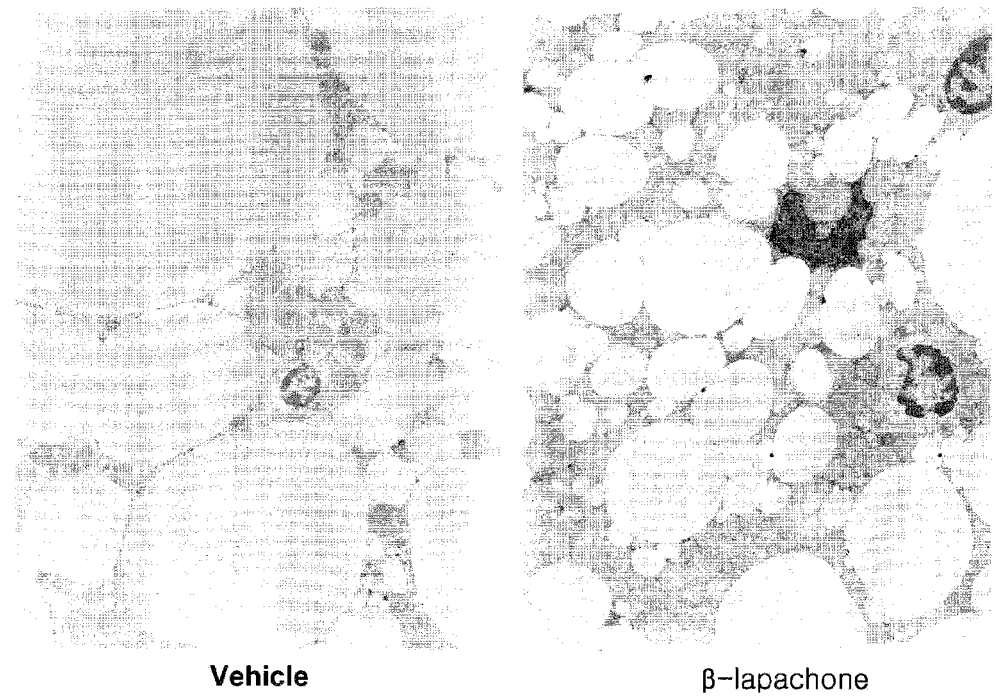
FIG. 20 is a photograph showing results of EM examination of brown adipose tissue after administration of β-lapachone to DIO C57BL/6 mice.

FIG. 20 shows results of EM examination of brown adipose tissue taken on day 56 after daily administration of β-lapachone to DIO C57BL/6 mice at a dose of 50 mg/kg via an oral route. As can be seen there-from, the size of adipocytes was remarkably decreased.

Experimental Example 14

Figure 21:
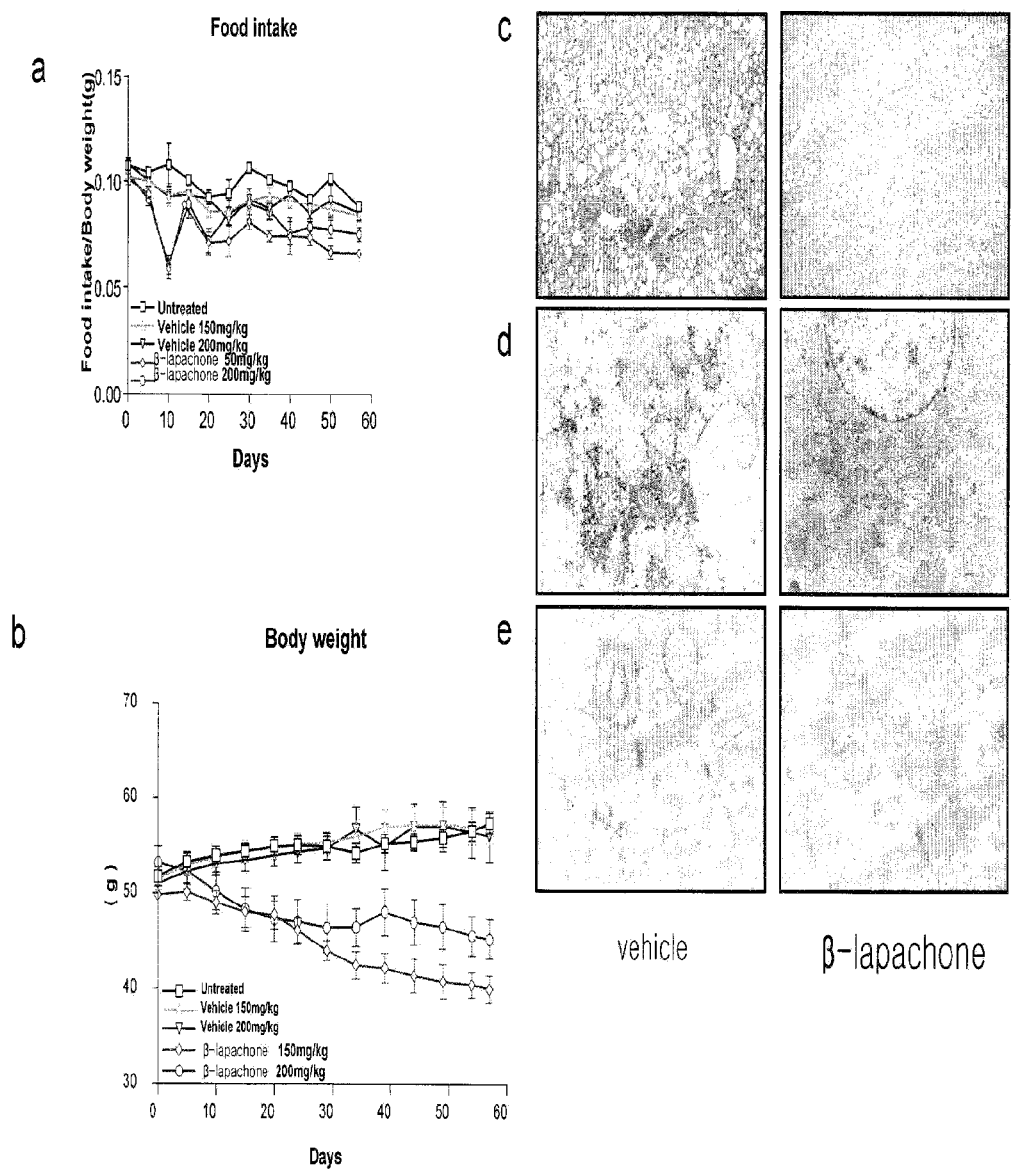
FIGS. 21A to 21E are graphs and photographs showing changes in dietary intake/g body weight, body weight and accumulation amount of fat, and EM examination results of tissue, after administration of β-lapachone to leptin receptor-deficient (ob/ob) mice.

Changes in Leptin Receptor-Deficient (Ob/Ob) Mice by Administration of β-Lapachone FIG. 21 shows changes in dietary intake/body weight (FIG. 21A) and changes in body weight (FIG. 21B) for 56 days, according to daily administration of β-lapachone into leptin receptor-deficient (ob/ob) mice at a dose of 150 or 200 mg/kg via an oral route. Dietary intake/body weight was notably decreased around at 10 days of administration, and thereafter the dietary intake level recovered similar to that of a control group. This is because fat degradation is facilitated and therefore sufficient amounts of energy are generated, despite similar dietary intake. In addition, even though mice were fed high-fat diet, animals exhibited a continuous weight loss for 56 days, as compared to a control group. These results show that administration of β-lapachone effectively decreases body weight in leptin receptor-deficient (ob/ob) mice as well as in obese mice. In order to examine fat accumulation in the liver tissue, animals were laparotomized 56 days after administration of β-lapachone, and H&E staining (FIG. 21C) and EM examination (FIG. 21D) were performed on the liver tissue. FIG. 21C shows through the results of H&E staining on liver tissue that almost all fat vacuoles have disappeared as compared to the control group. Such results present expectation that administration of β-lapachone will be highly effective to treat fatty liver in leptin receptor-deficient (ob/ob) mice as well. From FIG. 21D, the results of EM examination on liver tissues showed remarkably decreased fat vacuoles and glycogen stores as compared to the control group, recovery of normal mitochondrial shape, significant increases in mitochondrial numbers, and improved shapes of endoplasmic reticulum. From FIG. 21E, the results of EM examination on a muscle tissue of animal limbs showed the recovery of normal mitochondrial shape in the treatment group as compared to strange morphology of mitochondria shown in the control group, and significant increases in numbers of mitochondrial.

Experimental Example 15

Figure 22:
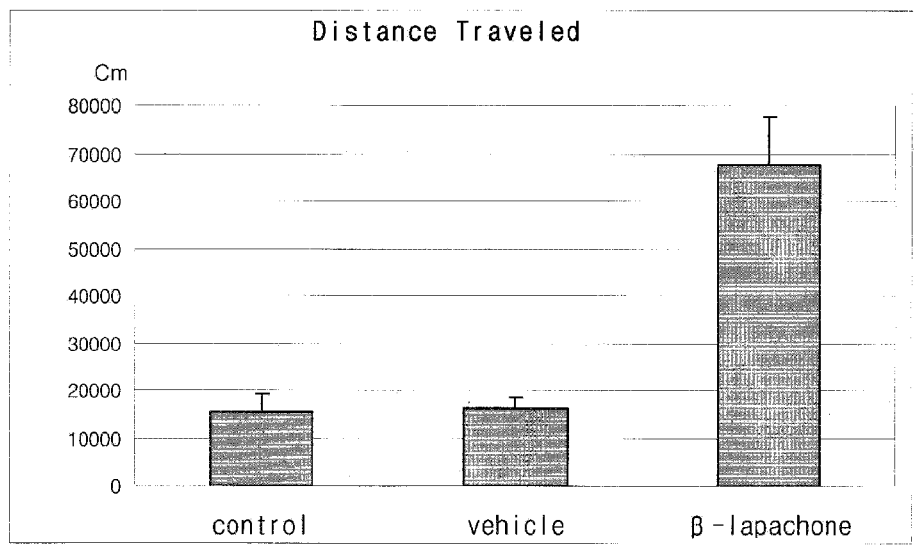
FIG. 22 is a graph showing effects of β-lapachone on spontaneous locomotor activity after administration of β-lapachone to DIO C57BL/6 mice.

Effects of β-Lapachone on Spontaneous Locomotor Activity

β-lapachone was administered to DIO C57BL/6 mice, and 3 hours later, spontaneous locomotor activity was measured using Versa MAX Activity Monitors & Analyzer (AccuSan Instruments, Columbus, Ohio). The monitor used to measure motion of animals was a 41 cm×41 cm Plexiglas chamber (height: 30 cm) equipped with infrared rays at intervals of 2.5 cm along the x- and y-axes, respectively, whereby 16 scanning lines are respectively arranged on front/rear and right/left sides of the chamber. In order to distinguish between spontaneous locomotor and stereotypic/grooming behavior, animal activity was measured by taking continuous interference of two different scanning lines caused by mice as an effective determination standard. A β-lapachone-administered group, a vehicle-administered group and a control group were respectively placed in each measuring apparatus, and activity and motion of animals were measured for 7 hours. For acclimation of animal to new environment, mice were placed in the apparatus 2 hours prior to measurement. As shown in FIG. 22, the vehicle-administered group and control group exhibited substantially no difference therebetween, but the β-lapachone-administered group exhibited a significant difference in motion and locomotor activity of animals.

Experimental Example 16

Effects of β-Lapachone on Enhancement of Physical Endurance

Figure 23:
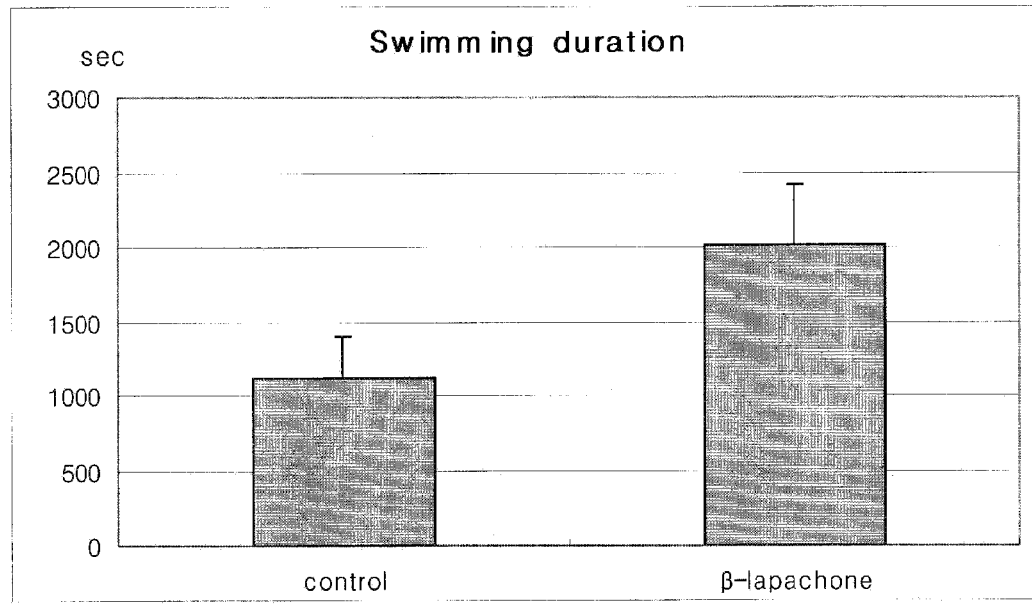
FIG. 23 is a graph showing effects of β-lapachone on enhancement of physical endurance after administration of β-lapachone to DIO C57BL/6 mice.

This Example was intended to measure difference in physical endurance of mice through a swimming test. For this purpose, water was placed in a cylindrical trough having a diameter of 9.5 cm and height of 25 cm, and β-lapachone was administered to DIO C57BL/6 mice. 3 hours later, a sample-administered group and a control group were placed simultaneously into each cylindrical trough for measurement, and physical endurance of each group was compared. As shown in FIG. 23, it was confirmed that β-lapachone-administered group exhibited more than two-fold swimming duration by single administration of β-lapachone, as compared to the control group.

Experimental Example 17

Effects of β-Lapachone on Respiratory Quotient (RQ)

Figure 24:
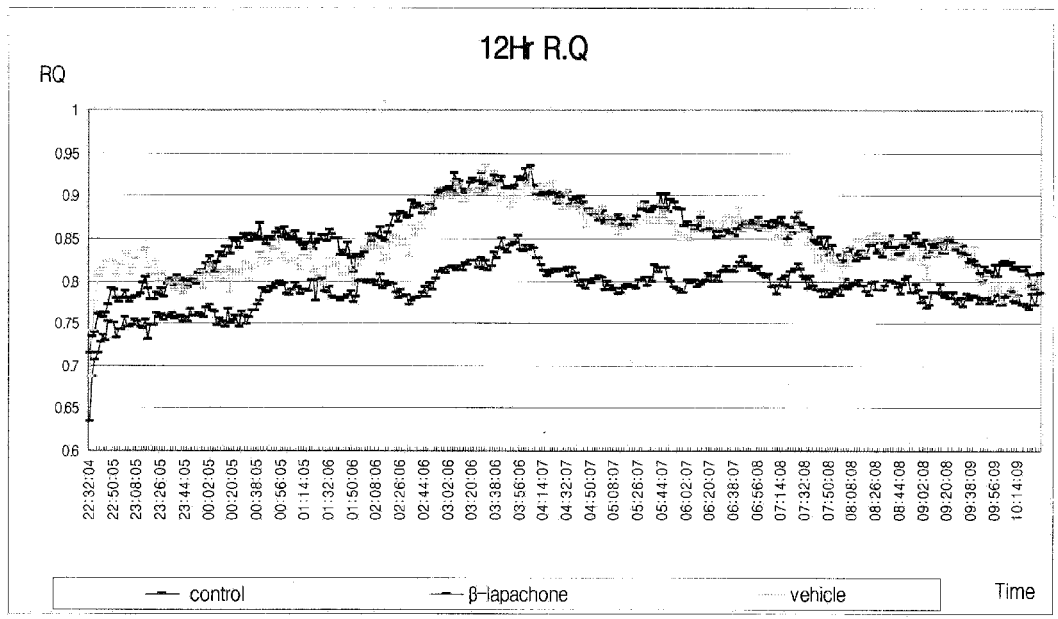
FIG. 24 is a graph showing effects of β-lapachone on Respiratory Quotient (RQ) after administration of β-lapachone to DIO C57BL/6 mice.

This Example was intended to examine effects of β-lapachone on fat metabolism via measurement of Respiratory Quotient (RQ). Oxygen consumption and carbon dioxide production were measured using an Oxyscan open-circuit indirect calorimeter (AccuScan Instruments, Columbus, Ohio). This apparatus consisted of enclosed acrylic chambers (21×21×21 cm). Fresh air was drawn into each chamber at a rate of 1500 ml/min and then $O_2$ and $CO_2$ were allowed to pass through detectors. The concentrations of the gases were recorded in ml/kg body weight/min. RQ was calculated as the volume of $CO_2$ produced ($VCO_2$) divided by the volume of $O_2$ consumed ($VO_2$). A β-lapachone-administered group, a vehicle-administered group and a control group were placed in each apparatus, and RQ was measured for 7 hours. For acclimation of animal to new environment, mice were placed in the apparatus 2 hours prior to measurement. As shown in FIG. 24, the thus-measured results have confirmed that the β-lapachone-administered group exhibited a significant difference in a RQ value, as compared to the vehicle-administered group and control group.

Experimental Example 18

Acute Toxicity Test

1. Oral Administration

Sprague-Dawley rats, weighing 250±7 g (Jung-Ang Lab Animal Inc., Seoul, Korea) were divided into 4 groups, consisting of 10 animals each, and were orally administered Compounds 1, 2, 3, 4, 12, 13, 14, 16, 17, 24, 25 and 26 in accordance with the present invention at doses of 50, 100, and 200 mg/kg, respectively. After oral administration, upon observing for 2 weeks whether toxicity was exhibited or not, none of the animals died in all four groups and no visually observable symptoms with exception of weight loss were noticed compared to the control group.

2. Peritoneal Administration

Sprague-Dawley rats, weighing 255±6 g (Jung-Ang Lab Animal Inc., Seoul, Korea) were divided into 4 groups, consisting of 10 animals each, and were peritoneally administered Compounds 1, 2, 3, 4, 12, 13, 14, 16, 17, 24, 25 and 26 in accordance with the present invention at doses of 50, 100 and 200 mg/kg, respectively. After peritoneal administration, upon observing for 2 weeks whether toxicity was exhibited or not, none of the animals died in all four groups and no visually observable symptoms with exception of weight loss were noticed compared to the control group.

It was confirmed from the above-mentioned results that Compounds in accordance with the present invention had no acute toxicity.

Hereinafter, Formulation Examples of the pharmaceutical composition in accordance with the present invention and Application Examples thereof to cosmetics will be described. These examples are provided only for illustrating the present invention and should not be construed as limiting the scope and sprit of the present invention

Formulation Example 1

Preparation of Tablet

| | |
|---|---|
| Compound 1 | 20 g |
| Milk serum protein | 820 g |
| Crystalline cellulose | 140 g |
| Magnesium stearate | 10 g |
| Hydroxypropylmethylcellulose | 10 g |

Formulation Example 2

Preparation of Powder

| | |
|---|---|
| Compound 1 | 2 g |
| Soybean protein | 58 g |
| Carboxycellulose | 40 g |
| Total | 100 g |

Formulation Example 3

Application of Inventive Compound to Cosmetic Lotion

| | |
|---|---|
| 1,3-butylene glycol | 5% |
| Glycerine | 5% |
| EDTA-2Na | 0.02% |
| Trimethylglycine | 2.0% |
| Cetanol | 1.0% |
| Glyceryl monostearate emulsifier | 1.0% |
| Polysorbate 60 | 1.2% |
| Sorbitan sesquioleate | 0.3% |
| Cetyl 2-ethyl-hexanoate | 4.0% |
| Squalane | 5.0% |
| Dimethicone | 0.3% |
| Glyceryl stearate | 0.5% |
| Carbomer | 0.15% |
| Triethanolamine | 0.5% |
| Imidazolidinyl urea | 0.2% |
| Compound 1 | 0.2% |
| Purified water | 73.6% |

Formulation Example 4

Application of Inventive Compound to Cosmetic Skin Care

| | |
|---|---|
| 1,3-butylene glycol | 4.0% |
| Dipropylene glycol | 5.0% |
| EDTA-2Na | 0.02% |
| Octyldodeceth-16 | 0.3% |
| PEG60 hydrogenated castor oil | 0.25% |
| Compound 1 | 0.03% |
| Purified water | 90% |

INDUSTRIAL APPLICABILITY

As apparent from the foregoing, it is expected that compounds in accordance with the present invention are compounds modulating activity of various genes and proteins, and therefore will be therapeutically effective for the treatment of various diseases and disorders via regulation of energy levels in vivo. Pharmaceuticals using the above-mentioned compounds as an active ingredient exhibit superior effects on the treatment and/or prevention of various disease such as obesity, diabetes, metabolic syndromes, degenerative diseases and mitochondrial dysfunction-related diseases.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of treating a liver disease, comprising administering to a subject in need thereof a pharmaceutical composition comprising:

(a) a therapeutically effective amount of a compound represented by Formula I:

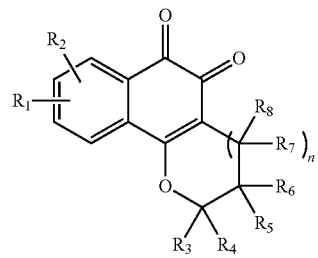

(I)

wherein $R_1$ and $R_2$ are each independently hydrogen, halogen, alkoxy, hydroxy or lower alkyl having 1 to 6 carbon atoms;

$R_3$, $R_4$, $R_5$, $R_6$, $R_7$ and $R_8$ are each independently hydrogen, hydroxy, $C_1$-$C_{20}$ alkyl, alkene or alkoxy, cycloalkyl, heterocycloalkyl, aryl or heteroaryl, or two substituents of $R_3$ to $R_8$ may be taken together to form a cyclic structure; and n is 0 or 1, with proviso that when n is 0, carbon atoms adjacent to n form a cyclic structure via a direct bond;

or a pharmaceutically acceptable salt thereof, and (b) a pharmaceutically acceptable carrier, a diluent or an excipient, or any combination thereof, wherein the liver disease is selected from the group consisting of a fatty liver, hepatic failure, liver function failure, and hepatomegaly.

2. The method according to claim 1, wherein the compound of Formula I is selected from the group consisting of compounds of Formula II and Formula III:

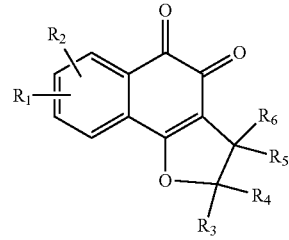

(II)

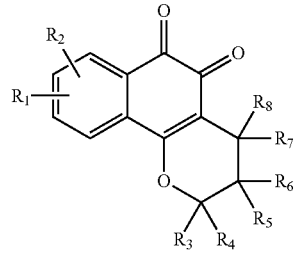

(III)

wherein, $R_1$, $R_2$, $R_3$, $R_4$, $R_5$, $R_6$, $R_7$ and $R_8$ are as defined in Formula I, or a pharmaceutically acceptable salt thereof.

3. The method according to claim 1, wherein each $R_1$ and $R_2$ is hydrogen.

4. The method according to claim 2, wherein the compound of Formula II is a compound of Formula IIa wherein $R_1$, $R_2$ and $R_4$ are independently hydrogen, or a compound of Formula IIb wherein $R_1$, $R_2$ and $R_6$ are independently hydrogen:

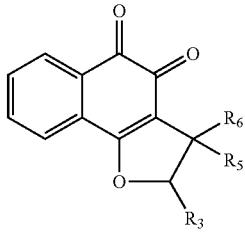

(IIa)

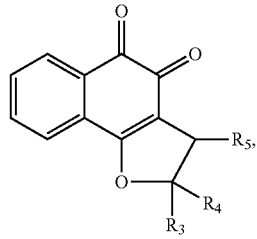

(IIb)

or a pharmaceutically acceptable salt thereof.

5. The method according to claim 2, wherein the compound of Formula III is a compound of Formula IIIa wherein $R_1$, $R_2$, $R_5$, $R_6$, $R_7$ and $R_8$ are independently hydrogen:

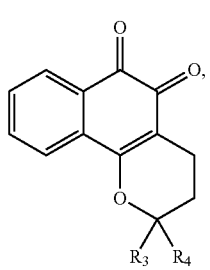
(IIIa)
or a pharmaceutically acceptable salt thereof.
6. The method according to claim 1, wherein the compound of Formula I is β-lapachone having the following formula:
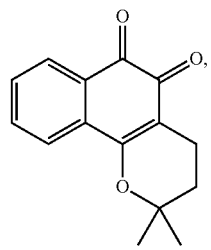 [SMILES: CC1(C)CCC2=C(O1)c1ccccc1C(=O)C2=O]
or a pharmaceutically acceptable salt thereof.
* * * * *